US00RE38332E

(19) United States
(12) Reissued Patent
Mallamo et al.

(10) Patent Number: US RE38,332 E
(45) Date of Reissued Patent: Nov. 25, 2003

(54) SELECTED SOLUBLE ESTERS OF HYDROXYL-CONTAINING INDOLOCARBAZOLES

(75) Inventors: John P. Mallamo, Glenmore, PA (US); Robert L. Hudkins, Chester Springs, PA (US)

(73) Assignees: Cephalon, Inc., West Chester, PA (US); Kyowa Hakko Kogyo Co., Ltd., Tokyo (JP)

(21) Appl. No.: 09/811,725

(22) Filed: Mar. 19, 2001

Related U.S. Patent Documents

Reissue of:
(64) Patent No.: 5,686,444
Issued: Nov. 11, 1997
Appl. No.: 08/624,707
Filed: Mar. 26, 1996

U.S. Applications:

(63) Continuation-in-part of application No. 08/417,611, filed on Apr. 5, 1995, now Pat. No. 5,650,407.

(51) Int. Cl.[7] ..... A61K 31/5513; C07D 498/22
(52) U.S. Cl. ..... 514/211.08
(58) Field of Search ..... 540/545; 514/43, 514/183, 185, 211.08

(56) References Cited

U.S. PATENT DOCUMENTS

| | | | | |
|---|---|---|---|---|
| 4,877,776 | A | 10/1989 | Murakata et al. | 514/43 |
| 4,923,986 | A | 5/1990 | Murakata et al. | 540/545 |
| 5,461,146 | A | 10/1995 | Lewis et al. | 540/545 |
| 5,650,407 | A | 7/1997 | Mallamo et al. | 514/185 |
| 5,686,444 | A | 11/1997 | Mallamo et al. | 514/211 |

FOREIGN PATENT DOCUMENTS

| | | |
|---|---|---|
| JP | 63-295588 | 1/1988 |
| WO | WO 93/08809 | 5/1993 |
| WO | WO 94/02488 | 3/1994 |
| WO | WO 94/06799 | 3/1994 |
| WO | WO 94/20106 | 9/1994 |
| WO | WO 94/27982 | 12/1994 |

OTHER PUBLICATIONS

Akinaga, S., et al., "Antitumor effect of KT6124, a novel derivative of protein kinase inhibitor K–252a, and its mechanism of action," *Cancer Chemother Pharm.*, 1992, 266–272.

Isaacs, J. et al., "Establishment and Characterization of Seven Dunning Rat Prostatic Cancer Cell Lines and Their Use in Developing Methods for Predicting Metastatic Abilities of Prostatic Cancers", *The Prostate* 1986, 9, 261–281.

Greene and Wuts, "Protective Groups in Organic Synthesis", 2nd ed., Wiley & Sons, New York, 1991.

Joyce, et al., "Synthesis of the aromatic and monosaccaride moieties of staurosporin," *J. Org. Chem.*, 1987, 52(7), 1177–1183.

March, J., "Advanced Organic Chemistry", 3rd Edition, Wiley & Sons, New York, 1985.

"Remington's Pharmaceutical Sciences", Mack Publishing Co., Easton, PA, 1980.

*Primary Examiner*—Richard L. Raymond
(74) *Attorney, Agent, or Firm*—Woodcock Washburn LLP

(57) ABSTRACT

Esters of hydroxyl-containing indolocarbazoles and acids containing selected solubilizing groups are provided. Compositions including the indolocarbazole esters and methods for the use of the indolocarbazole esters are also provided.

46 Claims, 15 Drawing Sheets

SELECTED SOLUBLE ESTERS OF HYDROXYL-CONTAINING INDOLOCARBAZOLES

Matter enclosed in heavy brackets [ ] appears in the original patent but forms no part of this reissue specification; matter printed in italics indicates the additions made by reissue.

This application is *a reissue of U.S. application Ser. No. 08/624,707 filed Mar. 26, 1996, now U.S. Pat. No. 5,686, 444, which is* a continuation-in-part of U.S. application Ser. No. 08/417,611 filed Apr. 5, 1995, *now U.S. Pat. No. 5,650,407.*

FIELD OF THE INVENTION

This invention relates to novel esters of hydroxyl-containing indolocarbazoles and acids containing selected solubilizing groups, to compositions including the indolocarbazole esters and to methods for the use of the indolocarbazole esters in the elucidation and understanding of certain diseases, including diseases of the prostate.

BACKGROUND OF THE INVENTION

Indolocarbazoles are a well-known class of small molecules. In animal studies, activity of indolocarbazoles as therapeutic agents in the treatment of pathological disorders of the prostate have been demonstrated. Additionally, indolocarbazoles are useful as inhibitors of protein kinases C, A and G, myosin light chain kinase, and trk, a tyrosine kinase activated by neurotrophins. Indolocarbazoles have been also shown to be active neurologic agents.

U.S. Pat. No. 4,877,776 describes indolocarbazole derivatives which exhibit protein kinase C-inhibiting activity. U.S. Pat. No. 4,923,986 and PCT patent specification WO94/02488 describe physiologically-active indolocarbazole derivatives having anti-tumor activities. PCT patent specification WO94/27982 describes the use of indolocarbazole derivatives to treat a pathological condition of the prostate gland in a mammal. Japanese Patent Specification JP63-295588 describes indolocarbazole derivatives which are inhibitors of protein kinase C. PCT patent specification WO93/08809 describes indolocarbazole derivatives which potentiate neurotrophic activity. PCT patent specification WO94/06799 describes indolocarbazole derivatives as therapeutic agents for thrombocytopenia.

A significant problem which has limited the usefulness of indolocarbazoles as therapeutic and research reagents is their poor solubility in aqueous solutions. In light of the significant useful activities of indolocarbazoles, there is a need for novel indolocarbazole derivatives which achieve the beneficial effects of indolocarbazoles and which have increased aqueous solubility. Such compounds would allow for in vivo delivery of indolocarbazole-containing solutions without creating additional problems for the recipient. This invention is directed to this important end.

SUMMARY OF THE INVENTION

The present invention provides novel soluble esters of hydroxyl-containing indolocarbazoles. The subject invention also includes compositions including the indolocarbazole esters, and methods for the use of the indolocarbazole esters in the treatment of diseases, including pathological conditions of the prostate gland.

In one aspect, compounds are provided having the formula Q—L—C(═O)—A wherein A is a solubilizing group, L is oxygen and Q is an indolocarbazole residue of Formula I:

I

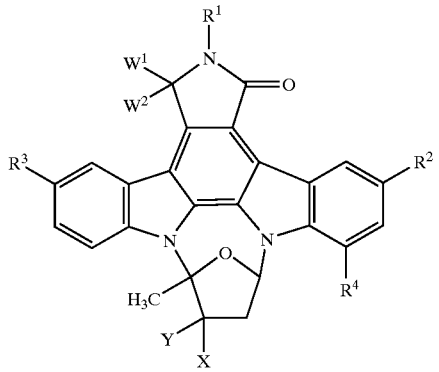

Constituent members are defined infra, as well as preferred constituent members.

The compounds of the invention are useful in a variety of applications. For example, the compounds may be employed in research applications to understand, for example, the mechanistic aspect of the therapeutic benefits derived therefrom, i.e., in the exploitation of scientific understanding of how these small molecules effectuate a positive result on certain cancerous tumors. Additionally, particularly preferred compounds of the invention can be utilized as a screening tool to discover other small molecules which offer equivalent efficacious results in in vitro and in vivo models of disease states of interest.

In a clinical setting, compositions comprising the claimed compounds are preferably used as therapeutics for treating a pathological condition of the prostate gland, e.g., benign prostatic hypertrophy or prostate cancer; compositions comprising the claimed invention are also useful as therapeutics for the treatment of neurological diseases.

These and other features of the compounds will be set forth in expanded form as the disclosure continues.

DETAILED DESCRIPTION OF THE PREFERRED EMBODIMENTS

Figure 1:
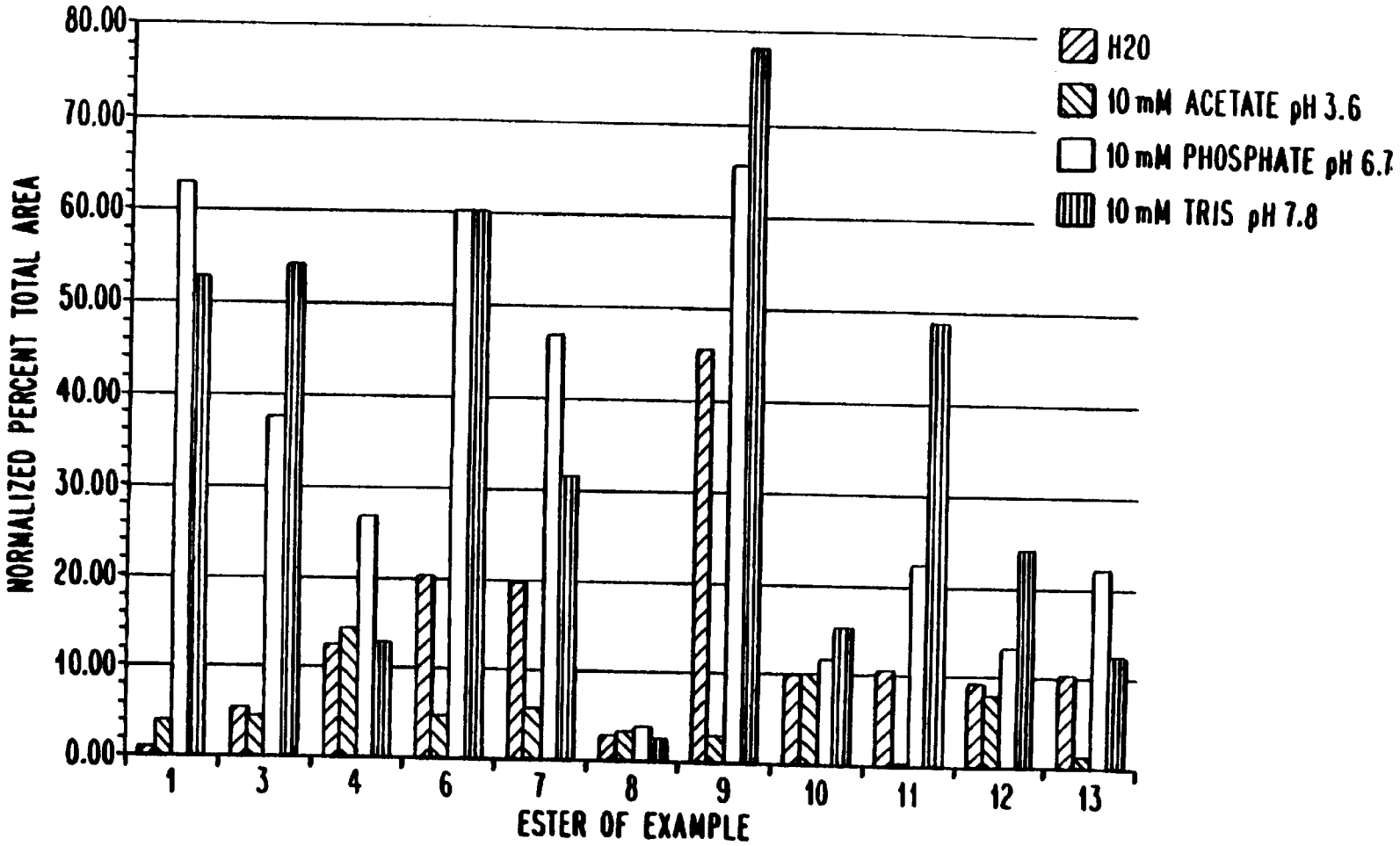
FIG. 1 shows the results of the initial screening of the stability of indolocarbazole esters in buffered solution.

The present invention provides novel indolocarbazole esters having the formula Q—L—C(═O)—A wherein:

A is a solubilizing group;

L is oxygen, and

Q is an indolocarbazole residue of formula:

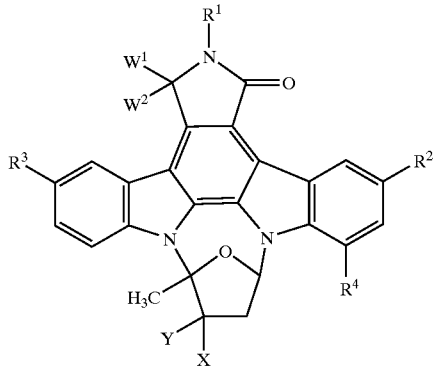

wherein:

$R^1$ is hydrogen, carbamoyl, lower alkyl, amino, lower alkanoyl, —$CH_2R^5$ or —$CH_2CH_2R^5$;

$R^5$ is halogen, amino, di-lower alkylamino, hydroxyl, a single bond attached to —L—C(═O)—A, or lower alkylamino optionally substituted with hydroxyl or a single bond attached to —L—C(═O)—A;

$R^2$ and $R^3$ are independently hydrogen, hydroxyl, cyano, lower alkoxy, halogen, hydroxymethyl, lower alkoxymethyl, substituted or unsubstituted lower alkylthiomethyl, lower alkylsulfinylmethyl, arylthiomethyl, heteroarylthiomethyl, arylsulfinylmethyl, heteroarylsulfinylmethyl, arylmethylthiomethyl, heteroarylmethylthiomethyl, CH═NNHC(═NH)$NH_2$, nitro, lower alkanoyl, lower alkanoyloxy, sulfonic acid, —$SO_2NR^8R^9$, —OC(═O)$NR^8R^9$, —CH═NN$R^8R^9$, —$NR^6R^7$, —$OCO_2R^{10}$, —NHC(═O)$NHR^{11}$, —$CH_2$OC(═O)$NHR^{11}$, —$NHCO_2R^{11}$, lower alkyl sulfonylmethyl, (dialkylamino)alkylthiomethyl, a single bond attached to —L—C(═O)—A, or lower alkyl optionally substituted with hydroxyl or a single bond attached to —L—C(═O)—A;

one of $R^6$ and $R^7$ is hydrogen and the other is hydrogen, lower alkyl, carbamoyl, lower alkylaminocarbonyl, lower alkanoyl or phenylaminocarbonyl; or $R^6$ and $R^7$ are both lower alkyl;

$R^8$ and $R^9$ are independently hydrogen, lower alkyl, aryl, heteroaryl or groups that form a heterocycle with adjacent nitrogen atoms;

$R^{10}$ is lower alkyl or substituted or unsubstituted phenyl;

$R^{11}$ is hydrogen or lower alkyl;

$R^4$ is hydrogen, amino or —NHC(═O)$NHC_2H_5$;

one of $W^1$ and $W^2$ is hydrogen, and the other is selected from the group consisting of hydrogen, hydroxyl, lower alkoxy, lower alkylthio and a single bond attached to —L—C(═O)—A, or $W^1$ and $W^2$ combined together are oxygen;

X is hydrogen, —$CH_2$—NHC(═O)O—$C_6H_5$, formyl, carboxyl, alkoxycarbonyl having from 2 to 13 carbons, cycloalkoxycarbonyl having from 4 to 11 carbons, —$(CH_2)_nCH_2N(R^{11})_2$ wherein n is an integer from 0 to 5, —C(═O)$NR^{12}R^{13}$, —$CH_2$B, —$NR^{14}R^{15}$, —N═CHN$(CH_3)_2$, —OCO$CH_2CH_2CO_2$H, lower alkylhydrazinocarbonyl, —CH═N—$R^{16}$, —CONH$R^{17}$, a group of formula:

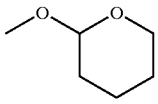

or —$CH_2$E where E represents a sugar residue having the formula:

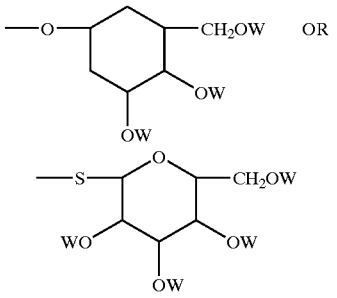

wherein W is hydrogen, methyl, ethyl, benzyl, acetyl, or trifluoroacetyl;

$R^{12}$ and $R^{13}$ are independently hydrogen, lower alkyl, phenyl, lower alkyl optionally substituted by hydroxyl or by a single bond attached to —L—C(═O)—A, or $R^{12}$ and $R^{13}$ are combined together to form a 3–6 carbon heterocyclic ring which optionally contains at least one O, S and/or additional N heteroatom, or $R^{12}$ is hydrogen and $R^{13}$is hydroxyl, a single bond attached to —L—C(═O)—A or phenyl;

B is hydroxyl, lower alkoxy, lower alkanoyloxy, azido, lower alkythio, arylthio, heteroarylthio, lower alkylsulfinyl, arylsulfinyl, heteroarylsulfinyl or a single bond attached to —L—C(═O)—A;

one of $R^{14}$ or $R^{15}$ is hydrogen and the other is hydrogen, lower alkyl, allyl, carboxyl-substituted lower alkyl, carbamoyl, lower alkyl- or aryl-substituted carbamoyl, a residue of an α-amino acid in which the carboxylate [hydrogen] *group* is removed, or lower alkoxycarbonyl-substituted lower alkyl; or both $R^{14}$ and $R^{15}$ are lower alkyl or chlorine-substituted lower alkyl; or $R^{14}$ and $R^{15}$ are combined together to form —$CH_2CH_2DCH_2CH_2$— wherein D is —$CH_2$—, —NH—, —S— or —O—;

$R^{16}$ is hydroxyl, carbamoylamino, —$NR^8R^9$ guanidino, 2-imidazolylamino or a single bond attached to —L—C(═O)—A;

$R^{17}$ is the residue of an α-amino acid after removal of the amino group thereof, wherein the carboxyl group of the α-amino acid is optionally esterified by a lower alkyl alcohol or benzyl alcohol;

Y is hydroxyl, lower alkanoyloxy, carbamoyloxy, lower alkoxy, or a single bond attached to —L—C(=O)—A, or X and Y together may be $—CH_2OC(CH_3)_2O—$, O=, $—CH_2O—$, $—CH_2OCO_2—$, $—CH_2OC(=S)O—$, $—CH_2N(R^{18})CO_2—$, $—CH_2NHC(=S)O—$, $—CH_2OS(=O)O—$, $—OC(=S)NHCH_2—$ or $—O—C(R^{19})=N—CH_2—$;

$R_{18}$ is hydrogen, lower alkyl, allyl, formylmethyl, $—CH_2CH=NNHC(=NH)NH_2$, $—CH_2CH(—G)CH_2—J$ wherein G and J are independently hydroxyl or one of them is a single bond attached to —L—C(=O)—A; and $R_{19}$ is lower alkyl or lower alkylthio;

provided that one of $R^2$, $R^3$, $R^5$, $W^1$, $W^2$, X and Y contains a single bond attached to —L—C(=O)—A;

further provided that where $R^1$, $R^2$, $R^3$, $R^4$, $W^1$ and $W^2$ are H, Y cannot be hydroxyl when X is $—CH_2—O—C(=O)CH_2NH_2$ or $—CH_2—O—C(=O)CH_2NH$-cbz;

and further provided that the solubilizing group A is other than a residue of succinic acid.

The solubilizing group A can be an amino acid residue, a dipeptide residue, $—(CH_2)_mZ$, $—(CH_2)_mC(=L)NH(CH_2)_mZ$, $—(CH_2)_mC(=O)NH—Z$, $—(CH_2)_mZ(CH_2)_mZ$, branched $—(CH_2)_nCH[(CH_2)_mZ]_2$, $—(CH_2)_m—Z[(CH_2)_mZ]_2$, $—(CH_2)_n—A^1$, $—(CH_2)_n$-heteroaryl and $—NH(CH_2)_mN(CH_3)_2$; wherein:

n is an integer from 0 to 5;

m is an integer from 1–6;

Z is selected from the group consisting of a basic group, $—C(=NH)NH_2$, cyclic amidine, $—NHC(NH_2)=NR^{11}$, cyclic guanidine and an acidic group, with the proviso that the solubilizing group A is not a succinic acid residue; and $A^1$ is aryl or heteroaryl substituted with one to three substituents of formula $—(CH_2)_nZ$, wherein heteroaryl refers to a an aryl moiety which contains at least one basic nitrogen atom and 0–4 heteroatoms selected from O, S and N.

$R^1$ is preferably hydrogen. Preferred $R^2$ and $R^3$ groups can independently be H, $NH_2$, hydroxyl, halogen, substituted or unsubstituted lower alkylthiomethyl, lower alkylsulfinylmethyl, arylthiomethyl, lower alkyl sulfonylmethyl, (dialkylamino)alkylthiomethyl, heteroarylmethylthiomethyl, or heteroarylthiomethyl.

Especially preferred $R^2$ and $R^3$ groups include H, $NH_2$, OH, halogen, $CH_2S(=O)C_2H_5$, $CH_2SC_2H_5$, $CH_2SC_6H_5$, $CH_2S(=O)_2C_2H_5$, $CH_2S(CH_2)_2N(CH_3)_2$, $CH_2SCH_2$-(2-furyl) and $CH_2S$-3-(1,2,4-triazolyl), with H and substituted or unsubstituted lower alkylthiomethyl groups being particularly preferred.

Y is preferably hydroxyl or lower alkoxy, particularly methoxy or a single bond attached to —L—C(=O)—A, X is preferably methoxycarbonyl, $—CH_2—S(=O)CH_3$, $—CH_2N(CH_3)_2$, hydroxymethyl, glucosylthiomethyl, particularly $—CH_2—S$-1-glucosyl), $—CH_2—NHC(=O)O—C_6H_5$ or $—C(=O)NH(CH_2)_2—OH$.

$R^4$ is preferably H, $—NH_2$ or $—NHC(=O)NHC_2H_5$.

In some especially preferred embodiments $R^2$ and $R^3$ are both H, Y is lower alkoxy, particularly methoxy, and X is $CH_3$—B where B is a single bond attached to —L—C(=O)—A.

In other especially preferred embodiments $R^2$ and $R^3$ are both lower alkylthiomethyl, particularly $—CH_2SC_2H_5$, Y is a single bond attached to —L—C(=O)—A and X is methoxycarbonyl.

In preferred embodiments the indolcarbazole (Q—OH) of the indolocarbazole ester has one of the formulas in Table 1.

TABLE 1

| Compound[(1)] | $R^2$ | $R^3$ | Y | X |
|---|---|---|---|---|
| I-1 | H | H | OH | $CO_2CH_3$ |
| I-2 | OH | H | OH | $CO_2CH_3$ |
| I-3 | H | H | OH | $CH_2S(=O)CH_3$ |
| I-4 | H | H | OH | $CH_2N(CH_3)_2$ |
| I-5 | H | H | $OCH_3$ | $CH_2OH$ |
| I-6[(2)] | H | H | OH | $CH_2S$-Glc |
| I-7[(3)] | H | H | OH | $CO_2CH_3$ |
| I-8 | $CH_2S(=O)C_2H_5$ | H | OH | $CO_2CH_3$ |
| I-9[(3)] | Br | Br | OH | $CO_2CH_3$ |
| I-10 | $CH_2SC_2H_5$ | H | OH | $CO_2CH_3$ |
| I-11 | $CH_2SC_6H_5$ | H | OH | $CO_2CH_3$ |
| I-12 | H | H | OH | $CH_2NHCO_2C_6H_5$ |
| I-13 | $CH_2S(=O)_2C_2H_5$ | H | OH | $CO_2CH_3$ |
| I-14 | $CH_2SC_2H_5$ | $CH_2SC_2H_5$ | OH | $CO_2CH_3$ |
| I-15 | $CH_2S(CH_2)_2N(CH_3)_2$ | H | OH | $CO_2CH_3$ |
| I-16 | $CH_2SCH_2$-2-Furyl | H | OH | $CO_2CH_3$ |
| I-17 | Br | Br | OH | $CO_2CH_3$ |
| I-18 | $CH_2S$-3-(1,2,4-Triazolyl) | H | OH | $CO_2CH_3$ |
| I-19 | $CH_2S(CH_2)_2N(CH_3)_2$ | $CH_2S(CH_2)_2N(CH_3)$ | OH | $CO_2CH_3$ |
| I-20[(4)] | H | H | OH | $CO_2CH_3$ |
| I-21[(5)] | H | $NH_2$ | OH | $CO_2CH_3$ |
| I-22 | H | H | OH | $C(=O)NH(CH_2)_2OH$ |

[(1)]$W^1$ and $W^2$ are both hydrogen, or both are combined together to represent oxygen, where indicated in Footnote 3. $R^1$ is hydrogen. $R^4$ is hydrogen except as noted in Footnotes 4 and 5.
[(2)]Glc is glucose; linkage is through the 1-position.
[(3)]$W^1$ and $W^2$ are combined together to represent oxygen.
[(4)]$R^4$ is $NHCONHC_2H_5$.
[(5)]$R^4$ is $NH_2$.

Indolocarbazoles I-5 and I-14 of Table 1, which are particularly preferred indolocarbazoles, are disclosed in International Publication WO 94/02488 (Table 1) as compounds II-4 and II-51, respectively, and in U.S. Pat. No. 5,461,146. Indolocarbazole I-5 is additionally disclosed in International Publication WO 94/27982 (Table 1) as compound I-19.

The novel indolocarbazole esters of the invention may be prepared by the esterification of a hydroxyl-containing indolocarbazole of formula HO—Q and an acid AC(═O)OH containing one or more selected solubilizing groups (A) according to the equation:

$$AC(=O)OH+HO—Q \rightarrow ACO_2—Q$$

In some preferred embodiments, the acid in the above equation has one of the formulas shown in Table 2, particularly one of the formulas $A_1$–$A_{10}$, with $A_5$ and $A_{10}$ being more preferred and $A_{10}$ being especially preferred.

TABLE 2

| Compound No. | Acid |
|---|---|
| $A_1$ | Lysine |
| $A_2$ | Glycine |
| $A_3$ | Alanine |
| $A_4$ | N,N-Dimethylglycine |
| $A_5$ | 3-Dimethylaminobutyric Acid |
| $A_6$ | Histidine |
| $A_7$ | Arginine |
| $A_8$ | β-Alanine |
| $A_9$ | α-Aminoisobutyric Acid |
| $A_{10}$ | Lysyl-β-alanine |
| $A_{11}$ | Valine |
| $A_{12}$ | Leucine |
| $A_{13}$ | Isoleucine |
| $A_{14}$ | Proline |
| $A_{15}$ | Serine |
| $A_{16}$ | Threonine |
| $A_{17}$ | Cysteine |
| $A_{18}$ | Aspartic Acid |
| $A_{19}$ | Morpholine-1-acetic acid |
| $A_{20}$ | 4-Methyl-1-piperazineacetic acid |
| $A_{21}$ | β-Alanine-(2-aminopropionic) acid |
| $A_{22}$ | 3-Aminobutyric acid |
| $A_{23}$ | 2-Dimethylaminopropionic acid |
| $A_{24}$ | N-(3-dimethylaminoethyl) succinamic acid; $HO_2CCH_2CH_2CONHCH_2CH_2N(CH_3)_2$ |
| $A_{25}$ | N-(3-Butanoic acid)-2,6-diaminohexanamide |
| $A_{26}$ | 3-Dimethylaminobenzoic acid |
| $A_{27}$ | 3-Guanadinopropionic acid |
| $A_{28}$ | $HO_2CCH_2CH_2CONHCH_2CH_2SO_3H$ |
| $A_{29}$ | $HO_2CCH_2CH_2SO_3H$ |
| $A_{30}$ | $HO_2CCH_2CH_2PO_3H_2$ |

It will be understood that where the acid in the above equation has one of the formulas shown in Table 2, a carboxyl group of the acid is esterified with a hydroxyl group of the indolocarbazole of Formula I, and the remainder of the acid molecule (a residue of formula $A_1$–$A_{30}$ of Table 2) provides the solubilizing group of the resulting ester.

Ester preparation is carried out by standard methods including those set forth in detail below. Carbamate esters of the invention may be prepared by reaction of an appropriate HO—Q with an isocyanate. The preparation of isocyanates is by standard techniques. See March, J., Advanced Organic Chemistry, 3rd Edition, Wiley, N.Y. 1985.

In preferred embodiments, substituent Y is a single bond which is attached to —L—C(═O)—A or X is $CH_2$—B where B is a single bond attached to —L—C(═O)—A. In other preferred embodiments, —L—C(═O)—A may be attached to one of substituent $R^2$, $R^3$, $R^5$, $W^1$ or $W^2$.

Preferred solubilizing groups (A) possess one or more functional groupings which aid in solubilization of the indolocarbazole ester. Suitable functional groups include acidic or basic functionalities, and polyethers such as poly (ethylene glycol) carboxylic acid, with acidic or basic functionalities being preferred. Particularly preferred as solubilizing groups are residues of amino acids, particularly α-amino acids, residues of dipeptides, or derivatives thereof such as N,N-dimethylglycine. Other preferred solubilizing groups include those having one of the formulas $—(CH_2)_mZ$, $—(CH_2)_mC(=O)NH(CH_2)_mZ$, $—(CH_2)_mZ(CH_2)_mZ$, branched $—(CH_2)_nCH[(CH_2)_mZ]_2$, $—(CH_2)_n—A^1$, $—(CH_2)_n$-heteroaryl, or $—NH(CH_2)_mN(CH_3)_2$, wherein n is an integer from 0 to 5, m is an integer from 1 to 6, $A^1$ is aryl of heteroaryl substituted with one to three substituents of formula $—(CH_2)_nZ$, and Z is a basic group such as, for example, amino, or $—NR^{20}R^{21}$ where $R^{20}$ and $R^{21}$, independently, are lower alkyl of 1 to 6 carbons or 2-hydroxyethyl, or wherein $R^{20}$ and $R^{21}$ are combined together to form $—CH_2CH_2MCH_2CH_2—$ wherein M is $—CH_2—$, —S—, —O—, or $—N(R^{11})—$ wherein $R^{11}$ is a defined above. Preferably, Z can also be $—C(=NH)NH_2$, a cyclic amidine such as, for example 2-imidazolidyl, $—NHC(NH_2)=NR^{11}$, a cyclic guanidine, such as, for example, 2-(2-aminoimidazolidyl), or an acidic group, such as, for example $CO_2H$, $PO_2H$, $PO_3H_2$, $SO_3H_2$, tetrazolyl, an amino acid residue, or $SO_2NHR^{11}$. Where the solubilizing group is $—(CH_2)_n—A^1$, Z is preferably $—(CH_2)_n$-3-dimethylaminomethyl.

As used herein, the term "lower" when applied to a class of substituent means having from 1 to 6 carbon atoms. Thus, the term lower alkyl means straight-chain or branched alkyl groups having from 1 to 6 carbon atoms, such as methyl, ethyl, propyl, isopropyl, butyl, isobutyl, sec-butyl, tert-butyl, pentyl, neopentyl and hexyl. The term "lower alkoxymethyl" denotes alkoxymethyl having from 1 to 6 carbon atoms.

Halogens include fluorine, chlorine, bromine and iodine. As used herein the term "heterocycle" means a cyclic structure in which one or more constituent atoms are other than carbon, preferably N, O, S. Examples of heterocycle groups include pyrrolyl, pyranyl, thiopyranyl, pyridyl, thiazolyl, triazinyl, indolyl, purinyl, and benzothiazolyl. In some preferred embodiments of the compounds of the invention heterocycles are pyridines, pyrimidines, quinolines, isoquinolines or imidazoles.

As used herein the term "aryl" is intended to denote monocyclic and polycyclic aromatic groups including, for example, phenyl, naphthyl, xylyl, pyrrole, and furyl groups. Although aryl groups (e.g., imidazo groups) can include as few as 3 carbon atoms, preferred aryl groups have 6 to about 14 carbon atoms, more preferably 6 to about 10 carbon atoms. As used herein, the term "heteroaryl" means an aryl moiety which contains at least one basic nitrogen atom and 0 to 4 heteroatoms selected from O, S and N.

Substituent groups of the indolocarbazole esters of the invention may be further substituted. For example, where $R^5$ is lower alkylamino the lower alkyl group may be further substituted with hydroxyl. Where $R^{10}$ is phenyl, the phenyl group may be substituted by hydroxyl or amino.

Functional groups present on the indolocarbazole esters may contain protecting groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. One such protecting group is the benzyloxycarbonyl (Cbz) group. Other preferred protecting groups according to the invention may be found in Greene, T. W. and Wuts, P. G. M., "*Protective Groups in Organic Synthesis*" 2d. Ed., Wiley & Sons, 1991.

As used herein, the term "amino acid" denotes a molecule containing both an amino group and a carboxyl group. As used herein the term "α-amino acid" has its usual meaning as a carboxylic acid which bears an amino functionality on the carbon adjacent to the carboxyl group; i.e., a structure of general formula $CH(COOH)(NH_2)$-(sidechain). α-Amino acids and the residues derived therefrom, useful in the compounds of the invention, can be naturally occurring or non-naturally occurring. Representative α-amino acid sidechains are shown below on Table 3. "Dipeptides" are defined herein as two amino acids which are joined in a peptide linkage. Thus, constituents of dipeptides are not limited to α-amino acids, and can be any molecule containing both an amino group and a carboxyl group.

TABLE 3

| | |
|---|---|
| $CH_3$— | $CH_3$—$CH_2$—S—$CH_2$—$CH_2$— |
| HO—$CH_2$— | HO—$CH_2$—$CH_2$— |
| $C_6H_5$—$CH_2$— | $CH_3$—$CH_2$(OH)— |
| HO—$C_6H_4$—$CH_2$— | $HO_2C$—$CH_2$—NHC(=O)—$CH_2$— |
| 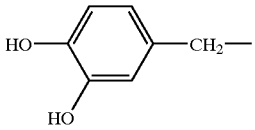 | 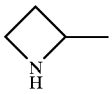 |
| 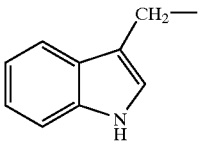 | $HCO_2$—$CH_2$—$CH_2$— |
| | $NH_2C$(=O)—$CH_2$—$CH_2$— |
| | $(CH_3)_2$—CH — |
| | $(CH_3)_2$—CH—$CH_2$— |
| | $CH_3$—$CH_2$—$CH_2$— |
| | $H_2N$—$CH_2$—$CH_2$—$CH_2$— |
| 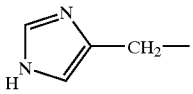 | $H_2N$—C(NH)—NH—$CH_2$—$CH_2$—$CH_2$— |
| | $H_2N$—C(=O)—NH—$CH_2$—$CH_2$—$CH_2$— |
| | $CH_3$—$CH_2$—CH($CH_3$)— |
| HS—$CH_2$— | $CH_3$—$CH_2$—$CH_2$—$CH_2$— |
| $HO_2C$—CH($NH_2$)—$CH_2$—S—S—$CH_2$— | $H_2N$—$CH_2$—$CH_2$—$CH_2$—$CH_2$— |
| $CH_3$—$CH_2$— | |
| $CH_3$—S—$CH_2$—$CH_2$— | |

Some preferred substituent groups for the compounds of the invention include residues of α-amino acids ("α-amino acid residues") or residues of dipeptides ("dipeptide residues"). For example, certain preferred substituents of indolocarbazole esters includes residues of α-amino acids after removal of the α-amino group, or the carboxylate [hydrogen] *group*. α-Amino acid residues suitable for use in the compounds of the invention include those having amino, carboxyl, imidazolyl, or other functional moieties, optionally protected with protecting or masking groups.

The invention features a method of treating a pathological condition of the prostate gland in a patient, preferably a mammal. The method involves administering to the patient a therapeutically effective amount of an indolocarbazole ester of formula Q—L—C(=O)—A, especially wherein Q is selected from residues of formulas in Table 1, particularly I-5, and A is selected from residues of one of the formulas $A_1$–$A_{10}$ in Table 2, with $A_5$ and $A_{10}$ being more preferred and $A_{10}$ being especially preferred. In some preferred embodiments, the pathological condition of the prostate gland is benign prostatic hypertrophy or prostate cancer. Other cancerous conditions may benefit from the use of the indolocarbazole esters. The anti-tumor activity of the compounds of the invention may be conveniently be assayed by a variety of in vitro or in vivo tumor assays available in the art. For example, with respect to prostate cancer, screening can be accomplished using rats innoculated with rat prostate cancer Dunning R-3327 AT-2.1 cells (see Example 20, infra).

The esters of the invention, either alone or in combination with neurotrophic factors such as NGF, are useful as therapeutics for neurological diseases, especially those diseases characterized either by neuronal cells which are injured, compromised, undergoing axonal degeneration, or at increased risk of dying, or by impaired cholinergic activity. The neurological activity of the compounds of the invention may conveniently be assayed by a cultured spinal cord choline acetyltransferase (CHAT) assay which is described in detail below, and in International Publication WO 94/02488.

The indolocarbazole esters of the invention possess improved solubility in aqueous media compared with the indolocarbazoles known in the art. Thus, the soluble indolocarbazole esters are particularly useful in pharmaceutical formulations for parenteral administration to a mammal. The stability of solutions of selected esters of the invention is described in more detail below. While not wishing to be bound by any theory, it is believed that the indolocarbazole esters of the invention undergo hydrolysis in vivo to produce free indolocarbazoles.

Pharmaceutically-acceptable salts of the indolocarbazole esters also fall within the scope of the compounds as disclosed herein. The term "pharmaceutically-acceptable salts" as used herein means an inorganic acid addition salt such as hydrochloride, sulfate, and phosphate, or an organic acid addition salt such as acetate, maleate, fumarate, tartrate, and citrate. Examples of pharmaceutically-acceptable metal salts are alkali metal salts such as sodium salt and potassium salt, alkaline earth metal salts such as magnesium salt and calcium salt, aluminum salt, and zinc salt. Examples of pharmaceutically-acceptable ammonium salts are ammonium salt and tetramethylammonium salt. Examples of pharmaceutically-acceptable organic amine addition salts are salts with morpholine and piperidine. Examples of pharmaceutically-acceptable amino acid addition salts are salts with lysine, glycine, and phenylalanine.

Compounds provided herein can be formulated into pharmaceutical compositions by admixture with pharmaceutically-acceptable nontoxic excipients and carriers. As noted above, such compositions may be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, trans-dermal patches; or prepared in other suitable fashions for these and other forms of administration as will be apparent to those skilled in the art.

The composition may conveniently be administered in unit dosage form and may be prepared by any of the methods well known in the pharmaceutical art, for example, as described in Remington's Pharmaceutical Sciences (Mack Pub. Co., Easton, Pa., 1980). Formulations for parenteral administration may contain as common excipients sterile water or saline, polyalkylene glycols such as polyethylene glycol, oils of vegetable origin, hydrogenated naphthalenes, buffered solutions and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Preferred are acetate buffered solutions. Formulations for transdermal patches are preferably lipophilic emulsions.

The materials of this invention can be employed as the sole active agent in a pharmaceutical or can be used in combination with other active ingredients, e.g., other growth factors which could facilitate neuronal survival or axonal regeneration in diseases.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution containing about 0.1 to 33% w/v compound for parenteral administration. Typical dose ranges are from about 1 $\mu$g/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the disease, the overall health status of the particular patient, the relative biological efficacy of the compound selected, and formulation of the compound excipient, and its route of administration.

The present invention is further described in the following examples. These examples are for illustrative purposes only, and are not to be construed as limiting the appended claims.

EXAMPLE 1A

Preparation of Indolocarbazole I-5

Preparation of the indolocarbazole set forth in Table 1 as I-5 (hereinafter "compound I-5") may be carried out in two steps, as follows:

1) Alkylation of indolocarbazole K-252a (Formula I wherein $R^1$, $R^2$, $R^3$, $R^4$, $W^1$ and $W^2$=hydrogen, Y=hydroxyl, and X=methoxycarbonyl) with methyl iodode and sodium hydride in DMF to give the corresponding compound wherein Y=methoxyl is described in U.S. Pat. No. 4,877,776 (Reference Example 1).
2) Reduction of the compound of Step-1 with sodium borohydride in tetrahydrouran gives compound I-5 wherein X=$CH_2OH$ and Y=methoxyl (See U.S. Pat. No. 4,877,776 for preparation of a related hydroxymethyl compound (Example 6)).

EXAMPLE 1B (I-5)-Lysinate Dihydrochloride

Step-1: To a solution of compound I-5 (900 mg, 2.0 mmol.) in dry THF (60 mL) under a nitrogen atmosphere was added dicyclohexylcarbodiimide (DCC) (422 mg, 2.05 mmol.) in one portion. Stirring was continued for 15 minutes at room temperature, then Boc-lysine(Box)-OH (727 mg, 2.1 mmol.) and dimethylaminopyridine (DMAP) (25 mg) were added and the solution was stirred 24 hours. The mixture was filtered through a pad of diatomaceous earth (Celite®) then concentrated at reduced pressure. The product was purified by column chromatography (silica gel; EtOAc; hex; 2:1; $R_f$=0.3) to give 1.25 g (82%) of a white solid, mp 140°–146° C. (EtOAc, hexane), $^1$H NMR (DMSO-$d_6$) δ1.4 (s, 9H, tBu), 1.45 (s, 9H, tBu), Anal.calc. for $C_{43}H_{51}N_5O_9$.0.75 $H_2O$: C, 64.93, H, 6.65, N, 8.81. Found: C, 65.03, H, 6.76, N, 8.61.

Step-2: The product from Example 1, step 1 (650 mg, 0.85 mmol) in EtOAc (50 mL) was treated with an EtOAc-HCl (g) solution dropwise. The solution warmed to 40°–50° C. for 15 minutes then cooled to −20° C. The material which precipitated was collected to give 470 mg (90%) of the product as a white solid (MeOH, EtOAc), mp 245° C. (dec.), MS m/z=582 $(M+1)^+$, Anal.calc. for $C_{33}H_{34}N_5O_5$.2HCl 1.5 $H_2O$: C, 58.15, H, 5.92, N, 10.27. Found: C, 58.45, H, 5.81, N, 10.31.

EXAMPLE 2

(I-5)-Glycinate Hydrochloride

The subject ester was prepared by the same general procedure as Example 1, step 1 using Compound I-5 (300 mg, 0.66 mmol) and N-Boc-glycine (128 mg, 0.73 mmol) to give 375 mg (93%) of N-Boc-amino ester as a white solid, mp 305° C. dec. (EtOAc-hexane), TLC (silica gel, EtOAc: hex; 2:1) Rf=0.3., $^1$H NMR (DMSO-$d_6$) δ1.38 (s, 9H, tBu), MS m/z=611 $(M+1)^+$. Treatment of the product from Example-2 step-1 (300 mg, 0.492 mmol) with EtOAc-HCl (g) gave 230 mg (92%) of the product as a white solid, mp 275° C. (dec.), MS m/z=511 $(M+1)^+$.

EXAMPLE 3

(I-5)-Alaninate Hydrochloride

The subject ester was prepared by the same procedure as Example 1, step 1 using Compound I-5 (300 mg, 0.66 mmol) and Boc-alanine (138 mg, 0.73 mmol) to give 375 mg (91%) as a white solid, mp>250° C. dec. (EtOAc-hexane), TLC (silica gel, EtOAc: hex; 2:1) Rf=0.3., $^1$H NMR (DMSO-$d_6$) δ1.4 (s, 9H, tBu), MS m/z=623 $(M+1)^+$.

Treatment of the product from Example 3 step 1 (100 mg, 0.19 mmol) with EtOAc-HCl (g) gave 65 mg (65%) of ester as a white solid, mp 220° C. (dec.), MS m/z=526 $(M+1)^+$.

EXAMPLE 4

(I-5)-Hydrogen Succinate

A mixture of Compound I-5 (300 mg, 0.66 mmol.), succinic anhydride (73 mg, 0.73 mmol) and DMAP (25 mg) in toluene was maintained at reflux for 24 hours. The mixture was cooled to room temperature and the solid precipitate was collected by filtration, then triturated with MeOH and recollected. The product was recrystallized from THF-MeOH to give 320 mg (89%) of ester as a white solid, mp 271°–273° C., $^1$H NMR (DMSO-$d_6$) δ2.63 (m, 2H, $CH_2CO_2H$), 2.74 (m, 2H, $CH_2CO$), 12.4 (s, 1H, COOH), MS m/z=553 (M+).

EXAMPLE 5

(I-5)-Pyridine-3-carboxylate Hydrochloride

To a mixture of Compound I-5 (300 mg, 0.66 mmol) and DCC (260 mg, 1.26 mmol) in $CH_2Cl_2$ (50 mL) were added pyridine-3-carboxylic acid (160 mg, 1.26 mmol) and DMAP (25 mg). The solution was stirred 36 hours under nitrogen at ambient temperature then filtered through a pad of Celite®. $CH_2Cl_2$ (150 mL) was added to the filtrate and it was extracted with water (2×100 mL), NaCl solution (1×150 mL) dried ($MgSO_4$), then concentrated under reduced pressure. The resulting solid was dissolve in EtOAc (40 mL) and filtered. The EtOAc solution was treated with an EtOAc-HCl (g) solution and cooled to −20° C. The product was collected to give 325 mg (83%) of a yellow solid ester, mp 200°–201° C. (dec.) (THF-$Et_2O$), $^1$H NMR (DMSO-$d_6$) δ7.22–7.4 (m, 3H), 7.45–7.52 (m, 2H), 7.78–7.85 (m, 2H), 7.96 (d, 1H, J=8 Hz), 8.96 (d, 1H, J=8 Hz), 8.62 (m, 1H), 8.68 (s, 1H), 8.97 (d, 1H, J=7.5 Hz), 9.22 (d, 1H, J=8 Hz), 9.33 (s, 1H), MS m/z=559 $(M+1)^+$

EXAMPLE 6

(I-5)-Pyridine-3-carboxylate Methiodide

A solution of the product of Example 5 (100 mg, 0.18 mmol) and $CH_3I$ (3 mL) in acetone (25 mL) was maintained at reflux for 1 h. The solvent was concentrated to approximately half the volume at reduced pressure and EtOAc (20 mL) was added. The product was collected to give 100 mg (80%) of ester as a yellow solid, mp>230°–232° C., $^1$H NMR (DMSO-$d_6$) δ3.4 (s, 3H, $CH_3N$), 7.2–7.4 (m, 3H), 7.42–7.55 (m, 3H), 7.8 (d, 1H, J=8 Hz), 7.98 (d, 1H, J=8 Hz), 8.05 (d, 1H, J=8 Hz), 8.35–8.4 (m, 1H), 8.65 (s, 1H), 9.1 (d, 1H), 9.2–9.3 (m, 2H), 9.6 (s, 1H), MS m/z=702 $(M+1)^+$.

EXAMPLE 7

(I-5)-N,N-Dimethylglycinate Hydrochloride

A mixture of Compound I-5 (300 mg, 0.66 mmol) and dicyclohexylcarbodiimide (270 mg, 1.32 mmol) in $CH_2Cl_2$ (50 mL) was stirred under nitrogen for 15 minutes N,N-Dimethylglycine (135 mg, 1.32 mmol) and DMAP (25 mg) were added and the mixture was stirred 36 hours at ambient temperature. The mixture was filtered, $CH_2Cl_2$ (150 mL) was added and the solution was extracted with water (2×200 mL) and dried ($MgSO_4$). The solvent was removed under reduced pressure, and the resulting solid was dissolved in EtOAc (25 mL) and filtered. EtOAc-HCl (g) was added dropwise and the product collected to give 310 mg (82%) of the ester as a white solid (MeOH-EtOAc), mp 216°–217° C., $^1$H NMR (DMSO-$d_6$) δ2.95 (s, 3H, NMe), 2.98 (s, 3H, NMe), 4.5 (s, 2H, $NCH_2CO$), MS m/z=539 $(M+1)^+$.

EXAMPLE 8

(I-5)-Dimethylaminobutyrate Hydrochloride

A mixture of Compound I-5 (300 mg, 0.66 mmol) and dicyclohexylcarbodiimide (270 mg, 1.32 mmol) in $CH_2Cl_2$ (50 mL) was stirred under nitrogen for 15 minutes. 3-Dimethylaminobutyric acid hydrochloride (185 mg, 1.1 mmol) and DMAP (25 mg) were added and the mixture was stirred for 12 hours at ambient temperature. The solution was filtered, $CH_2Cl_2$ (150 mL) was added and the solution was then extracted with water (2×200 mL), $NaHCO_3$ solution (5%, 2×100 mL), NaCl solution (2×100 mL) and dried ($MgSO_4$). The solution was treated with an EtOAc-HCl(g) solution dropwise and the solvent concentrated at reduced pressure. Recrystalization of the product from MeOH-ether gave 375 mg (94%) of product ester as a greenish solid, mp 182°–185° C. (dec.), $^1$H NMR (DMSO-$d_6$) δ3.6 (s, 6H, $NMe_2$), 4.6 (s, 2H, $CH_2O$), MS m/z=567 $(M+1)^+$.

EXAMPLE 9

(I-5) Histidinate Dihydrochloride

A mixture of Boc-His(Boc)-OH (506 mg, 1.42 mmol), Compound I-5 (418 mg, 0.92 mmol) and DCC (195 mg, 0.96 mmol) in $CH_2Cl_2$/DMF (1:1, 2.4 mL) was stirred 12 hours at ambient temperature. The reaction mixture was diluted with ethyl acetate (25 mL) and filtered. The ethyl acetate layer was washed with a 2% $NaHCO_3$ solution (2×20 mL), saturated NaCl solution (1×20 mL) and dried ($MgSO_4$). Petroleum ether was added and a yellowish-green precipitate was collected. Purification by column chromatography (silica gel; EtOAc; Rf=0.4) gave 154 mg, (38%) of the Boc-Histidine(Boc) ester as a white solid. $^1$H NMR (DMSO-$d_6$) δ1.35 (s, 9H, tBu), 1.48 (s, 9H, tBu). A solution of the product from Example-9 step-1 (144 mg) in EtOAc (2 mL) was added 4N HCl in dioxane (6 mL). The mixture was stirred for 2 h at room temperature, diluted with water (30 mL) and extracted with EtOAc (1×30 mL) and ether (1×30 mL). The aqueous layer was lyophilized to give a solid product ester (105 mg, 86%), mp 228° C. (dec.), MS m/z=592 $(M+1)^+$.

EXAMPLE 10

(I-5)-Argininate Dihydrochloride

This compound was prepared by the same general procedure as Example 9 using Compound I-5 (250 mg, 0.55 mmol), Boc-Arginine(Boc)-OH (380 mg, 1.01 mmol) and DCC (120 mg, 0.59 mmol) in $CH_2Cl_2$/DMF (1:1, 1.2 mL) to give 256 mg (56%) of a crude (I-5)-BOC-arginine(Boc) ester. This compound (210 mg, 0.3 mmol) was stirred in a mixture of EtOAc (4 mL) and 4N HCl in dioxane (8 mL) for 2 h at room temperature. The precipitate was collected and stirred for 1 h with 20 mL of 1N HCl. The filtrate was lyophilized to give 47 mg (23%) of the product ester as a solid, mp 271° C. (dec.), MS m/z=611 $(M+1)^+$.

EXAMPLE 11

(I-5)-β-Alaninate Hydrochloride

This compound was prepared by the same general procedure as Example 9 using Compound I-5 (200 mg, 0.44 mmol), Boc-β-alanine (203 mg, 1.0 mmol), DMAP (40 mg) and DCC (202 mg, 1.0 mmol) in $CH_2Cl_2$/DMF (1:1, 5 mL) to give 256 mg (91%) of (I-5)-Boc-β-alanine ester, mp 141 (dec.), $^1$H NMR (DMSO-$d_6$) δ1.38 (s, 9H, tBoc). This compound (250 mg, 0.4 mmol) was treated with HCl to give 172 mg (77%) of the product ester as a solid, mp 279° C. (dec.), MS m/z=525 $(M+1)^+$.

EXAMPLE 12

(I-5)-α-Aminoisobutyrate Hydrochloride

This compound was prepared by the same general procedure as Example 9 using Compound I-5 (200 mg, 0.44 mmol), Boc-aminoisobutyric acid (203 mg, 1.0 mmol), DMAP (50 mg) and DCC (202 mg, 1.0 mmol) in $CH_2Cl_2$/DMF (1:1, 4 mL) to give 260 mg (93%) of (I-5)-Boc-aminoisobutyric acid ester. This compound (250 mg, 0.4 mmol) was treated with HCl to give 170 mg (74%) of the product ester as a solid, mp 214° C. (dec.), MS m/z=539 $(M+1)^+$.

EXAMPLE 13

(I-5)-Glutamate Hydrochloride

This compound was prepared by the same general procedure as Example 9 using Compound I-5 (200 mg, 0.44 mmol), Boc-glu(tBu)-OH (303 mg, 1.0 mmol), DMAP (40 mg) and DCC (202 mg, 1.0 mmol) in $CH_2Cl_2$/DMF (1:1, 4 mL) to give the Boc-ester, mp 170° C. dec. This compound was treated with HCl to give 180 mg (66%) of the product ester as a solid, mp 235° C. (dec.), MS m/z=583 $(M+1)^+$.

EXAMPLE 14

(I-5)-Lysyl-β-Alaninate Dihydrochloride

Method A: To a mixture of Compound I-5 (2.26 g, 5.0 mmol) in $CH_2Cl_2$ (100 mL) were added Boc-Lys(Boc)-β-Ala-OH (1.83 g, 5.5 mmol), DCC (2.06 g, 10.0 mmol) and DMAP (100 mg). The solution was stirred under nitrogen at ambient temperature for 4 hours, then filtered, and the solvent was concentrated at reduced pressure to give a solid, mp 160–165° C. EtOAc (250 mL) was added to the resulting solid and the mixture was filtered. HCl(g) was added to pH 3 and the solution was heated to 60° C., then allowed to cool to room temperature for 1 hour. The precipitate was collected, washed with EtOAc followed by $Et_2O$ and dried under vacuum (40° C., 48 hours) to give 2.65 g (73%) of the product ester as a pale yellow solid, mp 205° C. (dec.) MS m/z=653 $(M+1)^+$. MS m/z=653 $(M+1)^+$.

Method B: A mixture of the ester of Example 11 (57 mg, 0.1 mmol), Boc-Lys(Boc)-OH dicyclohexylamine salt (114 mg, 0.21 mmol), BOP (88 mg, 0.2 mmol), HOBt (30 mg, 0.2 mmol) and N-methylmorpholine (0.11 mL, 1 mmol) in DMF (2 mL) was stirred for 3 hours. The mixture was diluted with 15 mL of EtOAc and extracted with water, $NaHCO_3$ solution and citric acid solution. The solvent was dried ($MgSO_4$) and concentrated to give 82 mg (94%) of a green solid. This material (100 mg, 0.13 mmol) was treated with EtOAc-4N HCl in dioxane to give 54 mg (75%) of the product ester as a solid, MS m/z=653 $(M+1)^+$.

EXAMPLE 15

Effect of Indolocarbazole Esters on ChAT Activity

The effect of indolocarbazole esters of the invention on ChAT activity was assayed in dissociated spinal cord cultures prepared from fetal rats. ChAT is the enzyme that catalyzes the synthesis of the neurotransmitter acetylcholine, and it is a specific biochemical marker for cholinergic neurons. In the spinal cord, the large majority of cholinergic neurons are motor neurons. Assay of this enzyme may thus be used as an indication of the effects of a factor (or factors) on the survival and/or differentiation of cholinergic neurons and/or regulation of this enzyme. The procedure used for the assay is that described in Example 6 of WO 94/02488. Fourteen esters were tested in the spinal cord ChAT assay to determine their relative efficacy, and the results are summarized in Table 4.

TABLE 4

Effect of Compounds on ChAT Activity in Spinal Cord Cultures

| Compound | Spinal Cord ChAT Activity (% of Control) | |
|---|---|---|
| Example | 500 nM | 1000 nM |
| 1 | 150 | 153 |
| 2 | 157 | 151 |
| 3 | 151 | 132 |
| 4 | 150 | 154 |
| 5* | 137 | 139 |
| 6 | 149 | 150 |
| 7 | 132 | 151 |
| 8 | inactive | 138 |
| 9 | 158 | 143 |
| 10 | 128 | 170 |
| 11 | 138 | 149 |
| 12 | 155 | 150 |
| 13 | 168 | 142 |
| 14 | 121 | 147 |

*This compound increases ChAT activity 169% over control at 10 μM

EXAMPLE 16

Stability of the Esters in Buffered Solution

Our requirements for a useful intravenous dosing solution were set at a concentration of an indolocarbazole ester of at least 1 mg/ml, with less than 1% conversion to indolocarbazole I-5 (compound I-5) over 24 hours. The esters are preferably soluble in buffer solutions most applicable to mammalian administration. The most preferred esters (Examples 8 and 14) have a low rate of conversion to indolocarbazole I-50. Indolocarbazole esters were dissolved in water, dimethylsulfoxide (DMSO) and the following buffer solutions to determine solubility and to observe conversion to indolocarbazole I-5. Samples were analyzed by HPLC using UV detection at 290 nm. The following examples describe the procedures used for preparation of the buffers, dissolution of the indolocarbazole esters therein, and analysis of solution stability after 24 hours.

A. Preparation of Buffer solutions

Buffer solutions were prepared as follows:

Solution 1 was water.

Solution 2 was a 10 mM acetate buffer at pH 4 which was prepared by weighing 0.68 g of sodium acetate $3H_2O$ into 500 ml of water and adjusting the pH with acetic acid.

Solution 3 was a 10 mM phosphate buffer, pH 7, which was prepared by weighing 0.30 g of monobasic sodium phosphate and 0.36 g of dibasic sodium phosphate into 500 ml of water, stirring until completely dissolved, and adjusting the pH with hydrochloric acid.

Solution 4 was a 10 mM Tris buffer, pH 9, which was prepared by weighing 0.79 g of Tris (tris (hydroxymethyl)aminomethane hydrochloride) into 500 ml of water, stirring until completely dissolved, and adjusting the pH with sodium hydroxide.

Solution 5 was a DMSO control. None of the indolocarbazole esters tested showed conversion to I-5 in DMSO.

B. Preparation of Samples

Sample solutions were prepared by weighing 0.5–1 mg of the indolocarbazole ester into an amber 1.5 ml autosampler vial, to which the appropriate quantity of one of the buffer solutions was added, in order to achieve a final concentration of 1 mg/ml. The sample solutions were vortexed and sonicated for 10 minutes. Fifty μl aliquots were placed into 1.5 ml amber autosampler vials. The reaction was quenched at a selected time interval by addition of 450 μl DMSO to the vial. The diluted sample solutions were then analyzed by reverse-phase HPLC (Hewlett Packard 1050 series). HPLC conditions were as follows:

| Step | Time (minutes) | % A | % B | % C | Conditions |
|---|---|---|---|---|---|
| 1 | 15 | 70 | 20 | 10 | Equilibration |
| 2 | 15 | 40 | 50 | 10 | Achieved Linearly |
| 3 | 5 | 40 | 50 | 10 | |
| 4 | 5 | 10 | 80 | 10 | Wash |

A = 0.1% TFA, water
B = 0.1% TFA, acetonitrile
C = methanol
Wavelength: 290 nm
Flow rate: 1 ml/min
Injection volume: 10 μl
Column: Zorbax Rx C18 4.6 × 250 mm, 5μ particle size, 300 Å pore size
Column temperature: 30° C.

The results of the initial screening are shown in FIG. 1. The pH of the compounds in water varied from 2 to 5 while the buffers remained approximately the same at 3.6, 6.7 and 7.8 for the 10 mM acetate, phosphate and Tris, respectively. (FIG. 1 shows the appearance of indolocarbazole I-5 after 24 hours.). These data show that the acetate buffer is preferred for minimum hydrolysis.

In regard to our criteria for indolocarbazole ester stolidity 1 mg/ml, the following information is noted. In preparing the sample solutions, it was noted that certain of the esters were not completely soluble in all of the buffers, and some insoluble residue remained undissolved. The results shown in FIG. 1 were obtained with the solution portion of these preparations. For example, the esters of Examples 1B, 2 and 14 appeared completely soluble in all of the solutions tested. The ester of Example 10 appeared to be completely soluble in water, and in the acetate and Tris buffers, but was not completely soluble in the phosphate buffer. The esters of Examples 3, 7, 8, 9, 11 and 12 appeared to be completely soluble in water and in the acetate buffer, but they were not completely soluble in the Tris buffer and phosphate buffer. The esters of Examples 4, 5, 6 and 13 were not completely soluble in water, nor in any of the buffers tested. Although it is preferred that the indolocarbazole esters of the invention be completely soluble in each of the solutions tested, indolocarbazole ester which are not completely soluble in one or more of the solutions may nevertheless possess advantageous utilities.

Figure 2:
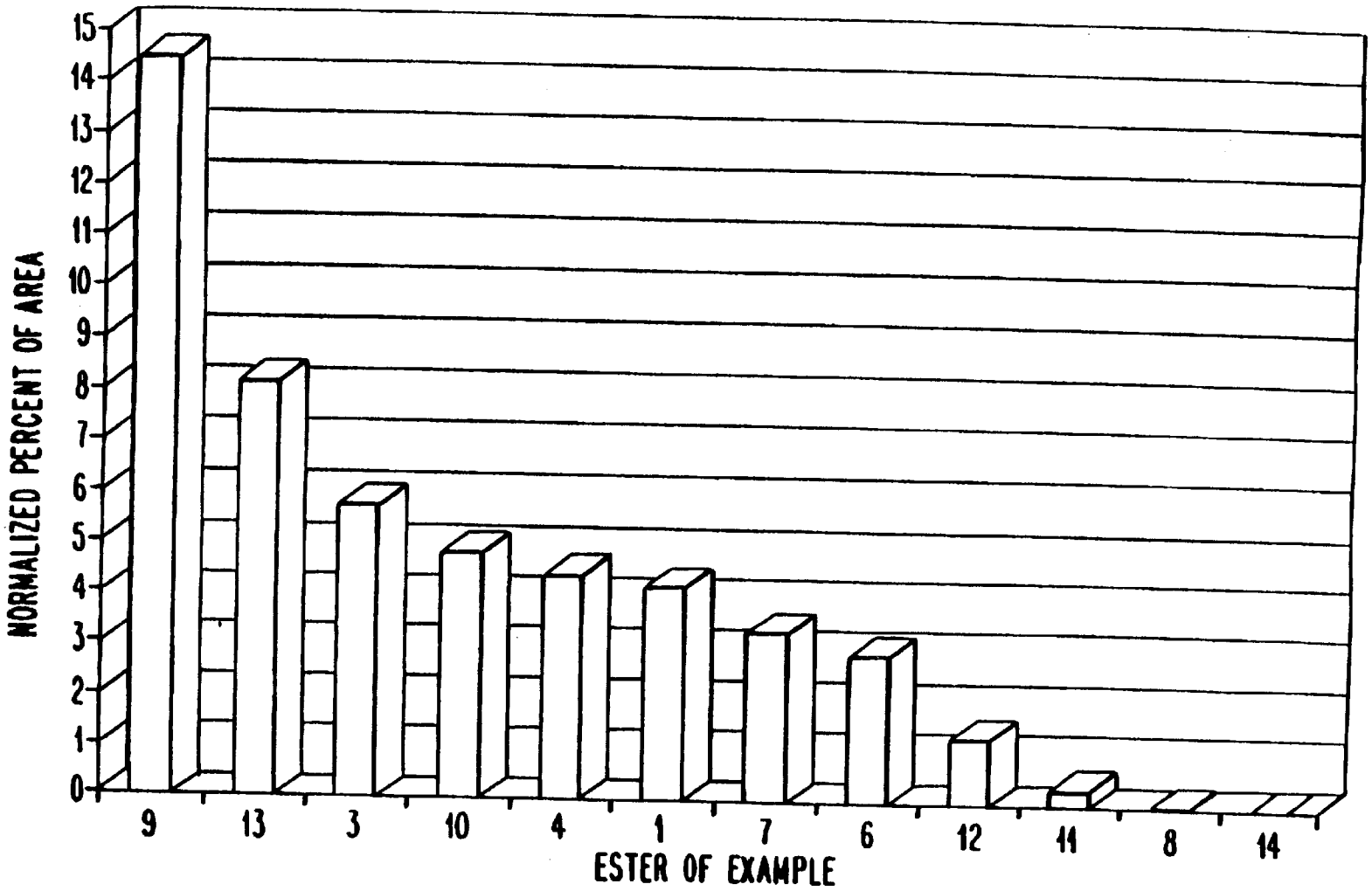
FIG. 2 shows stability of indolocarbazole esters of the invention in 10 mM acetate buffer, pH 3.6.
Figure 3:
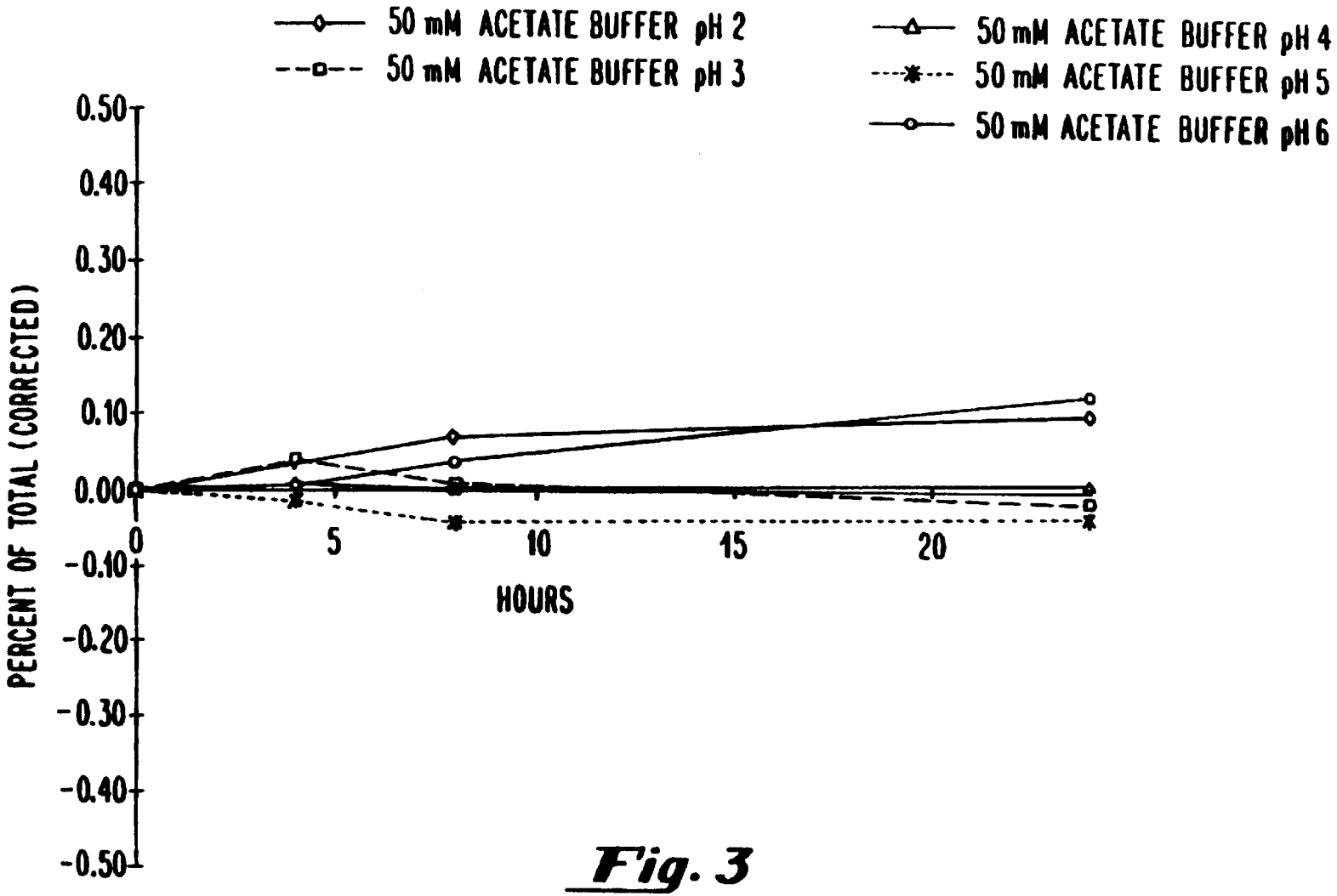
FIGS. 3, 4 and 5 show the rates of conversion to I-5 as a function of pH for the esters of Examples 14, 8, and 11, respectively.
Figure 4:
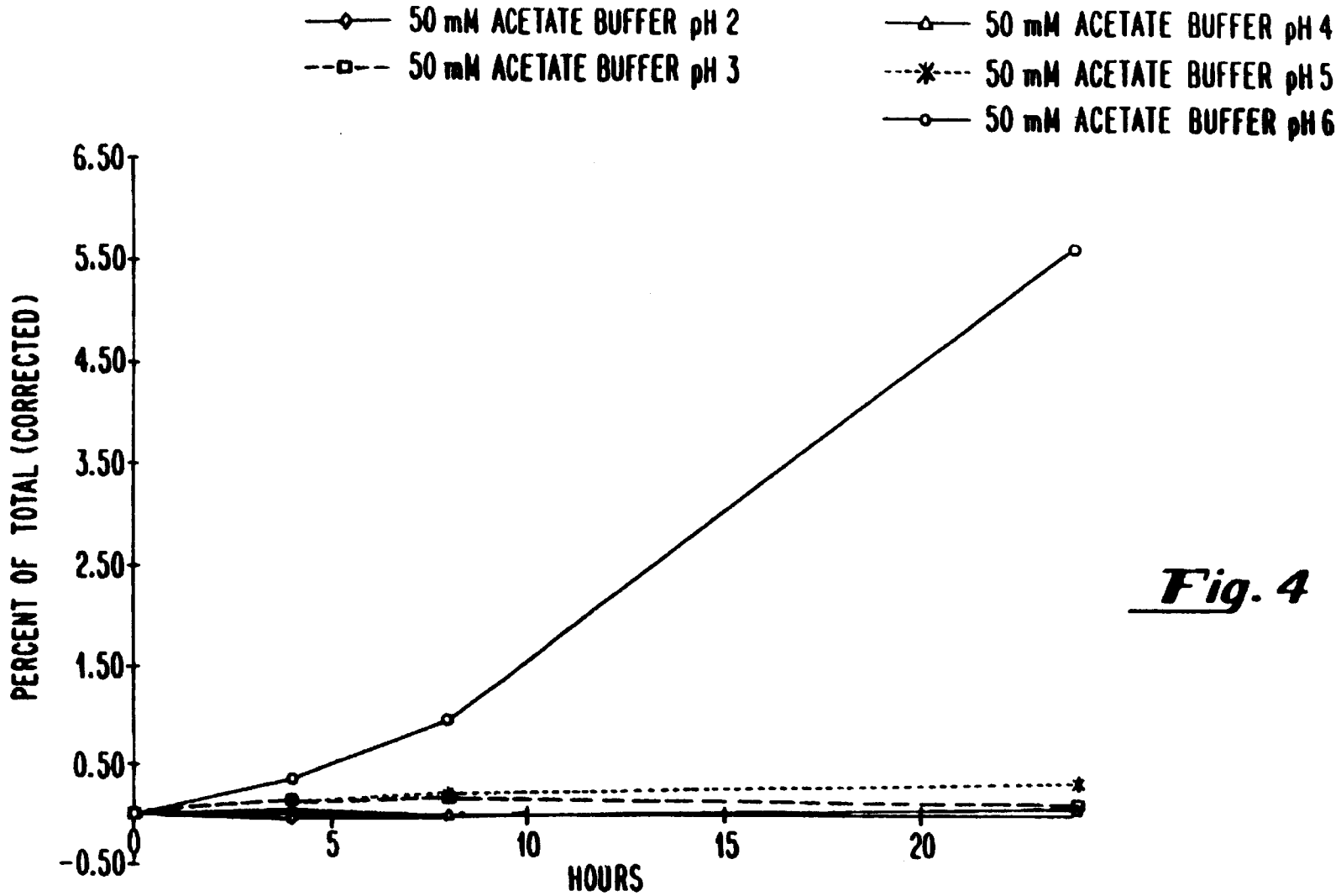
Figure 5:
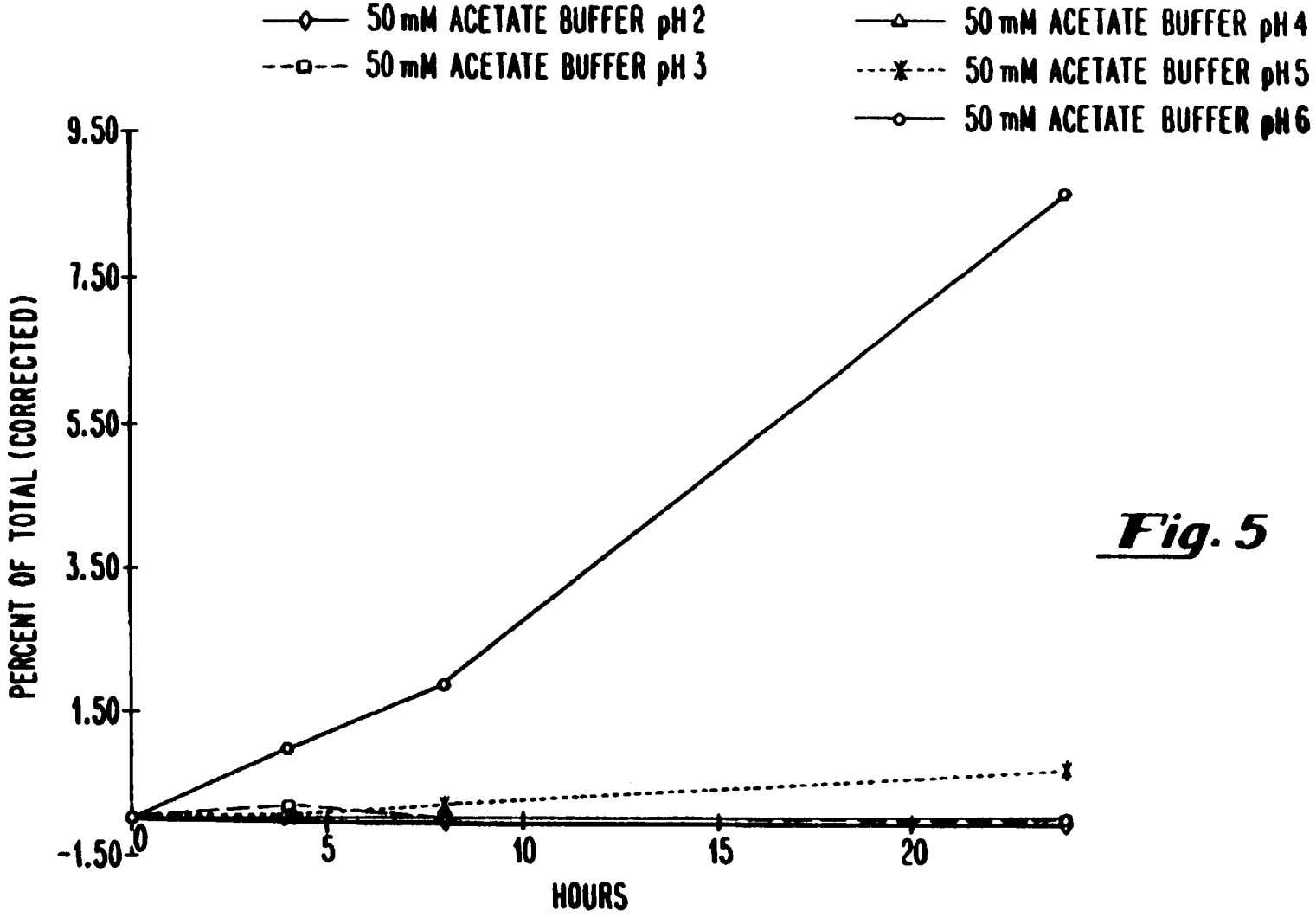

A "pH profile" was generated for the indolocarbazole esters that showed the greatest stability in the acetate buffer from initial screening (FIG. 2, which shows the appearance of indolocarbazole I-5 after 24 hours). Acetate buffers at pH 2, 3, 4, 5 and 6 were prepared as follows. A total of 6.8 g of sodium acetate trihydrate was added to one liter of water, and the mixture was stirred until the solid was completely dissolved. One hundred ml aliquots were placed into 150 ml Erlenmeyer flasks, and the pH values were adjusted with HCl to pH 2, 3, 4, 5, and 6. A concentration of 50 mM was chosen to reduce the effects of compound addition. The indolocarbazole ester of Example 14 was investigated only with the acetate buffers. The rates of conversion of I-5 (the appearance of indolocarbazole I-5) as a function of pH are shown in FIGS. 3, 4, and 5 for the indolocarbazole esters of Examples 14, 8, and 11, respectively.

EXAMPLE 17

In Vitro Metabolism of Indolocarbazole I-5 Esters in Rat and Human Plasma and Liver S-9 Fractions Mammalian body fluids and tissues contain a diverse number of nonspecific esterases that can hydrolyze ester linkages in xenobiotics. These enzymes appear to have overlapping selectivities and variable activities depending on the species and are found both in the cytosol and microsomes. Cytosolic esterases are typically associated with a specific reaction, whereas the microsomal-associated esterases metabolize a large number of xenobiotic esters. Therefore, incubation of xenobiotics possessing an ester linkage within various biological matrices, such as plasma, tissue cytosol, and tissue microsomes, can be used to predict the availability of a drug in vivo and to rapidly determine the extent of hydrolysis in each matrix.

Freshly-collected plasma from male Sprague-Dawley rats and presumably-healthy drug-free male humans was pooled and immediately frozen. The plasma was kept frozen at −90° C. and each aliquot was thawed only once for use in incubations. Stock solutions of the indolocarbazole esters were prepared in DMSO and were used to prepare standard curves in plasma that had been boiled to two minutes. Boiled plasma was divided into 500 μL aliquots, mixed with an aliquot of the internal standard, and spiked with the respective stock indolocarbazole ester solutions to prepare the standard curve. Thawed plasma was divided into 500 μL aliquots, placed in screw-cap vials, mixed with internal standard, and spiked with stock solutions of the respective indolocarbazole esters to yield a nominal concentration of 5000 ng/mL.

Rat and human liver S-9 fractions (a mixture of cytosol and microsomes) were frozen immediately after preparation. Each aliquot was thawed once for use in incubations. Stock solutions of the indolocarbazole esters were prepared in DMSO. These were used to prepare standard curves in heat inactivated S-9 fraction that had been diluted with 0.2M phosphate buffer, pH 7.4 to yield a 2 mg/mL protein concentration. Heat inactivated S-9 was divided into 500 μL aliquots, mixed with an aliquot of the internal standard, and spiked with the respective stock ester solutions to prepare the standard curve. Incubations containing liver S-9 fraction were prepared by diluting the S-9 fraction in 0.2M phosphate buffer, pH 7.4 to yield a 2 mg/mL protein concentration. Samples (500 μL) were placed in screw-cap vials, mixed with internal standard, and spiked with stock solutions of the respective esters to yield a nominal concentration of 5000 ng/mL.

Incubations were then performed at 37° C. in a shaking water bath for 0, 0.5, 1, 2, 5, 10, 15, 30, and 60 minutes and quenched by addition of 5 mL methylene chloride. All tubes (standards and experimentals) were extracted for 15 minutes by shaking, and centrifuged. The methylene chloride layer was removed, dried under a stream of nitrogen, and reconstituted in DMSO. Fifty μL of the reconstituted extracts were analyzed by reverse-phase HPLC with detection at 290 nm. The mobile phase and gradient conditions are given below:

| Step | Time (minutes) | ACN-0.1% TFA (%) | Water-0.1% TFA (%) | Conditions |
|---|---|---|---|---|
| 1 | 10 | 20 | 80 | Equilibrium |
| 2 | 30 | 70 | 30 | Linear gradient |

Figure 6:
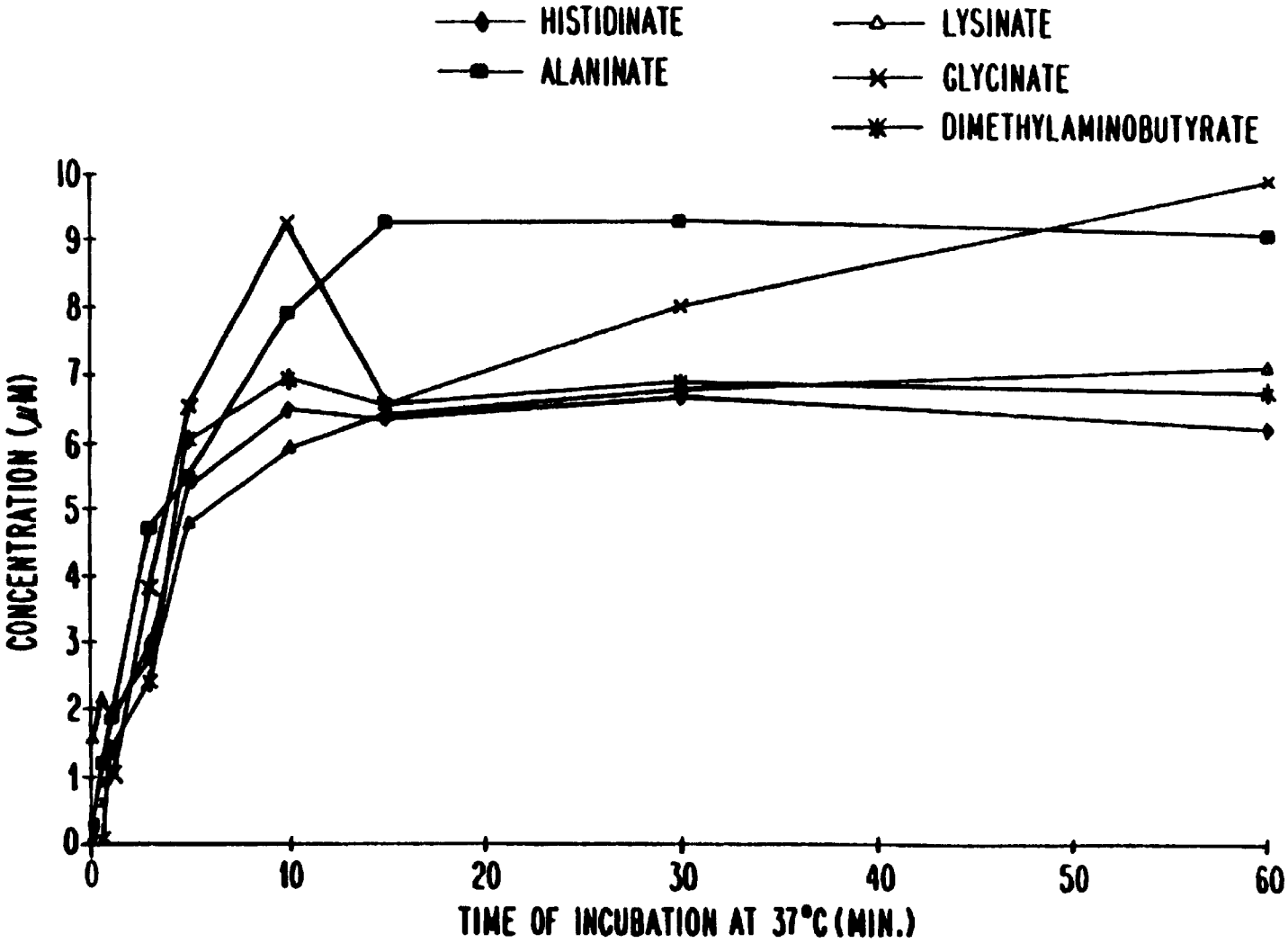
FIG. 6 shows levels of indolocarbazole I-5 in rat plasma following addition of 5000 ng/ml indolocarbazole esters.

Six different esters of indolocarbazole I-5 were incubated with rat plasma (histidinate dihydrochloride, alaninate hydrochloride, lysinate dihydrochloride, argininate dihydrochloride, glycinate hydrochloride and dimethylaminobutyrate hydrochloride). In the case of five of the indolocarbazole esters, there was rapid hydrolysis of the ester linkage resulting in the liberation of indolocarbazole I-5 (FIG. 6). The linear rate of hydrolysis of 5 out of 6 esters was similar during the first five minutes of incubation; hydrolysis of argininate was complete prior to the first sampling period. The maximum rates of hydrolysis revealed some enzyme selectivity in that alaninate hydrochloride and glycinate hydrochloride were more extensively hydrolyzed than histidinate dihydrochloride, lysinate dihydrochloride, argininate dihydrochloride, or dimethylaminobutyrate hydrochloride (DMAB).

Figure 7:
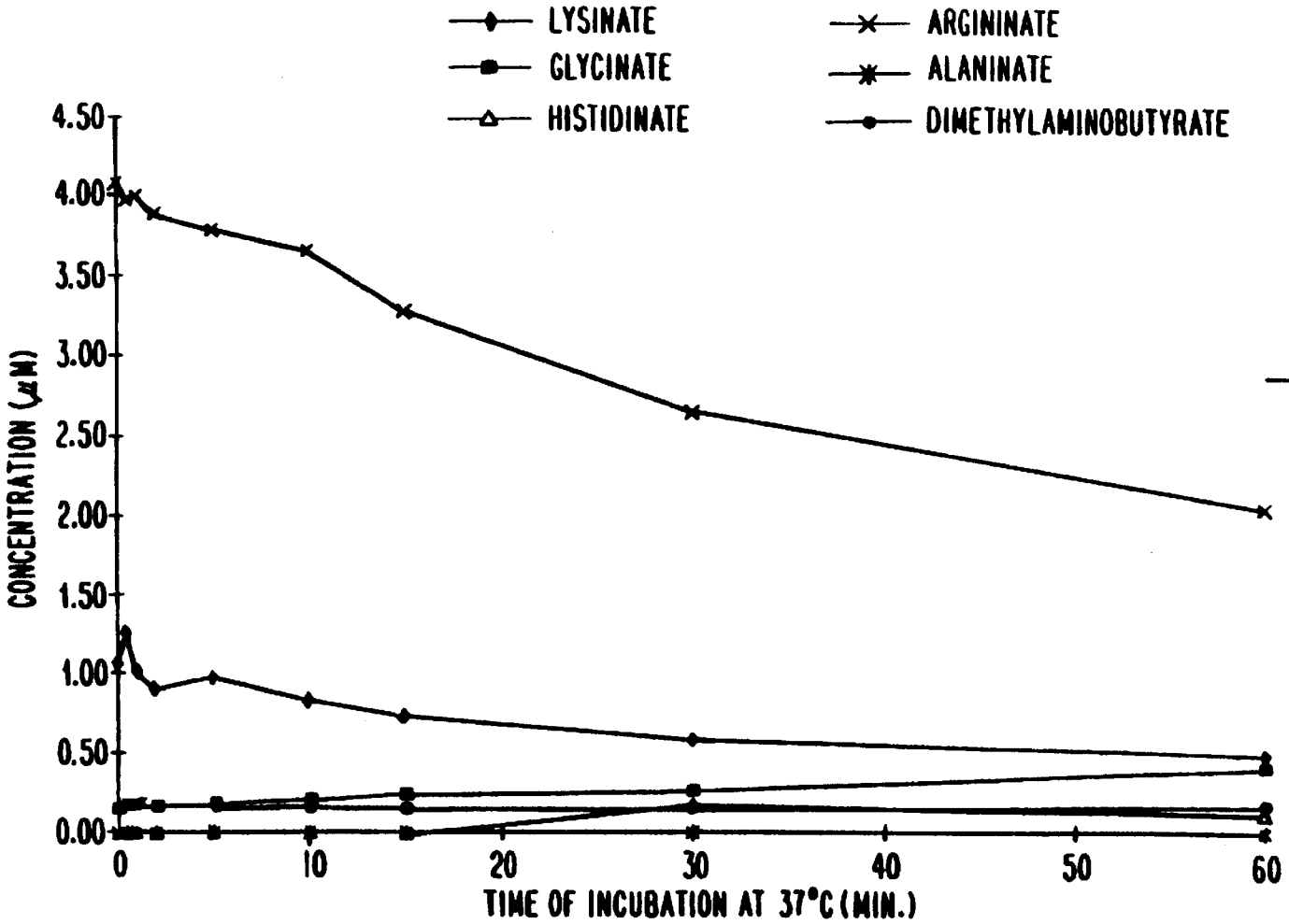
FIG. 7 shows levels of indolocarbazole I-5 in human plasma following addition of 5000 ng/ml indolocarbazole esters.

The same six esters were also incubated with human plasma. Both argininate dihydrochloride and lysinate dihydrochloride were hydrolyzed rapidly; rates of formation of indolocarbazole I-5 could not be measured because maximum amounts were detected immediately upon addition of the ester (FIG. 7). The rate of hydrolysis of alaninate hydrochloride could not be quantified because conversion to I-5 was not detectable. The rates of hydrolysis of the remaining indolocarbazole esters were measurable, but were much lower than those observed in the rat.

Figure 8:
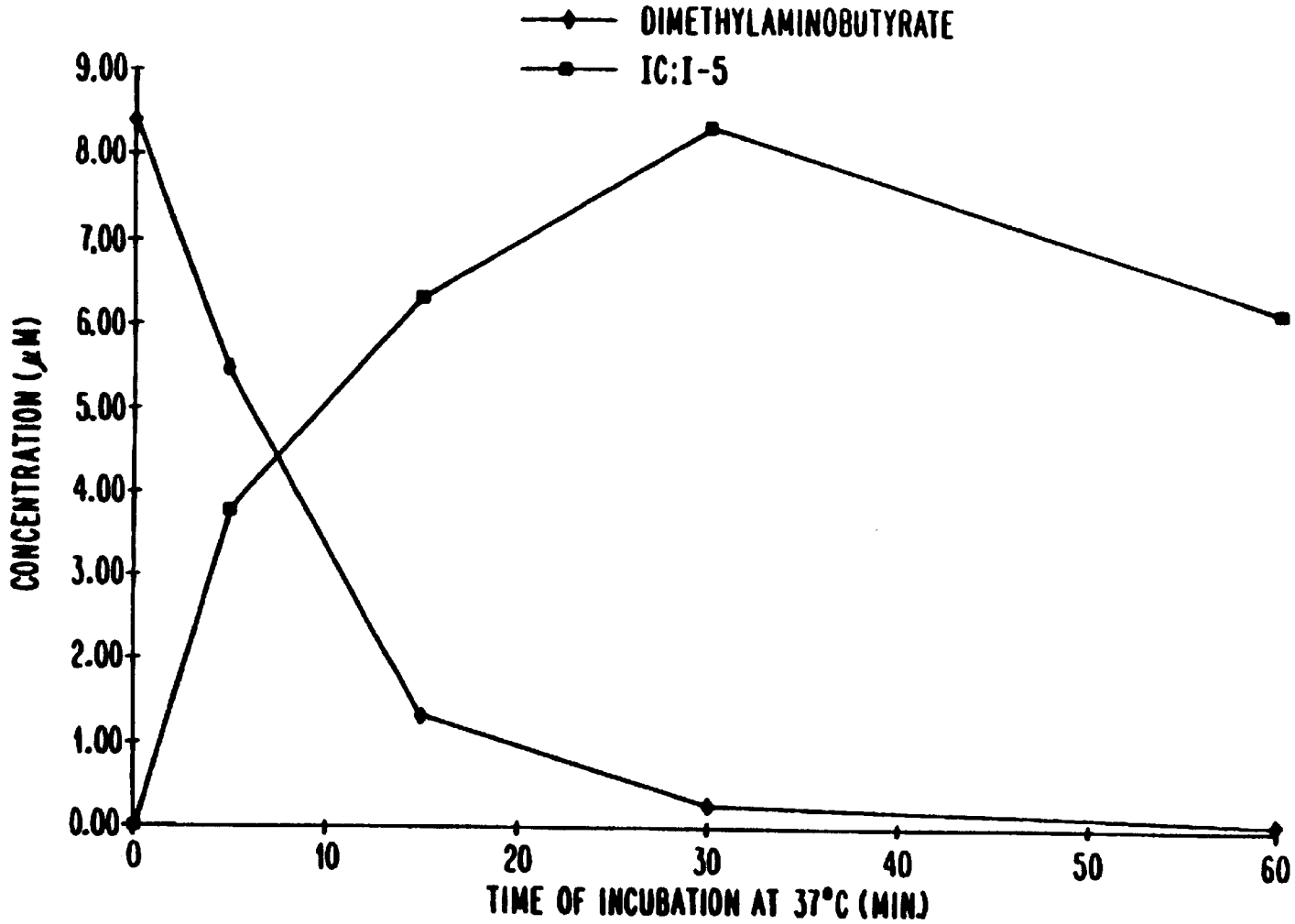
FIG. 8 shows the stability of the dimethylaminobutyrate of indolocarbazole I-5 in rat liver S-9 fraction at 2 mg/ml protein.
Figure 9:
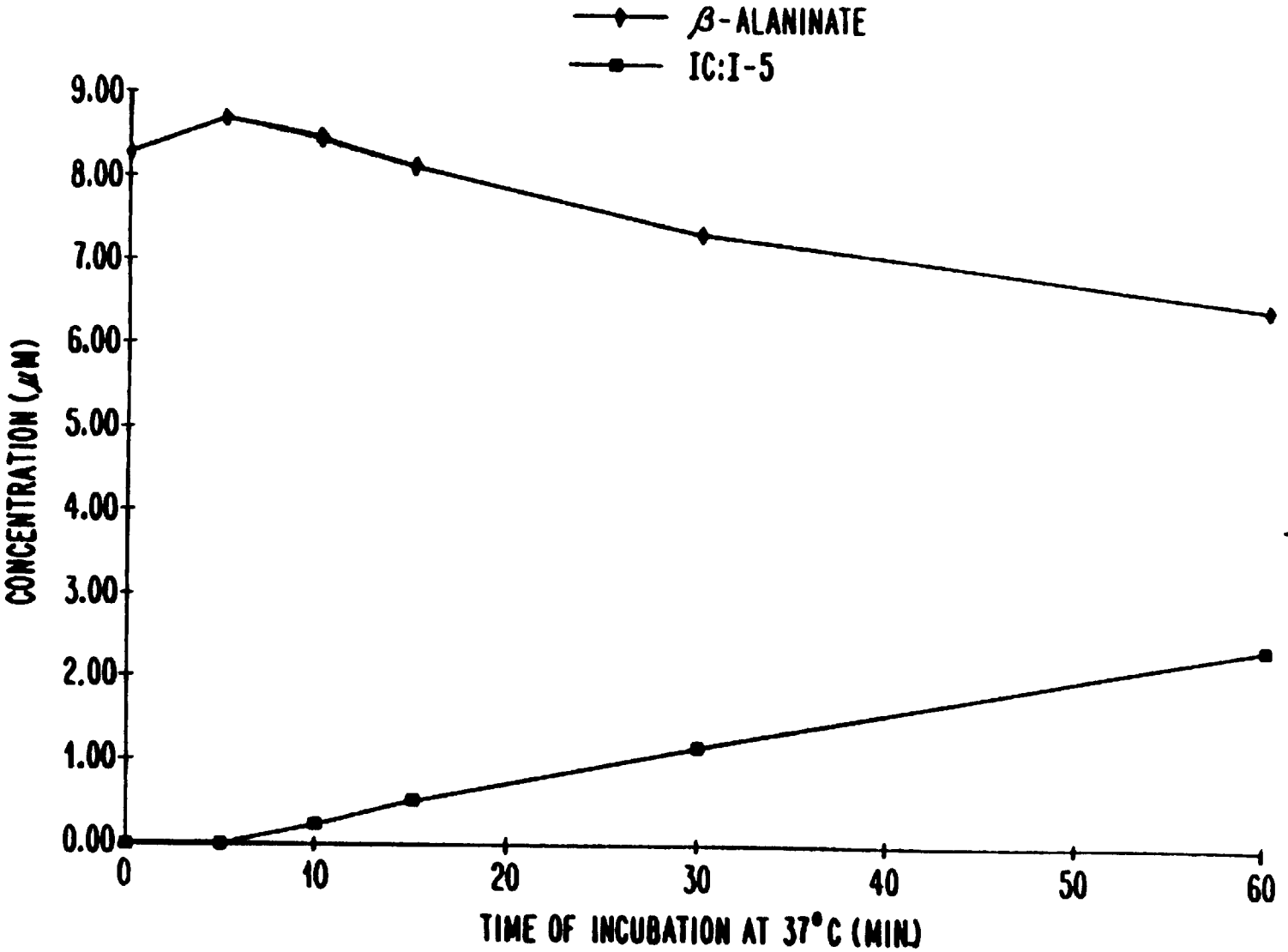
FIG. 9 shows the stability of the β-alaninate of indolocarbazole I-5 in rat liver S-9 fraction at 2 mg/ml protein.
Figure 10:
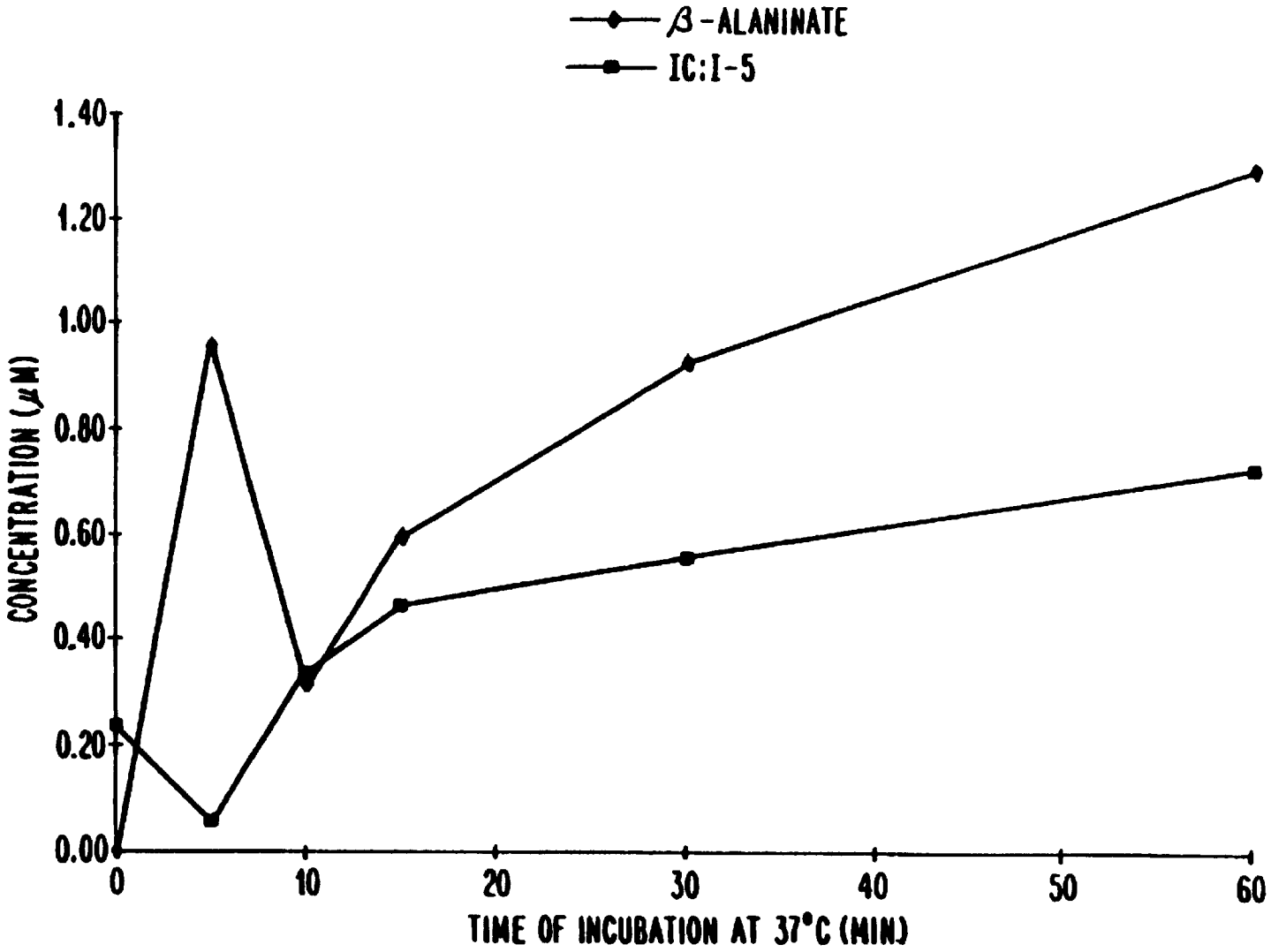
FIG. 10 shows levels of indolocarbazole I-5 and the β-alaninate of indolocarbazole I-5 in rat liver S-9 fraction at 2 mg/ml protein following addition of lysyl β-alaninate of indolocarbazole I-5.

Three indolocarbazole esters were selected for incubation with rat liver S-9 fraction. In the case of DMAB (FIG. 8), there was rapid hydrolysis of the ester resulting in a concomitant increase in indolocarbazole I-5. However, in the case of β-alaninate, the rate of hydrolysis was markedly reduced (FIG. 9). Lysyl-μ-alaninate revealed a metabolic profile unlike any of the esters previously examined. An initial hydrolysis of the amide bond between the two amino acids appears to be the first metabolic event followed by hydrolysis of the ester linkage (FIG. 10).

Figure 11:
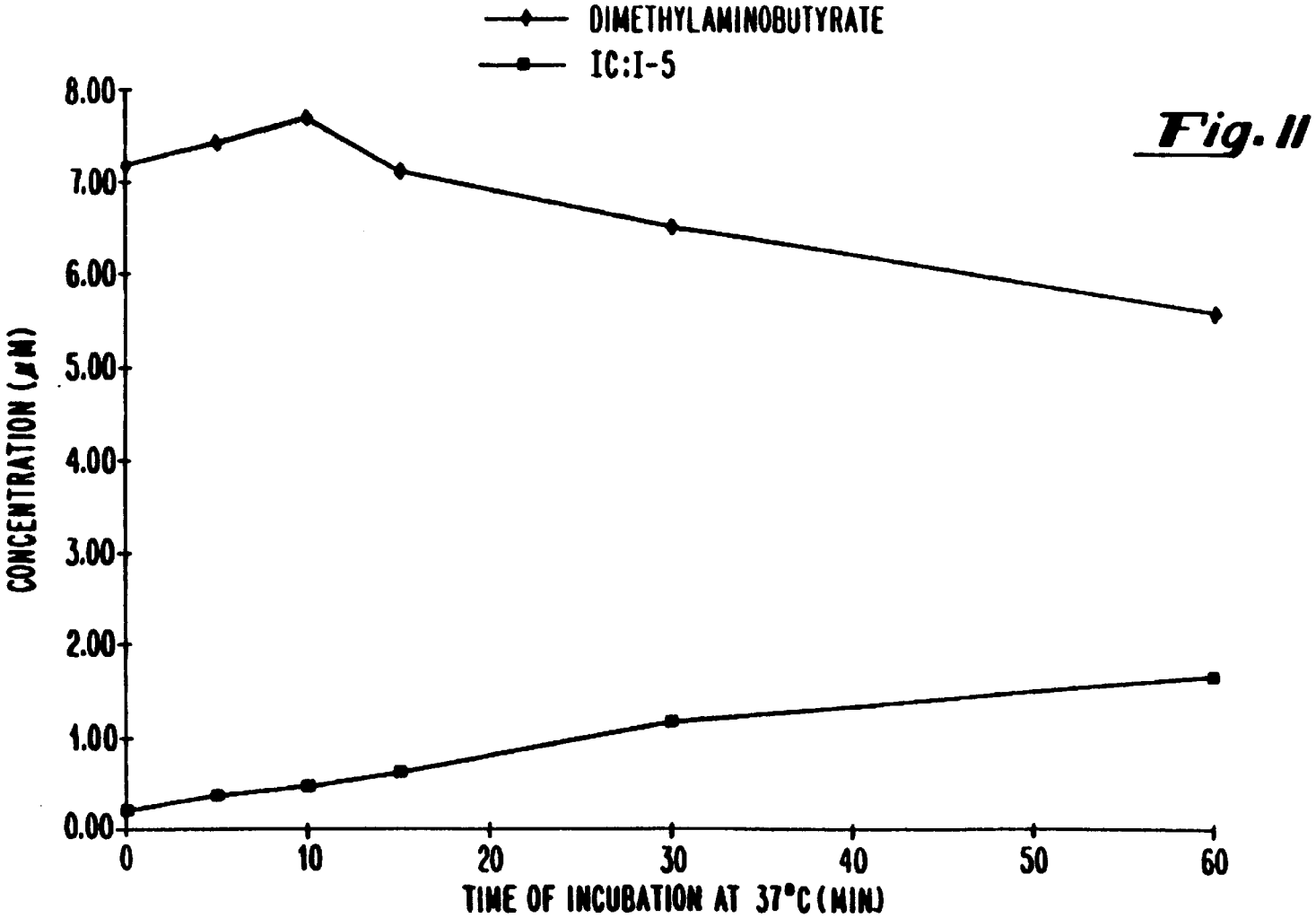
FIG. 11 shows the stability of the dimethylaminobutyrate of indolocarbazole I-5 in human liver S-9 fraction at 2 mg/ml protein.
Figure 12:
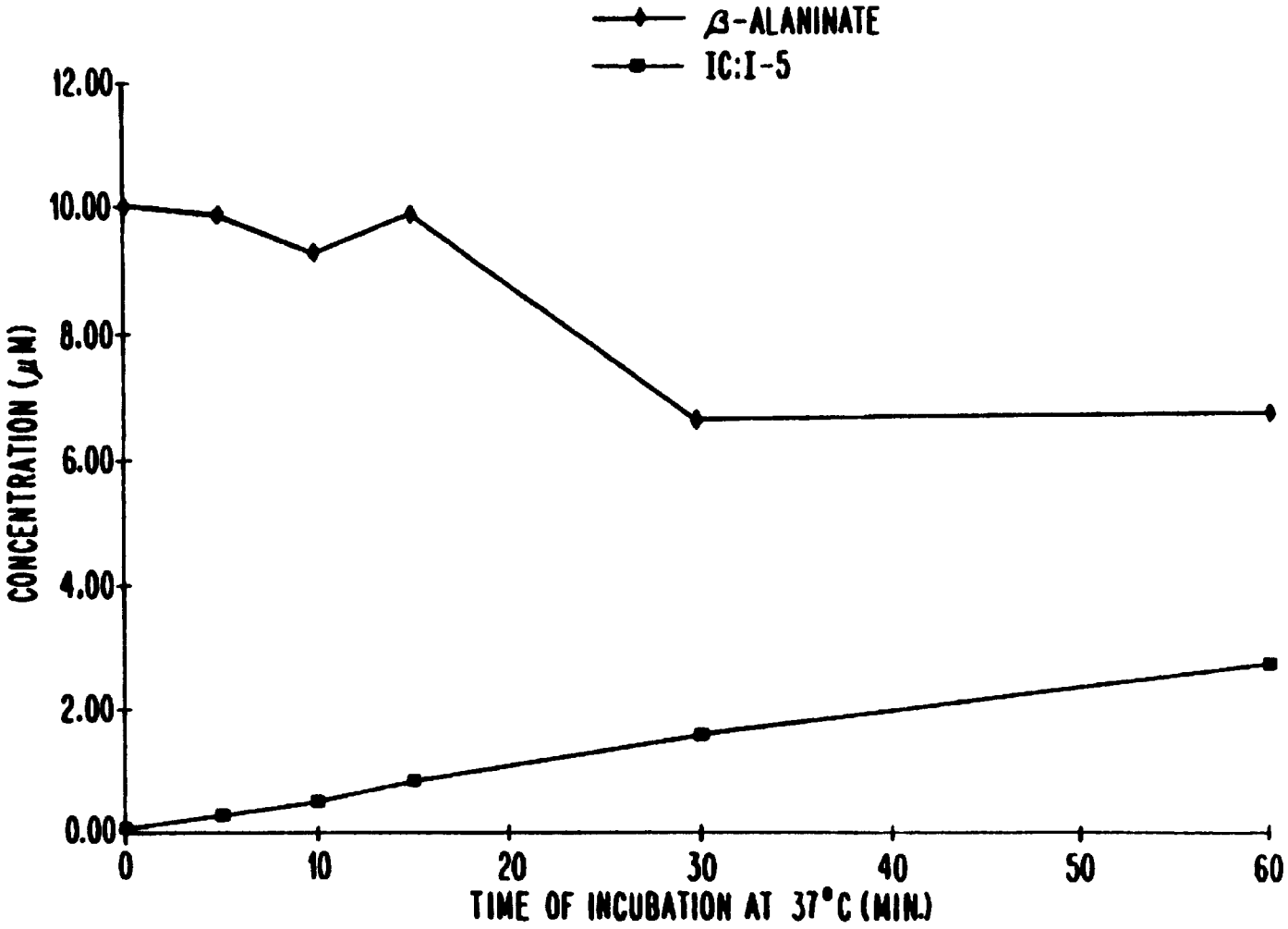
FIG. 12 shows the stability of the β-alaninate of indolocarbazole I-5 in human liver S-9 fraction at 2 mg/ml protein.

The metabolism of both DMAB and μ-alaninate was examined in similar incubations conducted with human liver S-9 fraction. The rates of hydrolysis of both indolocarbazole esters were similar (FIGS. 11 and 12).

EXAMPLE 18

In Vivo Metabolism and Pharmacokinetics of Compound I-5 Esters in Male Sprague-Dawley Rats Although in vitro incubations can yield predictive information about the types of metabolites that may be observed in vivo, as well as information regarding enzyme specificity for a candidate xenobiotic, an in vitro system is nonetheless limited in its ability to define the absorption, distribution, metabolism, and elimination of the drug following its administration to an animal model. Thus, in vivo metabolism with pharmacokinetic information for indolocarbazole esters was developed.

Groups of 12 male Sprague-Dawley rats were administered either DMAB dihydrochloride or β-alaninate hydrochloride through the lateral tail vein in a vehicle consisting of 0.05M acetate buffer, pH 5.0 containing 20% polyethylene glycol. The volume of the dosing solution was adjusted on the basis of body weight to deliver a 5 mg/kg dose of indolocarbazole I-5 after complete hydrolysis of the respective indolocarbazole ester. At 5, 30, 60, and 120 minutes after injection, the animals were anesthetized with carbon dioxide and a sample of whole blood was obtained by cardiac puncture. The blood was placed into a 10 mL heparinized tube containing 100 μL 50% potassium fluoride (an inhibitor of plasma esterases). Following centrifugation, the resulting plasma was frozen in a dry-ice/isopropanol bath and kept frozen at −90° C. prior to analysis.

For analysis, the samples were thawed, internal standard was added, and the mixture was extracted with 5 mL methylene chloride. Standards in rat plasma were prepared as described previously. All tubes (standards and experimentals) were extracted for 15 minutes by shaking, and centrifuged. The methylene chloride layer was removed, dried under a stream of nitrogen, and reconstituted in DMSO. Fifty μL of the reconstituted extracts was analyzed by reverse-phase HPLC with detection at 290 nm. The mobile phase and gradient conditions are the same as those given in Example 17.

Figure 13:
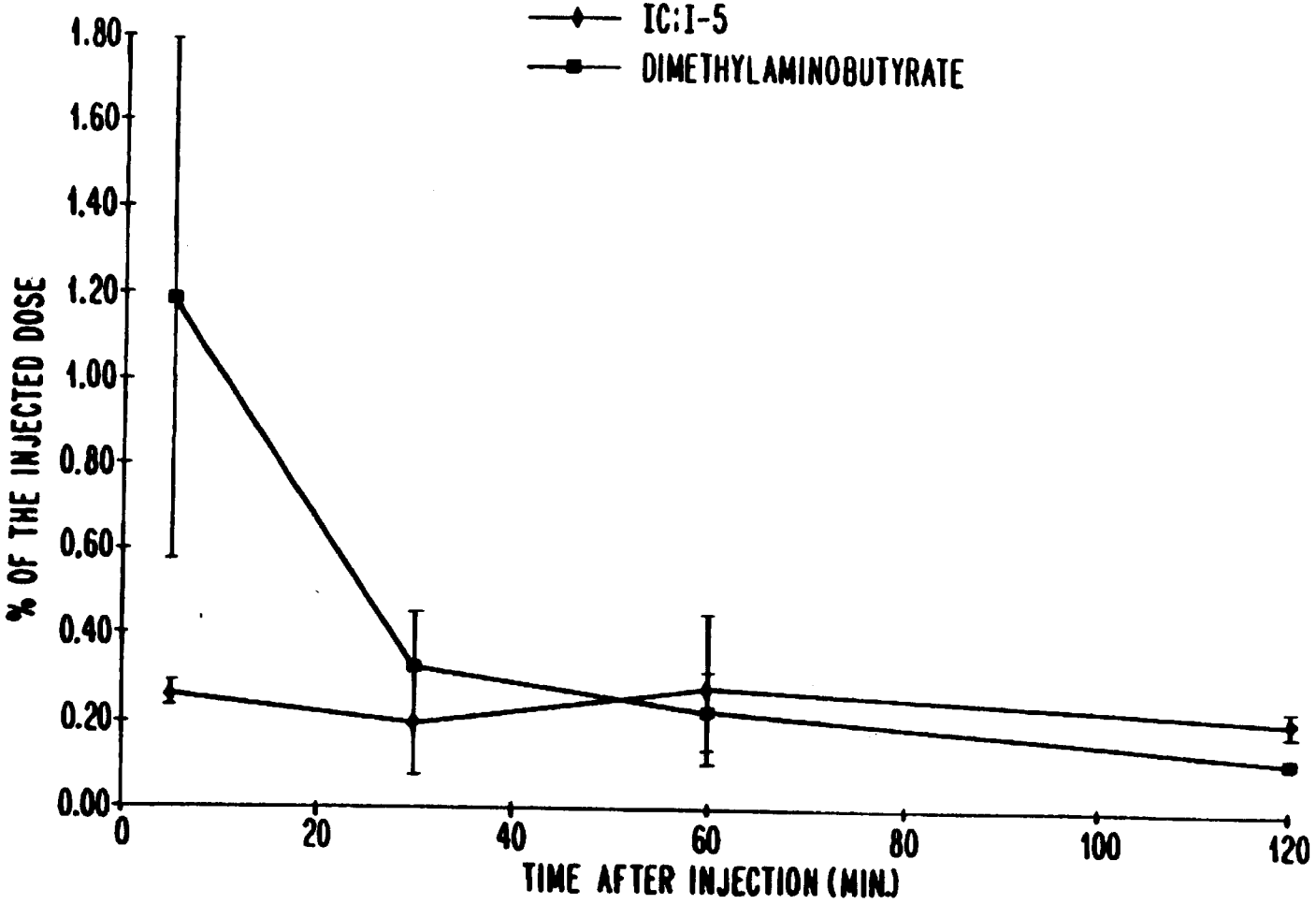
FIG. 13 shows the intravenous pharmacokinetics of the dimethylaminobutyrate of indolocarbazole I-5 in male Sprague-Dawley rats.
Figure 14:
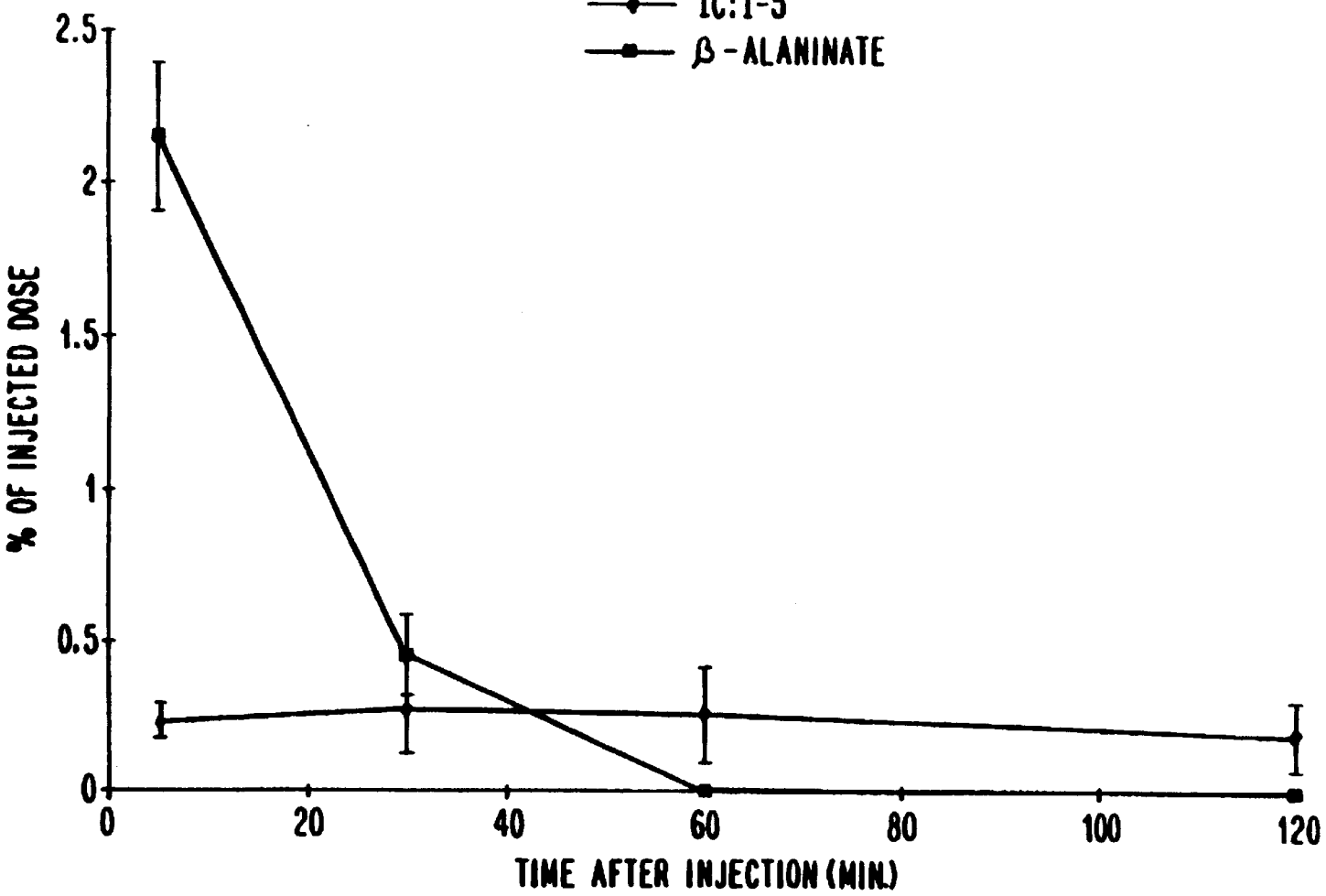
FIG. 14 shows the intravenous pharmacokinetics of the β-alaninate of indolocarbazole I-5 in male Sprague-Dawley rats.

Upon administration to groups of male Sprague-Dawley rats, both the DMAB hydrochloride and β-alaninate hydrochloride were rapidly hydrolyzed to indolocarbazole I-5 (FIGS. 13 and 14). DMAB could be detected in plasma for two hours following administration; β-alaninate could only be detected for one hour after administration. In both cases, the amount of indolocarbazole I-5 detected remained relatively constant at approximately 0.2 to 0.3% of the administered dose.

EXAMPLE 19

Route-to Route Comparison of Indolocarbazole I-5 Formation from Lysyl-β-alaninate Groups of 12 male Sprague-Dawley rats were administered lysyl-β-alaninate dihydrochloride via intravenous or subcutaneous injection, as well as by oral gavage at a dose of 8.01 mg/kg. This dose was designed to deliver a 5 mg/kg equivalent dose of indolocarbazole I-5 following complete hydrolysis of the indolocarbazole ester. The volume of the dosing solution was adjusted on the basis of body weight. At 5, 30, 60, and 120 minutes after intravenous injection and 30, 60, 120, and 240 minutes after either subcutaneous injection or oral gavage, the animals were anesthetized with carbon dioxide and a sample of whole blood was obtained by cardiac puncture. The blood was placed into a heparinized container containing 100 μL 50% potassium fluoride (an inhibitor of plasma esterases) and 10 μL phenylmethylsulfonylfluoride (an inhibitor of plasma amidase). Following centrifugation, the resulting plasma was frozen in a dry-ice/isopropanol bath and kept frozen at −90° C. prior to analysis.

For analysis, the samples were thawed, internal standard was added, and the mixture was extracted with 5 mL methylene chloride. Standards in rat plasma were prepared as described previously. All tubes (standards and experimentals) were extracted for 15 minutes by shaking, and centrifuged. The methylene chloride layer was removed, dried under a stream of nitrogen, and reconstituted in DMSO. Fifty μL of the reconstituted extracts was analyzed by reverse-phase HPLC with detection at 290 nm. The mobile phase and gradient conditions are the same as those given in Example 17.

Figure 15:
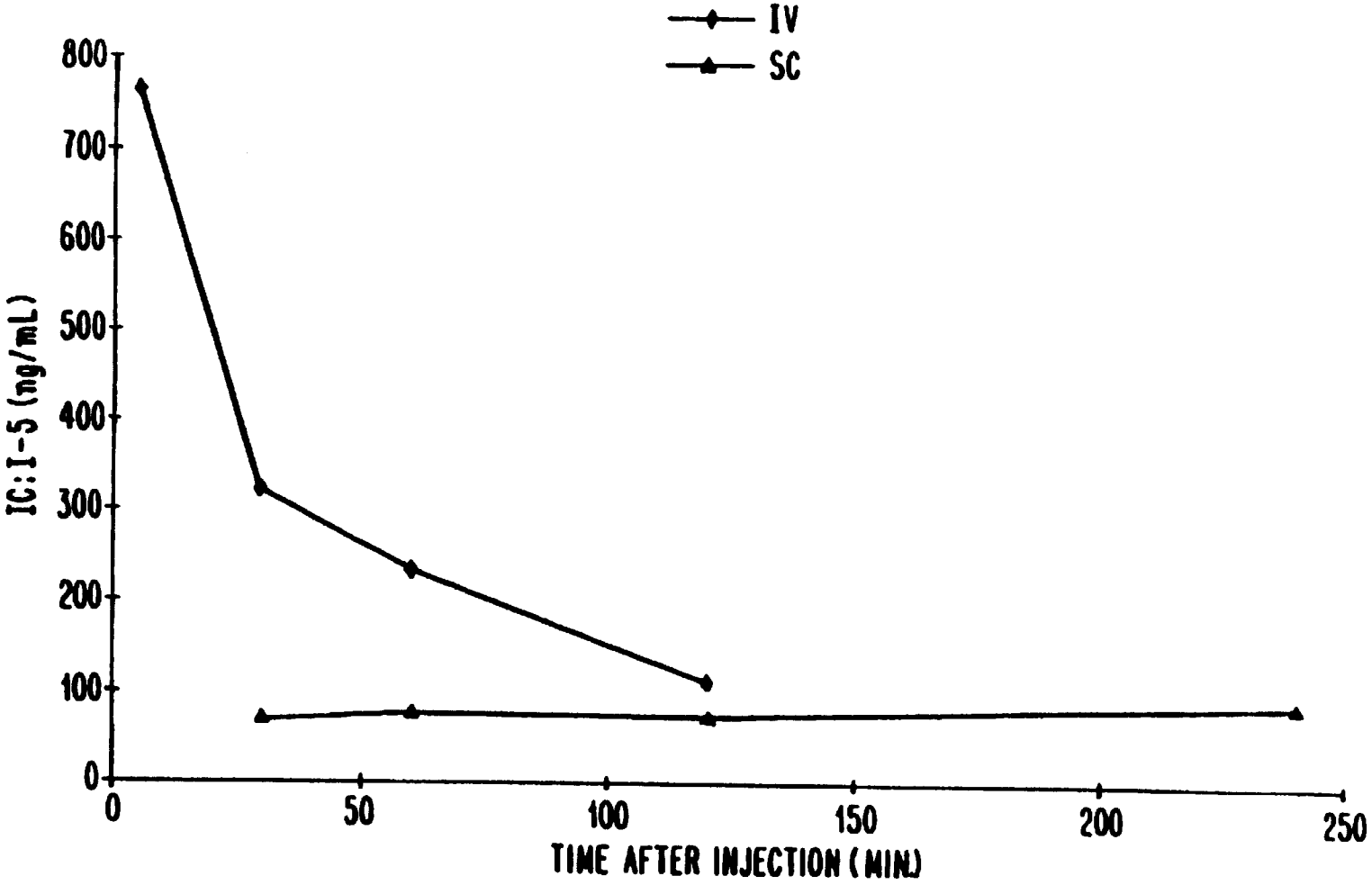
FIG. 15 shows a comparison of indolocarbazole I-5 levels in plasma after subcutaneous and intravenous dosing with the lysyl-β-alaninate of indolocarbazole I-5.

Lysyl-β-alaninate resulted in detectable levels of I-5 in plasma following dosing by both the intravenous and subcutaneous routes. Although there were detectable levels of I-5 in plasma following administration of an oral dose, the levels were below the limit of quantitation (50 ng/mL). Following intravenous administration, the plasma levels of indolocarbazole I-5 were approximately 600 ng/mL 5 minutes after dosing, with levels gradually decreasing to approximately 80 ng/mL 2 hours after dosing (FIG. 15). Subcutaneous administration of lysyl-β-alaninate dihydrochloride resulted in plasma levels of I-5 that remained relatively constant at approximately 70 ng/mL at all time points examined (FIG. 15).

Example 20

Comparison of Indolocarbazole I-5 and (I-5)-Lysyl-β-Alaninate for Anti-tumor Efficacy Against the Androgen-Independent AT-2 Rat Prostate Tumor Indolocarbazole I-5 is a potent protein tyrosine kinase inhibitor which has been demonstrated to have growth inhibitory properties against the androgen-independent Dunning R-3327 AT-2 rat prostate tumor in vivo (see WO 94/27982); given the foregoing data derived from the pharmacokinetic experiments which indicate that (I-5)-lysyl-β-alaninate is rapidly converted to I-5 in vivo, equivalent bioactivity of I-5 and its lysyl-β-alaninate ester was a possibility. Accordingly, the comparative anti-tumor efficacy of I-5 and its lysyl-β-alaninate ester in the Dunning R-3327 AT-2 tumor model were investigated.

MATERIALS AND METHODS

Cell line

Rat prostate cancer Dunning R-3327 AT-2.1 cells (Isaacs et al., Prostate 9:261–281, 1986) were grown at 37 C. in a humidified incubator, with a 95% air/5% $CO_2$ atmosphere, in RPMI-1640 medium containing 10% fetal calf serum, 250 nM dexamethasone, 2 mM glutamine, penicillin (100 I.U./mL), and streptomycin (100 μg/mL), and 1 mM sodium pyruvate. The cells were determined to be free of mycoplasma and rodent viruses (MAP testing) by Microbiological Associates. Exponentially growing cells were harvested using 6 mL of warm trypsin. The total volume was brought up to 10 mL with media to neutralize trypsin and cells were counted. The cells were then collected by brief centrifugation, and cell pellet was resuspended in Hanks' Balanced Salt Solution to achieve the final concentration of 1×107 live cells/mL.

Animals

Male inbred Copenhagen rats (200–225 g) obtained from Harlan Sprague-Dawley, Indianapolis, Ind., were maintained three rats/cage and given a commercial diet (Purina Formulab 5001) and water ad libitum. Animals were housed under humidity- and temperature-controlled conditions and light/dark cycle was set at 12-hour intervals. Rats were quarantined for one week before experimental manipulation.

Tumor cell implantation and growth

Fifty adult male Copenhagen rats were inoculated with live AT-2 cells (1×106 cells/rat) into their right flank. Seven days later, rats bearing AT-2 tumors (approximately 0.5 . 0.7 $cm^3$ in volume) were divided into five groups of ten animals each. A description of the experimental groups is given below. Dosing volumes of either I-5 or its lysyl-β-alaninate ester (1 mL/kg) were based on the average weight of the animals in each dosing group and were adjusted as necessary twice a week. Treatment schedules are provided in Table 5. Tumors were measured in anesthetized animals (isofluorane vapor for approximately 1–2 minutes) every 3–4 days using a vernier caliper. Tumor volume was calculated using the formula:

$$V(cm)=0.5236\times length(cm)\times width(cm)[(length(cm)+width(cm))/2].$$

Drug solutions

Indolocarbazole I-5 was dissolved in vehicle defined below:

| | |
|---|---|
| 40% PEG 1000 | (Spectrum, Los Angeles, CA) |
| 10% PVP C30 | (ISP, Boundbrook, NJ) |
| 2% benzyl alcohol | (Spectrum, Los Angeles, CA) |
| Water | (Milli Q or HPLC grade (Fisher Scientific, Pittsburgh, PA) |

All reagents were USP grade.

(I-5)-Lysyl-β-alaninate was dissolved in 50 mM sodium acetate buffer, pH 5.5.

TABLE 5

Treatment Schedule

| Treatment Group | # of Rats | Treatment | Dose | Schedule |
|---|---|---|---|---|
| 1. I-5 Vehicle | 10 | Vehicle | 1 ml/kg, sc | Daily |
| 2. I-5 | 10 | I-5 | 1 mL/kg, sc of 9.2 mg/mL | Daily |
| 3. (I-5)-Lysyl-β-alaninate Vehicle | 10 | Vehicle | 1 ml/kg, sc | Daily |
| 4. (I-5)-Lysyl-β-alaninate | 10 | (I-5)-Lysyl-β-alaninate | 1 mL/kg, sc of 16 mg/mL | Daily |
| 5. No-Treatment | 10 | None | None | None |

Results

Indolocarbazole I-5 and (I-5)-lysyl-β-alaninate were both effective in inhibiting the growth of AT-2 tumors in adult male Copenhagen rats (Table 6). Anti-tumor efficacy was first noted by Day 6 of dosing and reached values of 53% (I-5) and 72% ((I-5)-lysyl-β-alaninate)) inhibition of tumor growth by Day 13 of dosing, at which time tumor measurements were discontinued.

TABLE 6

| Groups | Day 0 | Day 3 | Day 6 | Day 9 | Day 13 |
|---|---|---|---|---|---|
| I-5, Vehicle | 0.6 ± 0.1 (N = 10) | 2.3 ± 0.2 (N = 10) | 5.0 ± 0.4 (N = 10) | 13.4 ± 2.5 (N = 10) | 24.6 ± 3.9 (N = 10) |
| I-5, 10 mg/kf, daily | 0.7 ± 0.1 (N = 10) | 1.6 ± 0.2 (N = 10)* | 2.1 ± 0.1 (N = 10)*** | 5.4 ± 0.7 (N = 10)** | 11.6 ± 1.8 (N = 9)** |
| (I-5)-Lysyl-β-alaninate, Vehicle | 0.7 ± 0.1 (N = 10) | 2.1 ± 0.3 (N = 10) | 4.6 ± 0.6 (N = 10) | 12.6 ± 1.6 (N = 8) | 29.7 ± 3.7 (N = 8) |
| (I-5)-Lysyl-β-alaninate, 10 mg/kg, daily | 0.6 ± 0.1 (N = 10) | 1.5 ± 0.2 (N = 10) | 2.1 ± 0.2 (N = 10)*** | 4.8 ± 0.6 (N = 10)*** | 8.3 ± 0.5 (N = 10)*** |
| Control, no-treatment | 0.7 ± 0.1 (N = 10) | 3.1 ± 0.3 (N = 10) | 6.7 ± 0.6 (N = 10) | 15.3 ± 2.0 (N = 9) | 34.2 ± 5.4 (N = 9) |

Dunnett's test was applied for statistical analysis using the Pharm/PCS Version 4.2, Springer-Verlag, New York.
Results are Mean ± SE; N = Number of Rats
* = $p < 0.05$;
** = $p < 0.01$;
*** = $p < 0.001$ in respect to their vehicle treated group (Unpaired Students t test)

It is intended that each of the published documents mentioned in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention.

What is claimed is:

[1. An indolocarbazole-ester-of-formula Q—L—C(=O)—A wherein:

A is a solubilizing group selected from the group consisting of an amino acid residue, a dipeptide residue, $—(CH_2)_mZ$, $—(CH_2)_mC(=O)NH(CH_2)_mZ$, $—(CH_2)_mC(=O)NH—Z$, $—(CH_2)_mZ(CH_2)_mZ$, branched $—(CH_2)_nCH[(CH_2)_mZ]_2$, $—(CH_2)_m—Z[(CH_2)_mZ]_2$, $—(CH_2)_n—A^1$.$—(CH_2)_n$-heteroaryl and $—NH(CH_2)_mN(CH_3)_2$; wherein:

n is an integer from 0 to 5;

m is an integer from 1–6;

Z is selected from the group consisting of a basic group, $—C(=NH)NH_2$, cyclic amidine, $—NHC(NH_2)=NR^{11}$, cyclic guanidine and an acidic group; and $A^1$ is aryl or heteroaryl substituted with one to three substituents of formula $—(CH_2)_nZ$;

L is oxygen; and

Q is an indolocarbazole residue of the formula:

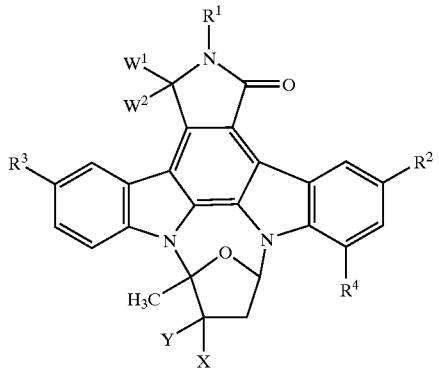

wherein:

$R^1$ is hydrogen, carbamoyl, lower alkyl, amino, lower alkanoyl, $—CH_2R^5$ or $—CH_2CH_2R^5$;

$R^5$ is halogen, amino, di-lower alkylamino, hydroxyl, a single bond attached to —L—C(=O)—A, or lower alkylamino optionally substituted with hydroxyl or a single bond attached to —L—C(=O)—A;

$R^2$ and $R^3$ are independently hydrogen, hydroxyl, cyano, lower alkoxy, halogen, hydroxymethyl, lower alkoxymethyl, lower alkylthiomethyl, lower alkylsulfinylmethyl, arylthiomethyl, heteroarylthiomethyl, arylsulfinylmethyl, heteroarylsulfinylmethyl, arylmethylthiomethyl, heteroarylmethylthiomethyl, $CH=NNHC(=NH)NH_2$, nitro, lower alkanoyl, lower alkanoyloxy, sulfonic acid, $—SO_2NR^8R^9$, $—OC(=O)NR^8R^9$, $—CH=NNR^8R^9$, $—NR^6R^7$, $—OCO_2R^{10}$, $—NHC(=O)NHR^{11}$, $—CH_2OC(=O)NHR^{11}$, $—NHCO_2R^{11}$, lower alkyl sulfonylmethyl, (dialkylamino) alkylthiomethyl, a single bond attached to $—L—C(=O)—A^1$, or lower alkyl optionally substituted with hydroxyl or a single bond attached to —L—C(=O)—A;

one of $R^6$ and $R^7$ is hydrogen and the other is hydrogen, lower alkyl, carbamoyl, lower alkylaminocarbonyl, lower alkanoyl or phenylaminocarbonyl; or $R^6$ and $R^7$ are both lower alkyl;

$R^8$ and $R^9$ are independently hydrogen, lower alkyl, aryl, heteroaryl or $R^8$ and $R^9$, together with the nitrogen atom to which they are attached, form a heterocycle;

$R^{10}$ if lower alkyl or substituted or unsubstituted phenyl;

$R^{11}$ is hydrogen or lower alkyl;

$R^4$ is hydrogen, amino or $—NHC(=O)NHC_2H_5$;

one of $W^1$ and $W^2$ is hydrogen, and the other is selected from the group consisting of hydrogen, hydroxyl, lower alkoxy, lower alkylthio and a single bond attached to —L—C(=O)—A, or $W^1$ and $W^2$ combined together are oxygen;

X is hydrogen, $—CH_2—NHC(=O)O—C_6H_5$, formyl, carboxyl, alkoxycarbonyl having from 2 to 13 carbons, cycloalkoxycarbonyl having from 4 to 11 carbons, $—(CH_2)_nCH_2N(R^{11})_2$ wherein n is an integer from 0 to 5, $—C(=O)NR^{12}R^{13}$, $—CH_2B$, $—NR^{14}R^{15}$, $—N=CHN(CH_3)_2$, $—OCOCH_2CH_2CO_2H$, lower alkylhydrazinocarbonyl, $—CH=N—R^{16}$, $—CONHR^{17}$, a group of formula:

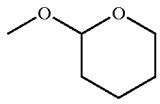

$R^{12}$ and $R^{13}$ are independently hydrogen, lower alkyl, phenyl, lower alkyl optionally substituted by hydroxyl or by a single bond attached to —L—C(=O)—A, or $R^{12}$ and $R^{13}$ are combined together to form a 3–6 carbon heterocyclic ring which optionally contains at least one O, S and/or additional N heteroatom, or $R^{12}$ is hydrogen and $R^{13}$ is hydroxyl, phenyl, or a single bond attached to —L—C(=O)—A;

B is hydroxyl, lower alkoxy, lower alkanoyloxy, azido, lower alkylthio, arylthio, heteroarylthio, lower alkylsulfinyl, arylsulfinyl, heteroarylsulfinyl or a single bond attached to —L—C(=O)—A;

one of $R^{14}$ or $R^{15}$ is hydrogen and the other is hydrogen lower alkyl, allyl, carboxyl-substituted lower alkyl, carbamoyl, lower alkyl- or aryl-substituted carbamoyl, a residue to an α-amino acid in which the carboxylate hydrogen is removed, or lower alkoxycarbonyl-substituted lower alkyl; or both $R^{14}$ and $R^{15}$ are lower alkyl or chlorine-substituted lower alkyl; or $R^{14}$ and $R^{15}$ are combined together to form $—CH_2CH_2DCH_2CH_2—$ wherein D is $—CH_2—$, —NH—, —S— or —O—;

$R^{16}$ is hydroxyl, carbamoylamino, $—NR^8R^9$ guanidino, 2-imidazolylamino or a single bond attached to —L—C(=O)—A;

$R^{17}$ is the residue of an α-amino acid after removal of the amino group thereof, wherein the carboxyl group of the α-amino acid is optionally esterified by a lower alkyl alcohol or benzyl alcohol;

Y is hydroxyl, lower alkanoyloxy, carbamoyloxy, lower alkoxy, or a single bond attached to —L—C(=O)—A, or X and Y together may be $—CH_2OC(CH_3)_2O—$, O=, $—CH_2O—$, $—CH_2OCO_2—$, $—CH_2OC(=S)O—$, $—CH_2N(R^{18})CO_2—$, $—CH_2NHC(=S)O—$, $—CH_2OS(=O)O—$, $—OC(=S)NHCH_2—$ or $—O—C(R^{19})=N—CH_2—$;

$R^{18}$ is hydrogen, lower alkyl, allyl, formylmethyl, —$CH_2CH{=}NNHC({=}NH)NH_2$, —$CH_2CH(—G)CH_2$—J wherein G and J are independently hydroxyl or one of them is a single bond attached to —L—C(=O)—A; and $R^{19}$ is lower alkyl or lower alkylthio;

provided that one of $R^2$, $R^3$, $R^5$, $W^1$, $W^2$, X and Y contains a single bond attached to —L—C(=O)—A;

provided that where $R^1$, $R^2$, $R^3$, $R^4$, $W^1$ and $W^2$ are H, Y cannot be hydroxyl when X is —$CH_2$—O—C(=O)$CH_2NH_2$ or —$CH_2$—O—C(=O)$CH_2$NH-cbz;

and further provided that the solubilizing group A is other than 3-dimethylaminobutyric acid, lysyl-β-alanine and a residue of succinic acid.]

2. The compound of [claim 1] *claim 36* wherein $R^1$ is hydrogen, carbamoyl, lower alkyl, amino, lower alkanoyl or —$CH_2CH_2R^5$.

3. The compound of [claim 1] *claim 36* wherein $R^1$ is —$CH_2R^5$.

4. The compound of [claim 1] *claim 36* wherein the solubilizing group is an amino acid residue, wherein the amino acid residue is an α-amino acid residue.

5. The compound of [claim 1] *claim 36* wherein the solubilizing group is a dipeptide residue.

6. The compound of [claim 1] *claim 36* wherein Z is a basic group selected from the group consisting of amino and —$NR^{20}R^{21}$ wherein:

$R^{20}$ and $R^{21}$, independently, are selected from the group consisting of lower alkyl having 1 to 6 carbons and 2-hydroxyethyl; or $R^{20}$ and $R^{21}$ are combined together to form —$CH_2CH_2MCH_2CH_2$— wherein M is —$CH_2$—, —S—, —O— or —N($R^{11}$)—.

7. The compound of [claim 1] *claim 36* wherein Z is selected from the group consisting of —C(=NH)$NH_2$, cyclic amidine, —NHC($NH_2$)=$NR^{11}$, and cyclic guanidine.

8. The compound of claim 7 wherein the cyclic amidine is 2-imidazolidyl.

9. The compound of claim 7 wherein the cyclic guanidine is 2-(2-aminoimidazolidyl).

10. The compound of [claim 1] *claim 36* wherein Z is an acidic group selected from the group consisting of $CO_2H$, $PO_2H$, $PO_3H_2$, $SO_3H_2$, tetrazolyl, an amino acid residue and $SO_2NHR^{11}$.

11. The compound of [claim 1] *claim 36* wherein $A^1$ is phenyl substituted with one to three substituents of formula —$(CH_2)_n$-3-dimethylaminomethyl.

12. The compound of [claim 1] *claim 36* wherein the solubilizing group is selected from the group consisting of [Lysine, Glycine, Alanine,] N,N-Dimethylglycine, [Histidine, Arginine,] β-Alanine, α-Aminosobutyric Acid, [Valine, Leucine, Isoleucine, Proline, Serine, Threonine, Cysteine, Aspartic Acid,] Morpholine-1-acetic acid, 4-Methyl-1-piperazine acetic acid, β-Alanine-(2-aminopropionic) acid, N-(3-dimethylaminoethyl) succinamic acid, N-(3-Butanoic acid)-2,6-diaminohexanamide, 3-Dimethylaminobenzoic acid, 3-Guanadinopropionic acid, $HO_2CCH_2CH_2CONHCH_2CH_2SO_3H$, $HO_2CCH_2CH_2SO_3H$ and $HO_2CCH_2CH_2PO_3H_2$.

13. The compound of [claim 12] *claim 36* wherein the solubilizing group is selected from the group consisting of [Lysine, Glycine, Alanine,] N,N-Dimethylglycine, [Histidine, Arginine,] β-Alanine, and α-Aminoisobutyric Acid.

14. The compound of [claim 1] *claim 36* wherein $R^1$ is hydrogen.

15. The compound of [claim 1] *claim 36* wherein $R^2$ and $R^3$ are independently selected from the group consisting of H, $NH_2$, hydroxyl, halogen, substituted or unsubstituted lower alkylthiomethyl, lower alkylsulfinylmethyl, arylthiomethyl, lower alkyl sulfonylmethyl, (dialkylamino) alkylthiomethyl, heteroarylmethylthiomethyl, heteroarylthiomethyl and a single bond attached to —L—C(=O)—A.

16. The compound of claim 15 wherein $R^2$ and $R^3$ are independently selected from the group consisting of hydrogen, $NH_2$, hydroxyl, halogen, $CH_2S({=}O)C_2H_5$, $CH_2SC_2H_5$, $CH_2SC_6H_5$, $CH_2S({=}O)_2C_2H_5$, $CH_2S(CH_2)_2N(CH_3)_2$, $CH_2SCH_2$—(2-furyl), $CH_2$S-3-(1,2,4-triazolyl), and a single bond attached to —L—C(=O)—A.

17. The compound of claim 16 wherein $R^2$ and $R^3$ are independently selected from the group consisting of hydrogen, substituted or unsubstituted lower alkylthiomethyl.

18. The compound of [claim 1] *claim 36* wherein Y is hydroxyl, lower alkoxy or a single bond attached to —L—C(=O)—A.

19. The compound of [claim 1] *claim 36* wherein X is selected from the group consisting of methoxycarbonyl, —$CH_2$—S(=O)$CH_3$, —$CH_2N(CH_3)_2$, hydroxymethyl, —$CH_2$—B wherein B is a single bond attached to —L—C(=O)—A, [glucosylthiomethyl,] —$CH_2$—NHC(=O)O—$C_6H_5$, and —C(=O)NH$(CH_2)_2$—OH.

20. The compound of [claim 1] *claim 36* wherein $R^1$, $R^2$, $R^3$, $R^4$, $W^1$ and $W^2$ are each H; Y is lower alkoxy; and X is —$CH_2$—B wherein B a single bond attached to —L—C(=O)—A.

21. The compound of [claim 1] *claim 36* wherein $R^1$, $R^2$, $R^3$, $R^4$, $W^1$ and $W^2$ are each H; Y is lower alkoxy; and X is —$CH_2$—B wherein B a single bond attached to —L—C(=O)—A.

22. The compound of claim 21 wherein Y is methoxy.

23. The compound of [claim 1] *claim 36* wherein $R^1$, $R^4$, $W^1$ and $W^2$ are H; $R^2$ and $R^3$ are both lower alkylthiomethyl; X is methoxycarbonyl; and Y is a single bond attached to —L—C(=O)—A.

24. The compound of claim 23 wherein $R^2$ and $R^3$ are each —$CH_2SC_2H_5$.

25. The compound of [claim 1] *claim 36* wherein Q is a residue having a formula selected from the group consisting of the listed substituents at positions $R^2$ , $R^3$, Y and X:

| Formula(1) | $R^2$ | $R^3$ | Y | X |
|---|---|---|---|---|
| I-1 | H | H | OH | $CO_2CH_3$ |
| I-2 | OH | H | OH | $CO_2CH_3$ |
| I-3 | H | H | OH | $CH_2S({=}O)CH_3$ |
| I-4 | H | H | OH | $CH_2N(CH_3)_2$ |
| I-5 | H | H | $OCH_3$ | $CH_2OH$ |
| I-6(2) | H | H | OH | $CH_2$S-Glc |
| I-7(3) | H | H | OH | $CO_2CH_3$ |

-continued

| Formula[1] | $R^2$ | $R^3$ | Y | X |
|---|---|---|---|---|
| I-8 | $CH_2S(=O)C_2H_5$ | H | OH | $CO_2CH_3$ |
| I-9[3] | Br | Br | OH | $CO_2CH_3$ |
| I-10 | $CH_2SC_2H_5$ | H | OH | $CO_2CH_3$ |
| I-11 | $CH_2SC_6H_5$ | H | OH | $CO_2CH_3$ |
| I-12 | H | H | OH | $CH_2NHCO_2C_6H_5$ |
| I-13 | $CH_2S(=O)_2C_2H_5$ | H | OH | $CO_2CH_3$ |
| I-14 | $CH_2SC_2H_5$ | $CH_2SC_2H_5$ | OH | $CO_2CH_3$ |
| I-15 | $CH_2S(CH_2)_2N(CH_3)_2$ | H | OH | $CO_2CH_3$ |
| I-16 | $CH_2SCH_2$-2-Furyl | H | OH | $CO_2CH_3$ |
| I-17 | Br | Br | OH | $CH_2OH$ |
| I-18 | $CH_2S$-3-(1,2,4-Triazolyl) | H | OH | $CO_2CH_3$ |
| I-19 | $CH_2S(CH_2)_2N(CH_3)_2$ | $CH_2S(CH_2)_2N(CH_3)_2$ | OH | $CO_2CH_3$ |
| I-20[4] | H | H | OH | $CO_2CH_3$ |
| I-21[5] | H | $NH_2$ | OH | $CO_2CH_3$ |
| I-22 | H | H | OH | $C(=O)NH(CH_2)_2OH$ |

[1]$W^1$ and $W^2$ are both hydrogen, or both are combined together to represent oxygen, where indicated in Footnote 3. $R^1$ is hydrogen. $R^4$ is hydrogen except as noted in Footnotes 4 and 5.
[2]Glc is glucose; linkage is through the 1-position.
[3]$W^1$ and $W^2$ are combined together to represent oxygen.
[4]$R^4$ is $NHCONHC_2H_5$.
[5]$R^4$ $NH_2$.

26. The compound of claim 25 wherein Q is a residue having the following substituents: $R_2$ is hydrogen, $R_3$ is hydrogen, Y is $OCH_3$, X is $CH_2OH$, and the solubilizing group is selected from the group consisting of [Lysine, Glycine, Alanine,] N,N-Dimethylglycine, [Histidine, Arginine,] β-Alanine, α-Aminoisobutyric Acid, [Valine, Leucine, Isoleucine, Proline, Serine, Threonine, Cysteine, Aspartic Acid,] Morpholine-1-acetic acid, 4-Methyl-1-piperazine acetic acid, β-Alanine-(2-aminopropionic) acid, N-(3-dimethylaminoethyl) succinamic acid, N-(3-Butanoic acid)-2,6-diaminohexanamide, 3-Dimethylaminobenzoic acid, 3-Guanadinopropionic acid, $HO_2CCH_2CH_2CONHCH_2CH_2SO_3H$, $HO_2CCH_2CH_2SO_3H$ and $HO_2CCH_2CH_2PO_3H_2$.

27. The compound of claim 25 wherein Q is a residue having the following substituents: $R^2$ is $CH_2SC_2H_5$, $R^3$ is $CH_2SC_2H_5$, Y is OH, X is $CO_2CH_3$.

28. The compound of claim 25 wherein Q is a residue having the following substituents: $R_2$ is $CH_2SC_2H_5$, $R_3$ is $CH_2SC_2H_5$, Y is OH, X is $CO_2CH_3$, and the solubilizing group is selected from the group consisting of [Lysine, Glycine, Alanine,] N,N-Dimethylglycine, [Histidine, Arginine,] β-Alanine, α-Aminoisobutyric Acid, [Valine, Leucine, Isoleucine, Proline, Serine, Threonine, Cystine, Aspartic Acid,] Morpholine-1-acetic acid, 4-Methyl-1-piperazine acetic acid, β-Alanine-(2-aminopropionic) acid, N-(3-dimethylaminoethyl) succinamic acid, N-(3-Butanoic acid)-2,6-diaminohexanamide, 3-Dimethylaminobenzoic acid, 3-Guanadinopropionic acid, $HO_2CCH_2CH_2CONHCH_2CH_2SO_3H$, $HO_2CCH_2CH_2SO_3H$ and $HO_2CCH_2CH_2PO_3H_2$.

29. The compound of claim 26 wherein Q is a residue having the following substituents: $R^2$ is hydrogen, $R^3$ is hydrogen, Y is $OCH_3$, X is $CH_2OH$, and the solubilizing group is selected from the group consisting of [Lysine, Glycine, Alanine,] N,N-Dimethylglycine, [Histidine, Arginine,] β-Alanine, and α-Aminoisobutyric Acid.

30. The compound of claim 28 wherein Q is a residue having the following substituents: $R^2$ is $CH_2SC_2H_5$, $R^3$ is $CH_2SC_2H_5$, Y is OH, X is $CO_2CH_3$, and the solubilizing group is selected from the group consisting of [Lysine, Glycine, Alanine,] N,N-Dimethylglycine, [Histidine, Arginine,] β-Alanine, and α-Aminoisobutyric Acid.

31. A method for treating a pathological condition of the prostate comprising administering to a patient a therapeutically effective amount of a compound of [claim 1] *claim 36*.

32. The method of claim 31 wherein the compound is administered with a pharmaceutically-acceptable carrier.

33. The indolocarbazole ester of claim 27 wherein A is a residue of lysyl-β-alanine.

34. The indolocarbazole ester of claim 27 wherein A is a residue of 3-dimethylaminobutyric acid.

35. An indolocarbazole ester of formula Q—L—C(=O)—A wherein:

A is 3-dimethylaminobutyric acid or lysyl-β-alanine;

L is oxygen; and

Q is an indolocarbazole residue of the formula:

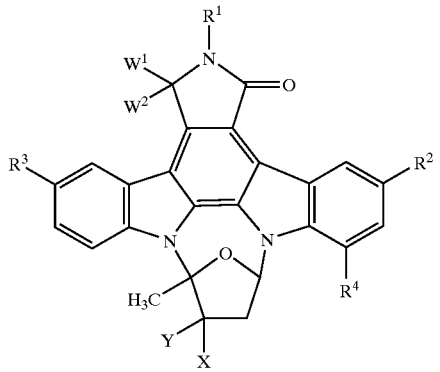

wherein $R^1$ is $—CH_2R^5$;

$R^5$ is halogen, amino, di-lower alkylamino, hydroxyl, a single bond attached to —L—C(=O)—A, or lower alkylamino optionally substituted with hydroxyl or a single bond attached to —L—C(=O)—A;

$R^2$and $R^3$ are independently hydrogen, hydroxyl, cyano, lower alkoxy, halogen, hydroxylmethyl, lower alkoxymethyl, lower alkylthiomethyl, lower alkylsulfinylmethyl, arylthiomethyl, heteroarylthiomethyl, arylsulfinylmethyl, heteroarylsulfinylmethyl, arylmethylthiomethyl, heteroarylmethylthiomethyl, CH═NNHC(═NH)$NH_2$, nitro, lower alkanoyl, lower alkanoyloxy, sulfonic acid, —$SO_2NR^8R^9$, —OC(═O)$NR^8R^9$, —CH═$NNR^8R^9$, —$NR^6R^7$, —$OCO_2R^{10}$, —NHC(═O)$NHR^{11}$, —$CH_2OC$(═O)$NHR^{11}$, —$NHCO_2R^{11}$, lower alkyl sulfonylmethyl, (dialkylamino) alkylthiomethyl, a single bond attached to —L—C(═O)—A, or lower alkyl optionally substituted with hydroxyl or a single bond attached to —L—C(═O)—A;

one of $R^6$ and $R^7$ is hydrogen and the other is hydrogen, lower alkyl, carbamoyl, lower alkylaminocarbonyl, lower alkanoyl or phenylaminocarbonyl; or $R^6$ and $R^7$ are both lower alkyl;

$R^8$ and $R^9$ are independently hydrogen, lower alkyl, aryl, heteroaryl or $R^8$ and $R^9$ together with the nitrogen atom to which they are attached, form a heterocycle;

$R^{10}$ is lower alkyl or substituted or unsubstituted phenyl;

$R^{11}$ is hydrogen or lower alkyl;

$R^4$ is hydrogen, amino or —NHC(═O)$NHC_2H_5$;

one of $W^1$ and $W^2$ is hydrogen, and the other is selected from the group consisting of hydrogen, hydroxyl, lower alkoxy, lower alkylthio and a single bond attached to —L—C(═O)—A, or $W^1$ and $W^2$ combined together are oxygen;

X is hydrogen, —$CH_2$—NHC(═O)O—$C_6H_5$, formyl, carboxyl, alkoxycarbonyl having from 2 to 13 carbons, cycloalkoxycarbonyl having from 4 to 11 carbons, —$(CH_2)_nCH_2N(R^{11})_2$ wherein n is an integer from 0 to 5, —C(═O)$NR^{12}R^{13}$, —$CH_2B$, —$NR^{14}R^{15}$, —N═CHN$(CH_3)_2$, —$OCOCH_2CH_2CO_9H$, lower alkylhydrazinocarbonyl, —CH═N—$R^{16}$, —$CONHR^{17}$, a group of formula:

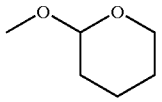

$R^{12}$ and $R^{13}$ are independently hydrogen, lower alkyl, phenyl, lower alkyl optionally substituted by hydroxyl or by a single bond attached to —L—C(═O)—A, or $R^{12}$ and $R^{13}$ are combined together to form a 3–6 carbon heterocyclic ring which optionally contains at least one O, S and/or additional N heteroatom, or $R^{12}$ is hydrogen and $R^{13}$ is hydroxyl, phenyl, or a single bond attached to —L—C(═O)—A;

B is hydroxyl, lower alkoxy, lower alkanoyloxy, azido, lower alkylthio, arylthio, heteroarylthio, lower alkylsulfinyl, arylsulfinyl, heteroarylsulfinyl or a single bond attached to —L—C(═O)—A;

one of $R^{14}$ or $R^{15}$ is hydrogen and the other is hydrogen, lower alkyl, allyl, carboxyl-substituted lower alkyl, carbamoyl, lower alkyl- or aryl-substituted carbamoyl, a residue of an α-amino acid in which the carboxylate *group* [hydrogen] is removed, or lower alkoxycarbonyl-substituted lower alkyl; or both $R^{14}$ and $R^{15}$ are lower alkyl or chlorine-substituted lower alkyl; or $R^{14}$ and $R^{15}$ are combined together to form —$CH_2CH_2DCH_2CH_2$— wherein D is —$CH_2$—, —NH—, —S— or —O—;

$R^{16}$ is hydroxyl, carbamoylamino, —$NR^8R^9$ guanidino, 2-imidazolylamino or a single bond attached to —L—C(═O)—A;

$R^{17}$ is the residue of an α-amino acid after removal of the amino group thereof, wherein the carboxyl group of the α-amino acid is optionally esterified by a lower alkyl alcohol or benzyl alcohol;

Y is hydroxyl, lower alkanoyloxy, carbamoyloxy, lower alkoxy, or a single bond attached to —L—C(═O)—A, or X and Y together may be —$CH_2OC(CH_3)_2$(—, O═, —$CH_2O$—, —$CH_2OCO_2$—, —$CH_2OC$(═S) O—, —$CH_2N(R^{18})CO_2$—, —$CH_2NHC$(═S)O—, —$CH_2OS$(═O)O—, —OC(═S)$NHCH_2$— of —O—C($R^{19}$)═N—$CH_2$—;

$R^{18}$ is hydrogen, lower alkyl, allyl, formylmethyl, —$CH_2CH$═NNHC(═NH)$NH_2$, —$CH_2CH$(—G)$CH_2$—J wherein G and J are independently hydroxyl or one of them is a single bond attached to —L—C(═O)—A; and $R^{19}$ is lower alkyl or lower alkylthio;

provided that one of $R^2$, $R^3$, $R^5$, $W^1$, $W^2$, X and Y contains a single bond attached to —L—C(═O)—A.

and further provided that where $R^1$, $R^2$, $R^3$, $R^4$, $W^1$ and $W^2$ are H, Y cannot be hydroxyl where X is —$CH_2$—O—C(═O)$CH_2NH_2$ or —$CH_2$—O—C(═O)$CH_2NH$-cbz.

*36. An indolocarbazole ester of formula Q—L—C(═O)—A wherein:*

*A is a solubilizing group selected from the group consisting of an amino acid residue, a dipeptide residue, —$(CH_m)_mZ$, —$(CH_2)_mC$(═O)$NH(CH_2)_mZ$, —$(CH_2)_mC$(═O)NH—Z, —$(CH_2)_mZ(CH_2)_mZ$, branched —$(CH_2)_nCH[(i\ CH_2)_mZ]_2$, —$(CH_2)_m$—$Z[(CH_2)_mZ]_2$, —$(CH_2)_n$—$A^1$, —$(CH_2)_n$-heteroaryl and —$NH(CH_2)_mN(CH_3)_2$;*

*wherein:*

*n is an integer from 0 to 5;*

*m is an integer from 1–6;*

*Z is selected from the group consisting of a basic group, —C(═NH)$NH_2$, cyclic amidine, —NHC($NH_2$)═$NR^{11}$, cyclic guanidine and an acidic group; and*

*$A^1$ is aryl or heteroaryl substituted with one to three substituents of formula —$(CH_2)_nZ$;*

*L is oxygen; and*

*Q is an indolocarbazole residue of formula:*

I

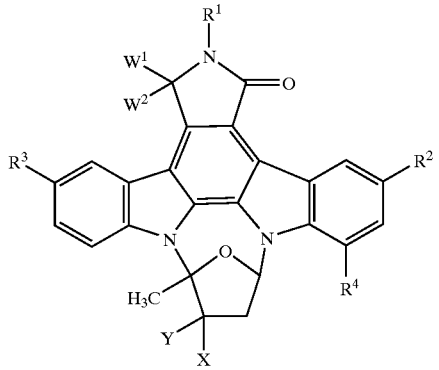

*wherein:*

*$R^1$ is hydrogen, carbamoyl, lower alkyl, amino, lower alkanoyl, —$CH_2R^5$ or —$CH_2CH_2R^5$;*

*$R^5$ is halogen, amino, di-lower alkylamino, hydroxyl, a single bond attached to —L—C(═O)—A, or lower alkylamino optionally substituted with hydroxyl or a single bond attached to —L—C(═O)—A;*

$R^2$ and $R^3$ are independently hydrogen, hydroxyl, cyano, lower alkoxy, halogen, hydroxymethyl, lower alkoxymethyl, lower alkylthiomethyl, lower alkylsulfinylmethyl, arylthiomethyl, heteroarylthiomethyl, arylsulfinylmethyl, heteroarylsulfinylmethyl, arylmethylthiomethyl, heteroarylmethylthiomethyl, $CH{=}NNHC({=}NH)NH_2$, nitro, lower alkanoyl, lower alkanoyloxy, sulfonic acid, $—SO_2NR^8R^9$, $—OC({=}O)NR^8R^9$, $—CH{=}NNR^8R^9$, $—NR^6R^7$, $—OCO_2R^{10}$, $—NHC({=}O)NHR^{11}$, $—CH_2OC({=}O)NHR^{11}$, $—NHCO_2R^{11}$, lower alkyl sulfonylmethyl, (dialkylamino)alkylthiomethyl, a single bond attached to —L—C(=O)—A, or lower alkyl optionally substituted with hydroxyl or a single bond attached to —L—C(=O)—A;

one of $R^6$ and $R^7$ is hydrogen and the other is hydrogen, lower alkyl, carbamoyl, lower alkylaminocarbonyl, lower alkanoyl or phenylaminocarbonyl; or $R^6$ and $R^7$ are both lower alkyl;

$R^8$ and $R^9$ are independently hydrogen, lower alkyl, aryl, heteroaryl or $R^8$ and $R^9$ together with the nitrogen atom to which they are attached, form a heterocycle;

$R^{10}$ is lower alkyl or substituted or unsubstituted phenyl;

$R^{11}$ is hydrogen or lower alkyl;

$R^4$ is hydrogen amino or $—NHC({=}O)NHC_2H_5$;

one of $W^1$ and $W^2$ is hydrogen, and the other is selected from the group consisting of hydrogen, hydroxyl, lower alkoxy, lower alkylthio and a single bond attached to —L—C(=O)—A, or $W^1$ and $W^2$ combined together are oxygen;

X is hydrogen, $—CH_2—NHC({=}O)O—C_6H_5$, formyl, carboxyl, alkoxycarbonyl having from 2 to 13 carbons, cycloalkoxycarbonyl having from 4 to 11 carbons, $—(CH_2)_nCH_2N(R^{11})_2$ wherein n is an integer from 0 to 5, $—C({=}O)NR^{12}R^{13}$, $—CH_2B$, $—NR^{14}R^{15}$, $—N{=}CHN(CH_3)_2$, $—OCOCH_2CH_2CO_2H$, lower alkylhydrazinocarbonyl, $—CH{=}N—R^{16}$, $—CONHR^{17}$, a group of formula:

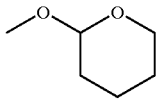

$R^{12}$ and $R^{13}$ are independently hydrogen, lower alkyl, phenyl, lower alkyl optionally substituted by hydroxyl or by a single bond attached to —L—C(=O)—A, or $R^{12}$ and $R^{13}$ are combined together to form a 3–6 carbon heterocyclic ring which optionally contains at least one O, S and/or additional N heteroatom, or $R^{12}$ is hydrogen and $R^{13}$ is hydroxyl, phenyl, or a single bond attached to —L—C(=O)—A;

B is hydroxyl, lower alkoxy, lower alkanoyloxy, azido, lower alkythio, arylthio, heteroarylthio, lower alkylsulfinyl, arylsulfinyl, heteroarylsulfinyl or a single bond attached to —L—C(=O)—A provided that A is not a glycine residue, or a residue of D-, L- or racemic alanine, valine, leucine, isoleucine, proline, phenylalanine, tryptophan, methionine, serine, threonine, cysteine, tyrosine, asparagine, glutamine, aspartic acid, glutamic acid, lysine, arginine, or histidine;

one of $R^{14}$ or $R^{15}$ is hydrogen and the other is hydrogen, lower alkyl, allyl, carboxyl-substituted lower alkyl, carbamoyl, lower alkyl- or aryl-substituted carbamoyl, a residue of an α-amino acid in which the carboxylate hydrogen is removed, or lower alkoxycarbonyl-substituted lower alkyl; or both $R^{14}$ and $R^{15}$ are lower alkyl or chlorine-substituted lower alkyl; or $R^{14}$ and $R^{15}$ are combined together to form $—CH_2CH_2DCH_2$, $CH_2$— wherein D is $—CH_2—$, —NH—, —S— or —O—;

$R^{16}$ is hydroxyl, carbamoylamino, $—NR^8R^9$ guanidino, 2-imidazolylamino or a single bond attached to —L—C(=O)—A;

$R^{17}$ is the residue of an α-amino acid after removal of the amino group thereof, wherein the carboxyl group of the α-amino acid is optionally esterified by a lower alkyl alcohol or benzyl alcohol;

Y is hydroxyl, lower alkanoyloxy, carbamoyloxy, lower alkoxy, or a single bond attached to —L—C(=O)—A, or X and Y together may be $—CH_2OC(CH_3)_2O—$, O=, $—CH_2O—$, $—CH_2OCO_2—$, $—CH_2OC({=}S)O—$, $—CH_2N(R^{18})CO_2—$, $—CH_2NHC({=}S)O—$, $—CH_2OS({=}O)O—$, $—OC({=}S)NHCH_2$—or $—O—C(R^{19}){=}N—CH_2—$;

$R^{18}$ is hydrogen, lower alkyl, allyl, formylmethyl, $—CH_2CH{=}NNHC({=}NH)NH_2$, $—CH_2CH(—G)CH_2—J$ wherein G and J are independently hydroxyl or one of them is a single bond attached to —L—C(=O)—A; and $R^{19}$ is lower alkyl or lower alkylthio;

provided that one of $R^2$, $R^3$, $R^5$, $W^1$, $W^2$, X and Y contains a single bond attached to —L—C(=O)—A;

further provided that where $R^1$, $R^2$, $R^3$, $R^4$, $W^1$ and $W^2$ are H, Y cannot be hydroxyl when X is $—CH_2—O—C({=}O)CH_2NH_2$ or $—CH_2—O—C({=}O)CH_2NH$-cbz;

and further provided that the solubilizing group A is other than a residue of 3-dimethylaminobutyric acid, lysyl-β-alanine or succinic acid.

37. An indolocarbazole ester of formula Q—L—C(=O)—A wherein:

A is a solubilizing group selected from the group consisting of an amino acid residue, a dipeptide residue, $—(CH_2)_mZ$, $—(CH_2)_mC({=}O)NH(CH_2)_mZ$, $—(CH_2)_mC({=}O)NH—Z$, $—(CH_2)_mZ(CH_2)_mZ$, branched $—(CH_2)_nCH[(CH_2)_mZ]_2$, $—(CH_2)_m—Z[(CH_2)_mZ]_2$, $—(CH_2)_n—A^1$, $—(CH_2)_n$-heteroaryl and $—NH(CH_2)_mN(CH_3)_2$; wherein:

n is an integer from 0 to 5;

m is an integer from 1–6;

Z is selected from the group consisting of a basic group, $—C({=}NH)NH_2$, cyclic amidine, $—NHC(NH_2){=}NR^{11}$, cyclic guanidine and an acidic group; and $A^1$ is aryl or heteroaryl substituted with one to three substituents of formula $—(CH_2)_nZ$;

L is oxygen; and

*Q is an indolocarbazole residue of formula:*

I

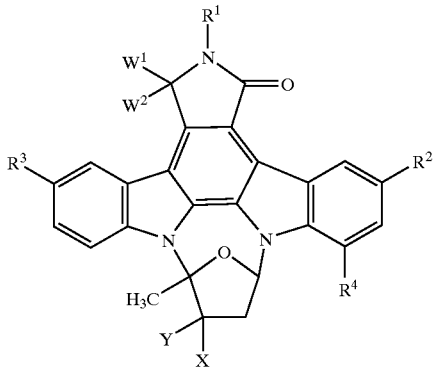

*wherein:*

$R^1$ *is hydrogen, carbamoyl, lower alkyl, amino, lower alkanoyl,* $—CH_2R^5$ *or* $—CH_2CH_2R^5$;

$R^5$ *is halogen, amino, di-lower alkylamino, hydroxyl, a single bond attached to —L—C(=O)—A, or lower alkylamino optionally substituted with hydroxyl or a single bond attached to —L—C(=O)—A;*

$R^2$ *and* $R^3$ *are independently hydrogen, hydroxyl, cyano, lower alkoxy, halogen, hydroxymethyl, lower alkoxymethyl, lower alkylthiomethyl, lower alkylsulfinylmethyl, arylthiomethyl, heteroarylthiomethyl, arylsulfinylmethyl, heteroarylsulfinylmethyl, arylmethylthiomethyl, heteroarylmethylthiomethyl,* $CH=NNHC(=NH)NH_2$, *nitro, lower alkanoyl, lower alkanoyloxy, sulfonic acid,* $—SO_2NR^8R^9$, $—OC(=O)NR^8R^9$, $—CH=NNR^8R^9$, $—NR^6R^7$, $—OCO_2R^{10}$, $—NHC(=O)NHR^{11}$, $—CH_2OC(=O)NHR^{11}$, $—NHCO_2R^{11}$, *lower alkyl sulfonylmethyl, (dialkylamino)alkylthiomethyl, a single bond attached to —L—C(=O)—A, or lower alkyl optionally substituted with hydroxyl or a single bond attached to —L—C(=O)—A;*

*one or* $R^6$ *and* $R^7$ *is hydrogen and the other is hydrogen, lower alkyl, carbamoyl, lower alkylaminocarbonyl, lower alkanoyl or phenylaminocarbonyl; or* $R^6$ *and* $R^7$ *are both lower alkyl;*

$R^8$ *and* $R^9$ *are independently hydrogen, lower alkyl, aryl, heteroaryl or* $R^8$ *and* $R^9$ *together with the nitrogen atom to which they are attached, form a heterocycle;*

$R^{10}$ *is lower alkyl or substituted or unsubstituted phenyl;*

$R^{11}$ *is hydrogen or lower alkyl;*

$R^4$ *is hydrogen, amino or* $—NHC(=O)NHC_2H_5$;

*one of* $W^1$ *and* $W^2$ *is hydrogen, and the other is selected from the group consisting of hydrogen, hydroxyl, lower alkoxy, lower alkylthio and a single bond attached to —L—C(=O)—A, or* $W^1$ *and* $W^2$ *combined together are oxygen;*

*X is hydrogen,* $—CH_2—NHC(=O)O—C_6H_5$, *formyl, carboxyl, alkoxycarbonyl having from 2 to 13 carbons, cycloalkoxycarbonyl having from 4 to 11 carbons,* $—(CH_2)_nCH_2N(R^{11})_2$ *wherein n is an integer from 0 to 5,* $—C(=O)NR^{12}R^{13}$, $—CH_2B$, $—NR^{14}R^{15}$, $—N=CHN(CH_3)_2$, $—OCOCH_2CH_2CO_2H$, *lower alkylhydrazinocarbonyl,* $—CH=N—R^{16}$, $—CONHR^{17}$, *a group of formula:*

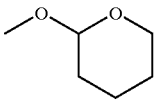

$R^{12}$ *and* $R^{13}$ *are independently hydrogen, lower alkyl, phenyl, lower alkyl optionally substituted by hydroxyl or by a single bond attached to —L—C(=O)—A, or* $R^{12}$ *and* $R^{13}$ *are combined together to form a 3–6 carbon heterocyclic ring which optionally contains at least one O, S and/or additional N heteroatom, or* $R^{12}$ *is hydrogen and* $R^{13}$ *is hydroxyl, phenyl, or a single bond attached to —L—C(=O)—A;*

*B is hydroxyl, lower alkoxy, lower alkanoyloxy, azido, lower alkythio, arylthio, heteroarylthio, lower alkylsulfinyl, arylsulfinyl, heteroarylsulfinyl or a single bond attached to —L—C(=O)—A;*

*one of* $R^{14}$ *or* $R^{15}$ *is hydrogen and the other is hydrogen, lower alkyl, allyl, carboxyl-substituted lower alkyl, carbamoyl, lower alkyl- or aryl-substituted carbamoyl, a residue of an α-amino acid in which the carboxylate hydrogen is removed, or lower alkoxycarbonyl-substituted lower alkyl; or both* $R^{14}$ *and* $R^{15}$ *are lower alkyl or chlorine-substituted lower alkyl; or* $R^{14}$ *and* $R^{15}$ *are combined together to form* $—CH_2CH_2DCH_2CH_2—$ *wherein D is* $—CH_2—$, $—NH—$, $—S—$ *or* $—O—$;

$R^{16}$ *is hydroxyl, carbamoylamino,* $—NR^8R^9$ *guanidino, 2-imidazolylamino or a single bond attached to —L—C(=O)—A;*

$R^{17}$ *is the residue of an α-amino acid after removal of the amino group thereof, wherein the carboxyl group of the α-amino acid is optionally esterified by a lower alkyl alcohol or benzyl alcohol;*

*Y is hydroxyl, lower alkanoyloxy, carbamoyloxy, lower alkoxy, or a single bond attached to —L—C(=O)—A, or X and Y together may be* $—CH_2OC(CH_3)_2O—$, $O=$, $—CH_2O—$, $—CH_2OCO_2—$, $—CH_2OC(=S)O—$, $—CH_2N(R^{18})CO_2—$, $—CH_2NHC(=S)O—$, $—CH_2OS(=O)O—$, $—OC(=S)NHCH_2—$ *or* $—O—C(R^{19})=N—CH_2—$;

$R^{18}$ *is hydrogen, lower alkyl, allyl, formylmethyl,* $—CH_2CH=NNHC(=NH)NH_2$, $—CH_2CH(-G)CH_2—J$ *wherein G and J are independently hydroxyl or one of them is a single bond attached to —L—C(=O)A; and*

$R^{19}$ *is lower alkyl or lower alkylthio;*

*provided that one of* $R^2$, $R^3$, $R^5$, $W^1$, $W^2$, *X and Y contains a single bond attached to —L—C(=O)—A;*

*further provided that where* $R^1$, $R^2$, $R^3$, $R^4$, $W^1$ *and* $W^2$ *are H, Y cannot be hydroxyl when X is* $—CH_2—O—C(=O)CH_2NH_2$ *or* $—CH_2—O—C(=O)CH_2NH$-cbz;

*and further provided that the solubilizing group A is other than a residue of 3-dimethylaminobutyric acid, lysyl-β-alanine, succinic acid, or glycine, or a residue or D—, L— or racemic alainine, valine, leucine, isoleucine, proline, phenylalanine, tryptophan, methionine, serine, threonine, cysteine, tyrosine, asparagine, glutamine, aspartic acid, glutamic acid, lysine, arginine, or histidine.*

*38. An indolocarbazole ester of formula Q—L—C(=O)—A wherein:*

*A is a solubilizing group selected from the group consisting of an amino acid residue, a dipeptide residue,*

—$(CH_2)_mZ$, —$(CH_2)_mC(=O)NH(CH_2)_mZ$, —$(CH_2)_mC(=O)NH$—$Z$, —$(CH_2)_mZ(CH_2)_mZ$, branched —$(CH_2)_nCH[(CH_2)_mZ]_2$, —$(CH_2)_m$—$Z[(CH_2)_mZ]_2$, —$(CH_2)_n$—$A^1$, —$(CH_2)_n$-heteroaryl and —$NH(CH_2)_mN(CH_3)_2$;

wherein:

n is an integer from 0 to 5;

m is an integer from 1–6;

Z is selected from the group consisting of a basic group, —$C(=NH)NH_2$, cyclic amidine, —$NHC(NH_2)=NR^{11}$, cyclic guanidine and an acidic group; and $A^1$ is aryl or heteroaryl substituted with one to three substituents of formula —$(CH_2)_nZ$;

L is oxygen; and

Q is an indolocarbazole residue of formula:

I

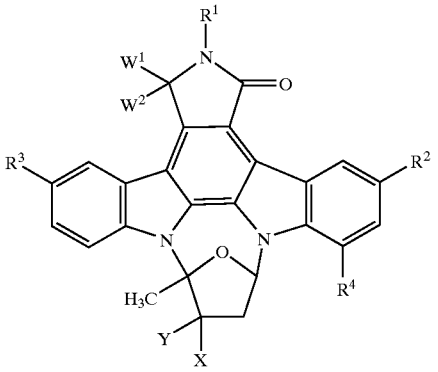

wherein:

$R^1$ is hydrogen, carbamoyl, lower alkyl, amino, lower alkanoyl, —$CH_2R^5$ or —$CH_2CH_2R^5$;

$R^5$ is halogen, amino, di-lower alkylamino, hydroxyl, a single bond attached to —L—C(=O)—A, or lower alkylamino optionally substituted with hydroxyl or a single bond attached to —L—C(=O)—A;

$R^2$ and $R^3$ are independently hydrogen, hydroxyl, cyano, lower alkoxy, halogen, hydroxymethyl, lower alkoxymethyl, lower alkylthiomethyl, lower alkylsulfinylmethyl, arylthiomethyl, heteroarylthiomethyl, arylsulfinylmethyl, heteroarylsulfinylmethyl, arylmethylthiomethyl, heteroarylmethylthiomethyl, CH=NNHC(=NH)$NH_2$, nitro, lower alkanoyl, lower alkanoyloxy, sulfonic acid, —$SO_2NR^8R^9$, —OC(=O)$NR^8R^9$, —CH=$NNR^8R^9$, —$NR^6R^7$, —$OCO_2R^{10}$, —NHC(=O)$NHR^{11}$, —$CH_2OC(=O)NHR^{11}$, —$NHCO_2R^{11}$, lower alkyl sulfonylmethyl, (dialkylamino)alkylthiomethyl, a single bond attached to —L—C(=O)—A, or lower alkyl optionally substituted with hydroxyl or a single bond attached to —L—C(=O)—A;

one of $R^6$ and $R^7$ is hydrogen and the other is hydrogen, lower alkyl, carbamoyl, lower alkylaminocarbonyl, lower alkanoyl or phenylaminocarbonyl; or $R^6$ and $R^7$ are both lower alkyl;

$R^8$ and $R^9$ are independently hydrogen, lower alkyl, aryl, heteroaryl or $R^8$ and $R^9$ together with the nitrogen atom to which they are attached, form a heterocycle;

$R^{10}$ is lower alkyl or substituted or unsubstituted phenyl;

$R^{11}$ is hydrogen or lower alkyl;

$R^4$ is hydrogen, amino or —NHC(=O)$NHC_2H_5$;

one of $W^1$ and $W^2$ is hydrogen, and the other is selected from the group consisting of hydrogen, hydroxyl, lower alkoxy, lower alkylthio and a single bond attached to —L—C(=O)—A, or $W^1$ and $W^2$ combined together are oxygen;

X is hydrogen, —$CH_2$—NHC(=O)O—$C_6H_5$, formyl, carboxyl, alkoxycarbonyl having from 2 to 13 carbons, cycloalkoxycarbonyl having from 4 to 11 carbons, —$(CH_2)_nCH_2N(R^{11})_2$ wherein n is an integer from 0 to 5, —$C(=O)NR^{12}R^{13}$, —$CH_2B$, —$NR^{14}R^{15}$, —N=CH$N(CH_3)_2$, —$OCOCH_2CH_2CO_2H$, lower alkylhydrazinocarbonyl, —CH=N—$R^{16}$, —$CONHR^{17}$, a group of formula:

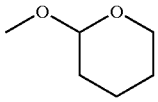

$R^{12}$ and $R^{13}$ are independently hydrogen, lower alkyl, phenyl, lower alkyl optionally substituted by hydroxyl or by a single bond attached to —L—C(=O)—A, or $R^{12}$ and $R^{13}$ are combined together to form a 3–6 carbon heterocyclic ring which optionally contains at least one O, S and/or additional N heteroatom, or $R^{12}$ is hydrogen and $R^{13}$ is hydroxyl, phenyl, or a single bond attached to —L—C(=O)—A;

B is hydroxyl, lower alkoxy, lower alkanoyloxy, azido, lower alkythio, arylthio, heteroarylthio, lower alkylsulfinyl, arylsulfinyl, heteroarylsulfinyl or a single bond attached to —L—C(=O)—$A^2$ where $A^2$ is a residue of a non-naturally occurring amino acid;

one of $R^{14}$ or $R^{15}$ is hydrogen and the other is hydrogen, lower alkyl, allyl, carboxyl-substituted lower alkyl, carbamoyl, lower alkyl- or aryl-substituted carbamoyl, a residue of an α-amino acid in which the carboxylate hydrogen is removed, or lower alkoxycarbonyl-substituted lower alkyl; or both $R^{14}$ and $R^{15}$ are lower alkyl or chlorine-substituted lower alkyl; or $R^{14}$ and $R^{15}$ are combined together to form —$CH_2CH_2DCH_2CH_2$— wherein D is —$CH_2$—, —NH—, —S— or —O—;

$R^{16}$ is hydroxyl, carbamoylamino, —$NR^8R^9$ guanidino, 2-imidazolylamino or a single bond attached to —L—C(=O)—A;

$R^{17}$ is the residue of an α-amino acid after removal of the amino group thereof, wherein the carboxyl group of the α-amino acid is optionally esterified by a lower alkyl alcohol or benzyl alcohol;

Y is hydroxyl, lower alkanoyloxy, carbamoyloxy, lower alkoxy, or a single bond attached to —L—C(=O)—A, or X and Y together may be —$CH_2OC(CH_3)_2O$—, O=, —$CH_2O$—, —$CH_2OCO_2$—, —$CH_2OC(=S)O$—, —$CH_2N(R^{18})CO_2$—, —$CH_2NHC(=S)O$—, —$CH_2OS(=O)O$—, —OC(=S)$NHCH_2$— or —O—C($R^{19}$)=N—$CH_2$—;

$R^{18}$ is hydrogen, lower alkyl, allyl, formylmethyl, —$CH_2CH$=NNHC(=NH)$NH_2$, —$CH_2CH$(—G)$CH_2$—J wherein G and J are independently hydroxyl or one of them is a single bond attached to —L—C(=O)—A; and $R^{19}$ is lower alkyl or lower alkylthio;

provided that one of $R^2$, $R^3$, $R^5$, $W^1$, $W^2$, X and Y contains a single bond attached to —L—C(=O)—A;

further provided that where $R^1$, $R^2$, $R^3$, $R^4$, $W^1$ and $W^2$ are H, Y cannot be hydroxyl when X is —$CH_2$—O—C(=O)$CH_2NH_2$ or —$CH_2$—O—C(=O)$CH_2NH$-cbz;

*and further provided that the solubilizing group A is other than a residue of 3-dimethylaminobutyric acid, lysyl-β-alanine, or succinic acid.*

*39. An indolocarbazole ester of formula Q—L—C(=O)—A wherein:*

*A is a solubilizing group selected from the group consisting of a residue of a non-naturally occurring amino acid, a dipeptide residue, —$(CH_2)_mZ$, —$(CH_2)_mC(=O)NH(CH_2)_mZ$, —$(CH_2)_mC(=O)NH$—Z, —$(CH_2)_mZ(CH_2)_mZ$, branched —$(CH_2)_nCH[(CH_2)_mZ]_2$, —$(CH_2)_m$—$Z[(CH_2)_mZ]_2$, —$(CH_2)_n$—$A^1$, —$(CH_2)_n$-heteroaryl and —$NH(CH_2)_mN(CH_3)_2$; wherein:*

*n is an integer from 0 to 5;*

*m is an integer from 1–6;*

*Z is selected from the group consisting of a basic group, —$C(=NH)NH_2$, cyclic amidine, —$NHC(NH_2)=NR^{11}$, cyclic guanidine and an acidic group; and*

*$A^1$ is aryl or heteroaryl substituted with one to three substituents of formula —$(CH_2)_nZ$;*

*L is oxygen; and*

*Q is an indolocarbazole residue of formula:*

I

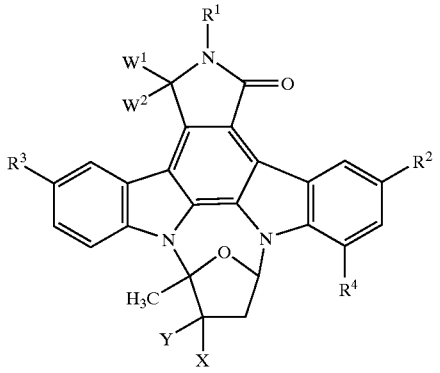

*wherein*

*$R^1$ is hydrogen, carbamoyl, lower alkyl, amino, lower alkanoyl, —$CH_2R^5$ or —$CH_2CH_2R^5$;*

*$R^5$ is halogen, amino, di-lower alkylamino, hydroxyl, a single bond attached to —L—C(=O)—A or lower alkylamino optionally substituted with hydroxyl or a single bond attached to —L—C(=O)—A;*

*$R^2$ and $R^3$ are independently hydrogen, hydroxyl, cyano, lower alkoxy, halogen, hydroxymethyl, lower alkoxymethyl, lower alkylthiomethyl, lower alkylsulfinylmethyl, arylthiomethyl, heteroarylthiomethyl, arylsulfinylmethyl, heteroarylsulfinylmethyl, arylmethylthiomethyl, heteroarylmethylthiomethyl, CH=NNHC(=NH)$NH_2$, nitro, lower alkanoyl, lower alkanoyloxy, sulfonic acid, —$SO_2NR^8R^9$, —$OC(=O)NR^8R^9$, —$CH=NNR^8R^9$, —$NR^6R^7$, —$OCO_2R^{10}$, —$NHC(=O)NHR^{11}$, —$CH_2OC(=O)NHR^{11}$, —$NHCO_2R^{11}$, lower alkylsulfonylmethyl, (dialkylamino)alkylthiomethyl, a single bond attached to —L—C(=O)—A, or lower alkyl optionally substituted with hydroxyl or a single bond attached to —L—C(=O)—A;*

*one of $R^6$ and $R^7$ is hydrogen and the other is hydrogen, lower alkyl, carbamoyl, lower alkylaminocarbonyl, lower alkanoyl or phenylaminocarbonyl; or $R^6$ and $R^7$ are both lower alkyl;*

*$R^8$ and $R^9$ are independently hydrogen, lower alkyl, aryl, heteroaryl or $R^8$ and $R^9$ together with the nitrogen atom to which they are attached, form a heterocycle;*

*$R^{10}$ is lower alkyl or substituted or unsubstituted phenyl;*

*$R^{11}$ is hydrogen or lower alkyl;*

*$R^4$ is hydrogen, amino or —$NHC(=O)NHC_2H_5$;*

*one of $W^1$ and $W^2$ is hydrogen, and the other is selected from the group consisting of hydrogen, hydroxyl, lower alkoxy, lower alkylthio and a single bond attached to —L—C(=O)—A, or $W^1$ and $W^2$ combined together are oxygen;*

*X is hydrogen, —$CH_2$—$NHC(=O)O$—$C_6H_5$, formyl, carboxyl, alkoxycarbonyl having from 2 to 13 carbons, cycloalkoxycarbonyl having from 4 to 11 carbons, —$(CH_2)_nCH_2N(R^{11})_2$ wherein n is an integer from 0 to 5, —$C(=O)NR^{12}R^{13}$, —$CH_2B$, —$NR^{14}R^{15}$, —$N=CHN(CH_3)_2$, —$OCOCH_2CH_2CO_2H$, lower alkylhydrazinocarbonyl, —CH=N—$R^{16}$, —$CONHR^{17}$, a group of formula:*

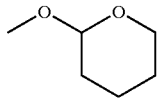

*$R^{12}$ and $R^{13}$ are independently hydrogen, lower alkyl, phenyl, lower alkyl optionally substituted by hydroxyl or by a single bond attached to —L—C(=O)—A, or $R^{12}$ and $R^{13}$ are combined together to form a 3–6 carbon heterocyclic ring which optionally contains at least one O, S and/or additional N heteroatom, or $R^{12}$ is hydrogen and $R^{13}$ is hydroxyl, phenyl, or a single bond attached to —L—C(=O)—A;*

*B is hydroxyl, lower alkoxy, lower alkanoyloxy, azido, lower alkythio, arylthio, heteroarylthio, lower alkylsulfinyl, arylsulfinyl, heteroarylsulfinyl or a single bond attached to —L—C(=O)—A;*

*one of $R^{14}$ or $R^{15}$ is hydrogen and the other is hydrogen, lower alkyl, allyl, carboxyl-substituted lower alkyl, carbamoyl, lower alkyl- or aryl-substituted carbamoyl, a residue of an α-amino acid in which the carboxylate hydrogen is removed, or lower alkoxycarbonyl-substituted lower alkyl; or both $R^{14}$ and $R^{15}$ are lower alkyl or chlorine-substituted lower alkyl; or $R^{14}$ and $R^{15}$ are combined together to form —$CH_2CH_2DCH_2CH_2$— wherein D is —$CH_2$—, —NH—, —S— or —O—;*

*$R^{16}$ is hydroxyl, carbamoylamino, —$NR^8R^9$ guanidino, 2-imidazolylamino or a single bond attached to —L—C(=O)—A;*

*$R^{17}$ is the residue of an α-amino acid after removal of the amino group thereof, wherein the carboxyl group of the α-amino acid is optionally esterified by a lower alkyl alcohol or benzyl alcohol;*

*Y is hydroxyl, lower alkanoyloxy, carbamoyloxy, lower alkoxy, or a single bond attached to —L—C(=O)—A, or X and Y together may be —$CH_2OC(CH_3)_2O$—, O=, —$CH_2O$—, —$CH_2OCO_2$—, —$CH_2OC(=S)O$—, —$CH_2N(R^{18})CO_2$—, —$CH_2NHC(=S)O$—, —$CH_2OS(=O)O$—, —$OC(=S)NHCH_2$— or —O—$C(R^{19})$=N—$CH_2$—;*

*$R^{18}$ is hydrogen, lower alkyl, allyl, formylmethyl, —$CH_2CH=NNHC(=NH)NH_2$, —$CH_2CH$(—G)*

$CH_2$—J where G and J are independently hydroxyl or one of them is a single bond attached to —L—C(=O)—A; and $R^{19}$ is lower alkyl or lower alkylthio;

provided that one of $R^2$, $R^3$, $R^5$, $W^1$, $W^2$, X and Y contains a single bond attached to —L— C(=O)—A;

further provided that where $R^1$, $R^2$, $R^3$, $R^4$, $W^1$ and $W^2$ are H, Y cannot be hydroxyl when X is —$CH_2$—O—C(=O)$CH_2NH_2$ or —$CH_2$—O—C(=O)$CH_2$NH—cbz;

and further provided that the solubilizing group A is other than a residue of 3-dimethylaminobutyric acid, lysyl-β-alanine, or succinic acid.

40. An indolocarbazole ester of formula Q—L—C(=O)—A wherein:

A is a solubilizing group selected from the group consisting of an amino acid residue, a dipeptide residue, —$(CH_2)_mZ$, —$(CH_2)_mC(=O)NH(CH_2)_mZ$, —$(CH_2)_mC(=O)NH$—Z, —$(CH_2)_mZ(CH_2)_mZ$, branched —$(CH_2)_nCH[(CH_2)_mZ]_2$, —$(CH_2)_m$—Z$[(CH_2)_m, Z]_2$—$(CH_2)N$—$A^1$, —$(CH_2)_n$-heteroaryl and —$NH(CH_2)_mN(CH_3)_2$;

wherein:

n is an integer from 0 to 5;

m is an integer from 1–6;

Z is selected from the group consisting of a basic group, —C(=NH)$NH_2$, cyclic amidine, —NHC$(NH_2)$=$NR^{11}$, cyclic guanidine and an acidic group; and $A^1$ is aryl or heteroaryl substituted with one to three substituents of formula —$(CH_2)_nZ$;

L is oxygen; and

Q is an indolocarbazole residue of formula:

I

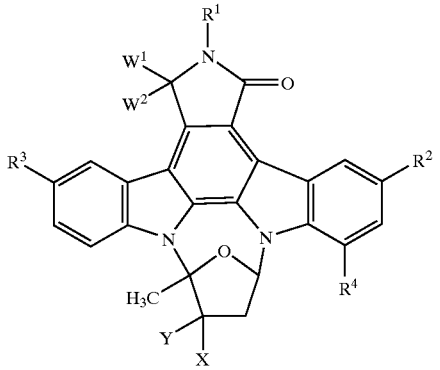

wherein:

$R^1$ is hydrogen, carbamoyl, lower alkyl, amino, lower alkanoyl, —$CH_2R^5$ or —$CH_2CH_2R^5$;

$R^5$ is halogen, amino, di-lower alkylamino, hydroxyl, a single bond attached to —L— C(=O)—A, or lower alkylamino optionally substituted with hydroxyl or a single bond attached to —L—C(=O)—A;

$R^2$ and $R^3$ are independently hydrogen, hydroxyl, cyano, lower alkoxy, halogen, hydroxymethyl, lower alkoxymethyl, lower alkylthiomethyl, lower alkylsulfinylmethyl, arylthiomethyl, heteroarylthiomethyl, arylsulfinylmethyl, heteroarylsulfinylmethyl, arylmethylthiomethyl, heteroarylmethylthiomethyl, CH=NNHC(=NH)$NH_2$, nitro, lower alkanoyl, lower alkanoyloxy, sulfonic acid, —$SO_2NR^8R^9$, —OC(=O)$NR^8R^9$, —CH=NN$R^8R^9$, —$NR^6R^7$, —$OCO_2R^{10}$, —NHC(=O)$NHR^{11}$, —$CH_2$OC(=O)$NHR^{11}$, —NH$CO_2R^{11}$, lower alkylsulfonylmethyl, (dialkylamino)alkylthiomethyl, a single bond attached to —L—C(=O)—A, or lower alkyl optionally substituted with hydroxyl or a single bond attached to —L—C(=O)—A;

one of $R^6$ and $R^7$ is hydrogen and the other is hydrogen, lower alkyl, carbamoyl, lower alkylaminocarbonyl, lower alkanoyl or phenylaminocarbonyl; or $R^6$ and $R^7$ are both lower alkyl;

$R^8$ and $R^9$ are independently hydrogen, lower alkyl, aryl, heteroaryl or $R^8$ and $R^9$ together with the nitrogen atom to which they are attached, form a heterocycle;

$R^{10}$ is lower alkyl or substituted or unsubstituted phenyl;

$R^{11}$ is hydrogen or lower alkyl;

$R^4$ is hydrogen, amino or —NHC(=O)$NHC_2H_5$;

one of $W^1$ and $W^2$ is hydrogen, and the other is selected from the group consisting of hydrogen, hydroxyl, lower alkoxy, lower alkylthio and a single bond attached to —L—C(=O)—A, or $W^1$ and $W^2$ combined together are oxygen;

X is hydrogen, —$CH_2$—NHC(=O)O—$C_6H_5$, formyl, carboxyl, alkoxycarbonyl having from 2 to 13 carbons, cycloalkoxycarbonyl having from 4 to 11 carbons, —$(CH_2)_nCH_1N(R^{11})_2$ wherein n is an integer from 0 to 5, —C(=O)$NR^{12}R^{13}$, —$CH_2$B, —$NR^{14}R^{15}$, —N=CHN$(CH_3)_2$, —OCOC$H_2CH_2CO_2H$, lower alkylhydrazinocarbonyl, —CH=N—$R^{16}$, —CONH$R^{17}$, a group of formula:

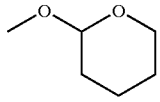

$R^{12}$ and $R^{13}$ are independently hydrogen, lower alkyl, phenyl, lower alkyl optionally substituted by hydroxyl or by a single bond attached to —L—C(=O)—A, or $R^{12}$ and $R^{13}$ are combined together to form a 3–6 carbon heterocyclic ring which optionally contains at least one O, S and/or additional N heteroatom, or $R^{12}$ is hydrogen and $R^{13}$ is hydroxyl, phenyl, or a single bond attached to —L—C(=O)—A;

B is hydroxyl, lower alkoxy, lower alkyanoyloxy, azido, lower alkythio, arylthio, heteroarylthio, lower alkylsufinyl, arylsulfinyl, heteroarylsulfinyl or a single bond attached to —L—C(=O)—$A^4$ where $A^4$ is a residue of an amino acid other than an α-amino acid;

one of $R^{14}$ or $R^{15}$ is hydrogen and the other is hydrogen, lower alkyl, allyl, carboxyl-substituted lower alkyl, carbamoyl, lower alkyl- or aryl-substituted carbamoyl, a residue of an α-amino acid in which the carboxylate hydrogen is removed, or lower alkoxycarbonyl-substituted lower alkyl; or both $R^{14}$ and $R^{15}$ are lower alkyl or chlorine-substituted lower alkyl; or $R^{14}$ and $R^{15}$ are combined to form —$CH_2CH_2DCH_2CH_2$— wherein D is —$CH_2$—, —NH—, —S— or —O—;

$R^{16}$ is hydroxyl, carbamoylamino, —$NR^8R^9$ guanidino, 2-imidazolylamino or a single bond attached to —L—C(=O)—A;

$R^{17}$ is the residue of an α-amino acid after removal of the amino group thereof, wherein the carboxyl group of the α-amino acid is optionally esterified by a lower alkyl alcohol or benzyl alcohol;

Y is hydroxyl, lower alkanoyloxy, carbamoyloxy, lower alkoxy, or a single bond attached to —L—C(=O)—A, or X and Y together may be $—CH_2OC(CH_3)_2O—$, O=, $—CH_2O—$, $—CH_2OCO_2—$, $—CH_2OC(=S)O—$, $—CH_2N(R^{18})CO_2—$, $—CH_2NHC(=S)O—$, $—CH_2OS(=O)O—$, $—OC(=S)NHCH_2—$ or $—O—C(R^{19})=N—CH_2—$;

$R^{18}$ is hydrogen, lower alkyl, allyl, formylmethyl, $—CH_2CH=NNHC(=NH)NH_2$, $—CH_2CH(—G)CH_2—J$ wherein G and J are independently hydroxyl or one of them is a single bond attached to —L—C(=O)—A; and $R^{19}$ is lower alkyl or lower alkylthio;

provided that one of $R^2$, $R^3$, $R^5$, $W^1$, $W^2$, X and Y contains a single bond attached to —L— C(=O)—A;

further provided that where $R^1$, $R^2$, $R^3$, $R^4$, $W^1$ and $W^2$ are H, Y cannot be hydroxyl when X is $—CH_2—O—C(=O)CH_2NH_2$ or $—CH_2—O—C(=O)CH_2NH$-cbz;

and further provided that the solubilizing group A is other than a residue of 3-dimethylaminobutyric acid, lysyl-β-alanine, or succinic acid.

41. An indolocarbazole ester of formula Q—L—C(=O)—A wherein:

A is a solubilizing group selected from the group consisting of a residue or an amino acid other than an α-amino acid, a dipeptide residue, $—(CH_2)_mZ$, $—(CH_2)_mC(=O)NH(CH_2)_mZ$, $—(CH_2)_mC(=O)NH—Z$, $—(CH_2)_mZ(CH_2)_mZ$, branched $—(CH_2)_nCH[(CH_2)_mZ]_2$, $—(CH_2)_m—Z[(CH_2)_mZ]_2$, $—(CH_2)_n—A^1$, $—(CH_2)_n$-heteroaryl and $—NH(CH_2)_mN(CH_3)_2$; wherein:

n is an integer from 0 to 5;

m is an integer from 1–6;

Z is selected from the group consisting of a basic group, $—C(=NH)NH_2$, cyclic amidine, $—NHC(NH_2)=NR^{11}$, cyclic guanidine and an acidic group; and $A^1$ is aryl or heteroaryl substituted with one to three substituents of formula $—(CH_2)_nZ$;

L is oxygen; and

Q is an indolocarbazole residue of formula:

I

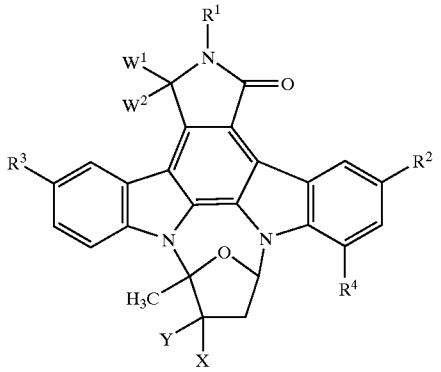

wherein:

$R^1$ is hydrogen, carbamoyl, lower alkyl, amino, lower alkanoyl, $—CH_2R^5$ or $—CH_2CH_2R^5$;

$R^5$ is halogen, amino, di-lower alkylamino, hydroxyl, a single bond attached to —L— C(=O)—A, or lower alkylamino optionally substituted with hydroxyl or a single bond attached to —L—C(=O)—A;

$R^2$ and $R^3$ are independently hydrogen, hydroxyl, cyano, lower alkoxy, halogen, hydroxymethyl, lower alkoxymethyl, lower alkylthiomethyl, lower alkylsulfinylmethyl, arylthiomethyl, heteroarylthiomethyl, arylsulfinylmethyl, heteroarylsulfinylmethyl, arylmethylthiomethyl, heteroarylmethylthiomethyl, $CH=NNHC(=NH)NH_2$, nitro, lower alkanoyl, lower alkanoyloxy, sulfonic acid, $—SO_2NR^8R^9$, $—OC(=O)NR^8R^9$, $—CH=NNR^8R^9$, $—NR^8R^7$, $—OCO_2R^{10}$, $—NHC(=O)NHR^{11}$, $—CH_2OC(=O)NHR^{11}$, $—NHCO_2R^{11}$, lower alkylsulfonylmethyl, (dialkylamino)alkylthiomethyl, a single bond attached to —L—C(=O)-A, or lower alkyl optionally substituted with hydroxyl or a single bond attached to —L—C(=O)—A;

one of $R^6$ and $R^7$ is hydrogen and the other is hydrogen, lower alkyl, carbamoyl, lower alkylaminocarbonyl, lower alkanoyl or phenylaminocarbonyl; or $R^6$ and $R^7$ are both lower alkyl;

$R^8$ and $R^9$ are independently hydrogen, lower alkyl, aryl, heteroaryl or $R^8$ and $R^9$ together with the nitrogen atom to which they are attached, form a heterocycle;

$R^{10}$ is lower alkyl or substituted or unsubstituted phenyl;

$R^{11}$ is hydrogen or lower alkyl;

$R^4$ is hydrogen, amino or $—NHC(=O)NHC_2H_5$;

one of $W^1$ and $W^2$ is hydrogen, and the other is selected from the group consisting of hydrogen, hydroxyl, lower alkoxy, lower alkylthio and a single bond attached to —L—C(=O)—A, or $W^1$ and $W^2$ combined together are oxygen;

X is hydrogen, $—CH_2—NHC(=O)O—C_6H_5$, formyl, carboxyl, alkoxycarbonyl having from 2 to 13 carbons, cycloalkoxycarbonyl having from 4 to 11 carbons, $—(CH_2)_nCH_2N(R^{11})_2$ wherein n is an integer from 0 to 5, $—C(=O)NR^{12}R^{13}$, $—CH_2B$, $—NR^{14}R^{15}$, $—N=CHN(CH_3)_2$, $—OCOCH_2CH_2CO_2H$, lower alkylhydrazinocarbonyl, $—CH=N—R^{16}$, $—CONHR^{17}$, a group of formula:

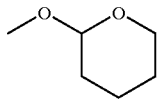

$R^{12}$ and $R^{13}$ are independently hydrogen, lower alkyl, phenyl, lower alkyl optionally substituted by hydroxyl or by a single bond attached to —L—C(=O)—A, or $R^{12}$ and $R^{13}$ are combined together to form a 3–6 carbon heterocyclic ring which optionally contains at least one O, S and/or additional N heteroatom, or $R^{12}$ is hydrogen and $R^{13}$ is hydroxyl, phenyl, or a single bond attached to —L—C(=O)—A;

B is hydroxyl, lower alkoxy, lower alkanoyloxy, azido, lower alkylthio, arylthio, heteroarylthio, lower alkylsulfinyl, arylsulfinyl, heteroarylsulfinyl or a single bond attached to —L—C(=O)—A;

one of $R^{14}$ or $R^{15}$ is hydrogen and the other is hydrogen, lower alkyl, allyl, carboxyl-substituted lower alkyl, carbamoyl, lower alkyl- or aryl-substituted carbamoyl, a residue of an α-amino acid in which the carboxylate hydrogen is removed, or lower alkoxycarbonyl-substituted lower alkyl; or both $R^{14}$ and $R^{15}$ are lower alkyl or chlorine-substituted lower alkyl; or $R^{14}$ and $R^{15}$ are combined together to form $—CH_2CH_2DCH_2CH_2—$ wherein D is $—CH_2—$, —NH—, —S— of —O—;

*$R^{16}$ is hydroxyl, carbamoylamino, —$NR^8R^9$ guanidino, 2-imidazolylamino or a single bond attached to —L—C(═O)—A;*

*$R^{17}$ is the residue of an α-amino acid after removal of the amino group thereof, wherein the carboxyl group of the α-amino acid is optionally esterified by a lower alkyl alcohol or benzyl alcohol;*

*Y is a hydroxyl, lower alkanoyloxy, carbamoyloxy, lower alkoxy, or a single bond attached to —L—C(═O)—A, or X and Y together may be —$CH_2OC(CH_3)_2O$—, O═, —$CH_2O$—, —$CH_2OCO_2$—, —$CH_2OC$(═S)O—, —$CH_2N(R^{18})CO_2$—, —$CH_2NHC$(═S)O—, —$CH_2OS$(═O)O—, —OC(═S)$NHCH_2$—or —O—C($R^{19}$)═N—$CH_2$—;*

*$R^{18}$ is hydrogen, lower alkyl, allyl, formylmethyl, —$CH_2CH$═NNHC(═NH)$NH_2$, —$CH_2CH$(—G)$CH_2$—J wherein G and J are independently hydroxyl or one of them is a single bond attached to —L—C(═O)—A; and*

*$R^{19}$ is lower alkyl or lower alkylthio;*

*provided that one of $R^2$, $R^3$, $R^5$, $W^1$, $W^2$, and X and Y contains a single bond attached to —L— C(═O)—A;*

*further provided that where $R^1$, $R^2$, $R^3$, $R^4$, $W^1$ and $W^2$ are H, Y cannot be hydroxyl when X is —$CH_2$—O—C(═O)$CH_2NH_2$ or —$CH_2$—O—C(═O)$CH_2NH$-cbz;*

*and further provided that the solubilizing group A is other than a residue of 3-dimethylaminobutyric acid, lysyl-β-alanine, or succinic acid.*

*42. The indolocarbazole ester of claim 40 wherein $A^4$ is a residue of a β-amino acid.*

*43. The indolocarbazole ester of claim 40 wherein $A^4$ is a residue of a γ-amino acid.*

*44. The indolocarbazole ester of claim 40 wherein $A^4$ is a residue of a δ-amino acid.*

*45. The indolocarbazole ester of claim 41 wherein A is a residue of a β-amino acid.*

*46. The indolocarbazole ester of claim 41 wherein A is a residue of a γ-amino acid.*

*47. The indolocarbazole ester of claim 41 wherein A is a residue of a δ-amino acid.*

* * * * *

UNITED STATES PATENT AND TRADEMARK OFFICE

CERTIFICATE OF CORRECTION

PATENT NO. : RE 38,332 E
DATED : November 25, 2003
INVENTOR(S) : Mallamo et al.

It is certified that error appears in the above-identified patent and that said Letters Patent is hereby corrected as shown below:

Title page,
Item [56], References Cited, FOREIGN PATENT DOCUMENTS,
"WO 94/02488" reference, please delete "3/1994" and insert -- 2/1994 -- therefor.
OTHER PUBLICATIONS, "Joyce, et al.," reference, please delete "monosaccaride" and insert -- monosaccharide -- therefor.

Column 4,
Lines 25-38, please delete "

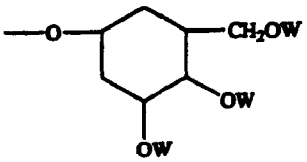

" and insert

-- 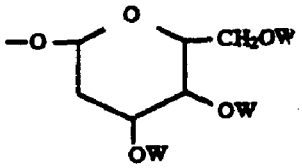

-- therefor.

Column 5,
Line 24, please delete "$-(CH_2)_mC(=L)NH(CH_2)_m$" and insert -- $-(CH_2)_mC(=O)NH(CH_2)_m$ -- therefor.

Column 6,
Line 30, please delete "indolcarbazole" and insert -- indolocarbazole -- therefor.

Column 8,
Line 15, please delete "is a" and insert -- is as -- therefor.

Column 9,
Line 66, please delete the second occurrence of "be".

Column 12,
Line 13, please delete "tetrahydrouran" and insert -- tetrahydrofuran -- therefor.
Line 24, please delete "Boc-lysine(Box)-OH" and insert -- Boc-lysine(boc)-OH -- therefor.

Column 13,
Line 23, please delete "dissolve" and insert -- dissolved -- therefor.

UNITED STATES PATENT AND TRADEMARK OFFICE

CERTIFICATE OF CORRECTION

PATENT NO. : RE 38,322 E
DATED : November 25, 2003
INVENTOR(S) : Mallamo et al.

It is certified that error appears in the above-identified patent and that said Letters Patent is hereby corrected as shown below:

Column 17,
Line 30, please delete "stolidity" and insert -- solubility of -- therefor.

Column 19,
Line 27, please delete "$\mu$-alaninate" and insert -- β-alaninate -- therefor.

Column 25,
Line 51, please delete "α-Aminosobutyric" and insert -- α-Aminoisobutyric -- therefor.

Column 27,
Line 48, please delete "Cystine" and insert -- Cysteine -- therefor.

Column 28,
Line 63, please delete "hydroxylmethyl" and insert -- hydroxymethyl -- therefor.

Column 29,
Line 31, please delete "$–OCOCH_2CH_2CO_9H$" and insert -- $–OCOCH_2CH_2CO_2H$ -- therefor.

Column 30,
Line 5, please delete "$–CH_2OC(CH_3)_2(–$," and insert -- $–CH_2OC(CH_3)_2O–$, -- therefor.
Line 8, please delete "of" and insert -- or -- therefor.
Line 28, please delete "$–(CH_m)_mZ$" and insert -- $– (CH_2)_mZ$ -- therefor.
Lines 29-30, please delete "$–(CH_2)_nCH[i\ CH_2)_mZ]_2$" and insert
-- $–(CH_2)_nCH[(CH_2)_mZ]_2$ -- therefor.

Column 33,
Line 42, please delete "one or" and insert -- one of -- therefor.

Column 39,
Line 20, please delete "$[(CH_2)_{mv}\ Z]_2–(CH_2)N–A^1$" and insert -- $[(CH_2)_m,Z]_2, –CH_2)_n–A^1$ -- therefor.

Column 40,
Line 26, please delete "$–(CH_2)_nCH_1N(R^{11})_2$" and insert -- $–(CH_2)_nCH_2N(R^{11})_2$ -- therefor.

UNITED STATES PATENT AND TRADEMARK OFFICE

CERTIFICATE OF CORRECTION

PATENT NO. : RE 38,322 E
DATED : November 25, 2003
INVENTOR(S) : Mallamo et al.

It is certified that error appears in the above-identified patent and that said Letters Patent is hereby corrected as shown below:

Column 42,
Line 67, please delete "of" and insert -- or -- therefor.

Signed and Sealed this

Eighteenth Day of October, 2005

JON W. DUDAS
*Director of the United States Patent and Trademark Office*